US010822661B2

United States Patent
Dahiya et al.

(10) Patent No.: US 10,822,661 B2
(45) Date of Patent: Nov. 3, 2020

(54) METHOD OF MULTIVARIATE MOLECULE ANALYSIS

(71) Applicant: MIODx, San Jose, CA (US)

(72) Inventors: Rajvir Dahiya, Hayward, CA (US); M. Allen Northrup, Orinda, CA (US)

(73) Assignee: MIODx, San Jose, CA (US)

( * ) Notice: Subject to any disclaimer, the term of this patent is extended or adjusted under 35 U.S.C. 154(b) by 524 days.

(21) Appl. No.: 15/504,600

(22) PCT Filed: Sep. 3, 2015

(86) PCT No.: PCT/US2015/048423
§ 371 (c)(1),
(2) Date: Feb. 16, 2017

(87) PCT Pub. No.: WO2016/037000
PCT Pub. Date: Mar. 10, 2016

(65) Prior Publication Data
US 2017/0233825 A1     Aug. 17, 2017

Related U.S. Application Data

(60) Provisional application No. 62/045,917, filed on Sep. 4, 2014.

(51) Int. Cl.
| | | |
|---|---|---|
| *C12Q 1/68* | (2018.01) | |
| *C12P 19/34* | (2006.01) | |
| *C12Q 1/6886* | (2018.01) | |
| *G01N 33/574* | (2006.01) | |
| *G16B 25/00* | (2019.01) | |
| *G16H 50/20* | (2018.01) | |

(52) U.S. Cl.
CPC ..... *C12Q 1/6886* (2013.01); *G01N 33/57484* (2013.01); *C12Q 2600/112* (2013.01); *C12Q 2600/154* (2013.01); *C12Q 2600/156* (2013.01); *C12Q 2600/158* (2013.01); *C12Q 2600/178* (2013.01); *G16B 25/00* (2019.02); *G16H 50/20* (2018.01)

(58) Field of Classification Search
CPC ............ C12Q 1/6886; C12Q 2600/112; C12Q 2600/154; C12Q 2600/158; C12Q 2600/178; C12Q 1/68
See application file for complete search history.

(56) References Cited

U.S. PATENT DOCUMENTS

| | | |
|---|---|---|
| 2010/0179213 A1 | 7/2010 | Patrawala et al. |
| 2012/0028264 A1 | 2/2012 | Shak et al. |
| 2017/0275702 A1* | 9/2017 | Dahiya ............ G01N 33/57484 |

FOREIGN PATENT DOCUMENTS

WO    WO2013041731 A1    3/2013

OTHER PUBLICATIONS

Bushce, S. et al. Cancer Res; 73(14); 4323-36 (Year: 2013).*
Illumina Technical Note: RNA Analysis. Merging Gene Expression and Methylation Data: Gene expression profiling data can be integrated with DNA methylation data in BeadStudio, providing researchers a powerful approach to studying gene expression regulation. www.illumina.com/documents/products/tech (Year: 2010).*
Luo, W. et al. "Isolation and genome-wide expression and methylation characterization of CD31+ cells from normal and malignant human prostate tissue" Oncotarget Aug. 21, 2013; 4: 1472-1483 (Year: 2013).*
Hoshikawa, Y. et al. Physiol Genomics 12: 209-219, 2003. (Year: 2003).*
Cobb, J.P. et al. Crit Care Med 2002 vol. 30, No. 12 (Year: 2002).*
Cheung, V.G. et al. Nature Genetics, vol. 33, Mar. 2003, pp. 422-425. (Year: 2003).*
Chen, G. et al. Molecular & Cellular Proteomics 1.4, pp. 304-313. (Year: 2002).*
Kobayashi, N. et al. "Identification of miR-30d as a novel prognostic maker of prostate cancer." Oncotarget 2012; 3: 1455-1471 (Year: 2012).*
Pickl, et al. "Novel RNA Markers in Prostate Cancer: Functional Considerations and Clinical Translation", vol. 2014 (2014), Article ID 765207, 12 pages.

* cited by examiner

*Primary Examiner* — Stephen T Kapushoc
(74) *Attorney, Agent, or Firm* — Shweta Chandra; Bozicevic, Field & Francis LLP

(57) ABSTRACT

A multi-gene-based assay for analysis of the following: (a) oncogene expression; (b) DNA methylation of tumor suppressor genes; (c) non-coding RNA expression (microRNA profiling); and (d) long non-coding RNA expression in cancer samples is disclosed. The assay method and device for conducting the assay are applicable to diagnosis, prognosis, and treatment of various cancers such as lung, breast, colorectal, prostate, liver, bladder; kidney, cervix, pancreatic, gastric, brain, oral, endometrium, and ovary. The assay methods find use in avoidance or postponement of surgical removal of cancer tissue.

20 Claims, 59 Drawing Sheets

Specification includes a Sequence Listing.

| Patient # | AMACR Fold ≥1.2 | SOX4 Fold ≥1.2 | TMPRSS2 Fold ≥1.2 | TWIST1 Fold ≥1.2 | PSA Fold ≥1.2 | PAP Fold ≥1.2 |
|---|---|---|---|---|---|---|
| 375 | 7.115672 | 1.636938 | 0.90689 | 2.713209 | 0.811127 | 0.726483 |
| 376 | 11.65599 | 3.470155 | 2.469125 | 8.03334 | 3.069492 | 0.778085 |
| 377 | 53.74282 | 1.53262 | 2.39828 | 0.069976 | 10.47588 | 6.854256 |
| 378 | 37.87043 | 2.380063 | 2.073402 | 1.030968 | 2.640846 | 0.400257 |
| 379 | 112.2833 | 1.546493 | 8.1173 | 5.513621 | 4.540968 | 2.044857 |
| 380 | 118.6855 | 1.926524 | 0.767905 | 16.21211 | 0.392292 | 0.48971 |
| 381 | 43.20122 | 1.393777 | 1.630145 | 2.622604 | 1.137605 | 1.023847 |
| 382 | 8.736164 | 0.903753 | 0.040135 | 0.078183 | 0.14896 | 0.004178 |
| 383 | 33.03675 | 1.051173 | 5.348002 | 5.169411 | 11.11935 | 12.88839 |
| 384 | 23.45787 | 1.380317 | 2.214529 | 0.95 | 4.756828 | 1.922522 |
| 387 | 19.19954 | 3.175536 | 1.230291 | 5.237942 | 0.89131 | 0.607518 |
| 388 | 7.305586 | 1.023847 | 0.987601 | 0.499307 | 0.298748 | 1.170399 |
| 389 | 0.712519 | 2.057653 | 0.718968 | 5.344296 | 0.670356 | 0.436181 |
| 390 | 22.76902 | 0.633317 | 4.626753 | 0.364502 | 8.711976 | 3.01467 |
| 391 | 0.427798 | 3.328795 | 1.090508 | 0.341273 | 0.601235 | 0.312949 |
| 392 | 9.474173 | 0.383953 | 0.189202 | 0.189202 | 0.222211 | 0.116387 |
| 393 | 7.351303 | 1.304051 | 0.497235 | 5.388934 | 0.364502 | 0.899378 |
| 394 | 8.901201 | 1.565909 | 0.856782 | 2.016705 | 1.163927 | 0.678772 |
| 395 | 53.26072 | 0.102522 | 0.960595 | 60.96883 | 1.141555 | 0.456283 |
| 396 | 65.93625 | 1.07848 | 1.131314 | 2.034959 | 1.517819 | 0.668037 |
| 397 | 1.333299 | 20.79263 | 0.650671 | 0.75576 | 1.225185 | 0.191445 |
| 398 | 14.4801 | 0.701736 | 0.319746 | 9.189587 | 0.488016 | 0.082241 |
| 399 | 1.547565 | 3.610003 | 0.108367 | 0.730522 | 0.911301 | 0.172659 |
| 400 | 0.196418 | 1.260503 | 1.358486 | 1.358486 | 1.64376 | 1.249196 |
| 401 | 50.73818 | 0.698339 | 0.209207 | 38.66617 | 0.542239 | 0.029421 |
| 402 | 3.936736 | 2.618971 | 1.087488 | 0.585605 | 1.014663 | 0.188286 |
| 403 | 2.353813 | 1.330529 | 1.715941 | 37.11679 | 5.021088 | 2.622604 |
| 404 | 0.882703 | 0.436786 | 0.734584 | 47.17661 | 1.082975 | 1.279872 |
| 405 | 2.231479 | 2.015308 | 0.944747 | 258.6756 | 1.79502 | 0.270744 |
| 406 | 0.048833 | 0.091189 | 0.071002 | 4.710891 | 0.078618 | 0.026793 |
| 410 | 18.44298 | 1.103434 | 0.621575 | 2.844155 | 0.777007 | 0.231808 |
| 414 | 1.545421 | 1.468151 | 0.365768 | 40.58852 | 1.003472 | 0.615146 |

| Positive | 27 | 20 | 11 | 21 | 12 | 8 |
|---|---|---|---|---|---|---|
| % | 84.8 | 62.5 | 34.4 | 65.6 | 37.5 | 25 |

FIG. 1A

| Patient # | RASSF1 % methyl ≥10 | TIG1 % methyl ≥10 | RARB % methyl ≥10 | MDR1 % methyl ≥10 | ID4 % methyl ≥10 |
|---|---|---|---|---|---|
| 375 | 0 | 42.695 | 0.405 | 0 | 1.09 |
| 376 | 32.005 | 69.165 | 28.895 | 0 | 6.08 |
| 377 | 92.035 | 11.925 | 34.09 | 6.56 | 1.285 |
| 378 | 38.21 | 28.975 | 31.765 | 8.315 | 0 |
| 379 | 14.495 | 52.155 | 47.195 | 29.92 | 0 |
| 380 | 10.94 | 50.125 | 21.505 | 36.84 | 0 |
| 381 | 63.085 | 0 | 25.375 | 53.71 | 3.525 |
| 382 | 13.145 | 57.865 | 17.82 | 38.55 | 24.085 |
| 383 | 10.92 | 0 | 26.26 | 0 | 41.755 |
| 384 | 0 | 0 | 12.58 | 6.915 | 12.755 |
| 387 | 20.135 | 61.6585 | 39.75 | 0 | 14.075 |
| 388 | 35.545 | 49.035 | 24.675 | 0 | 0 |
| 389 | 27.47 | 10.99 | 28.375 | 0 | 0 |
| 390 | 39.675 | 47.235 | 50.23 | 9.68 | 13.815 |
| 391 | 41.13 | 39.615 | 44.505 | 17.64 | 0 |
| 392 | 16.57 | 64.43 | 88.125 | 20.395 | 7.595 |
| 393 | 16.175 | 23.385 | 37.7 | 15.88 | 0 |
| 394 | 32.085 | 38.17 | 7.75 | 18.37 | 17.02 |
| 395 | 47.305 | 89.535 | 65.525 | 22.68 | 11.075 |
| 396 | 4.23 | 56.64 | 68.625 | 0 | 0 |
| 397 | 19.945 | 40.805 | 10.645 | 0 | 39.355 |
| 398 | 14.75 | 16.775 | 20.23 | 9.75 | 10.44 |
| 399 | 16.36 | 0 | 31.215 | 15.505 | 0 |
| 400 | 41.135 | 19.055 | 26.875 | 18.27 | 5.025 |
| 401 | 20.505 | 43.315 | 44.08 | 25.51 | 9.855 |
| 402 | 17.035 | 15.595 | 55.255 | 22.58 | 0 |
| 403 | 55.365 | 0 | 36.89 | 21.87 | 0 |
| 404 | 27.385 | 28.01 | 5.52 | 7.025 | 13.245 |
| 405 | 28.4 | 14.15 | 25.68 | 1.99 | 0 |
| 406 | 11.275 | 7.375 | 12.795 | 23.77 | 5.715 |
| 410 | 82.11 | 13.095 | 71.765 | 4.06 | 13.685 |
| 414 | 40.63 | 6.67 | 28.93 | 17.59 | 8.78 |

| Positive | 29 | 25 | 29 | 16 | 11 |
|---|---|---|---|---|---|
| % | 90.6 | 78.1 | 90.6 | 50 | 34.4 |

FIG. 1B

| Patient # | miR-205 | miR-31 | miR-23b | miR-101 | miR-185 |
|---|---|---|---|---|---|
| | Fold | Fold | Fold | Fold | Fold |
| | ≤0.8 | ≤0.8 | ≤0.8 | ≤0.8 | ≤0.8 |
| 375 | 0.263523 | 0.291587 | 0.632002 | 1.220101 | 1.266634 |
| 376 | 0.043616 | 0.046391 | 0.463294 | 0.787308 | 0.647073 |
| 377 | 0.016356 | 0.014298 | 0.409518 | 0.477311 | 0.312299 |
| 378 | 0.000907 | 0.005048 | 0.07371 | 0.225625 | 0.176287 |
| 379 | 0.021389 | 0.104386 | 0.176899 | 0.366275 | 0.441964 |
| 380 | 0.010302 | 0.026296 | 0.10897 | 0.127538 | 0.2375 |
| 381 | 0.042748 | 0.055978 | 0.588453 | 0.75576 | 0.654743 |
| 382 | 0.742262 | 1.122721 | 3.246758 | 3.755487 | 7.464264 |
| 383 | 0.081786 | 0.060037 | 0.393381 | 0.331022 | 1.087488 |
| 384 | 0.199851 | 0.27797 | 0.560583 | 0.721464 | 2.023706 |
| 387 | 0.11415 | 0.569197 | 0.412081 | 0.571965 | 0.356013 |
| 388 | 0.000604 | 0.002651 | 0.183392 | 0.08615 | 0.02588 |
| 389 | 0.031358 | 0.06012 | 0.126745 | 0.49141 | 0.649319 |
| 390 | 0.023309 | 0.023131 | 0.022703 | 0.248962 | 0.212863 |
| 391 | 0.00324 | 0.009712 | 0.369591 | 0.590496 | 0.46458 |
| 392 | 0.000907 | 0.377095 | 0.868742 | 0.779705 | 0.616426 |
| 393 | 0.036651 | 0.333556 | 0.329877 | 0.382094 | 0.513701 |
| 394 | 0.106801 | 0.07448 | 0.555554 | 0.374231 | 0.382094 |
| 395 | 0.049412 | 0.032487 | 0.877214 | 0.821311 | 0.384219 |
| 396 | 0.01639 | 0.044133 | 0.168872 | 0.388504 | 0.602486 |
| 397 | 0.009827 | 0.027299 | 0.406126 | 0.920826 | 1.348168 |
| 398 | 0.027337 | 0.062935 | 0.694478 | 0.695923 | 0.886382 |
| 399 | 5.92E-05 | 0.01592 | 0.195874 | 0.501388 | 0.719966 |
| 400 | 31.77896 | 122.1068 | 22756.64 | 7.895332 | 3.923116 |
| 401 | 0.000214 | 0.000144 | 4.42E05 | 0.004493 | 0.000639 |
| 402 | 0.000965 | 0.060665 | 1.224336 | 0.323985 | 0.547906 |
| 403 | 0.001764 | 0.018086 | 0.057352 | 0.239982 | 0.418703 |
| 404 | 3.810552 | 0.012904 | 1167.333 | 6.435267 | 13.14097 |
| 405 | 0.004687 | 10.55606 | 0.180992 | 0.259895 | 0.47533 |
| 406 | 0.004632 | 0.000231 | 17.67943 | 0.671752 | 1.051902 |
| 410 | 0.044409 | 0.000232 | 0.200823 | 0.706617 | 0.526316 |
| 414 | 0.384752 | 0.004219 | 0.654289 | 1.043189 | 1.081475 |
| Positive | 30 | 29 | 26 | 25 | 22 |
| % | 93.8 | 90.6 | 81.3 | 78.1 | 68.8 |

FIG. 1C

| Patient # | ZFAS1 | MALAT1 | Total | Gleason | pT | Survival | Month |
|---|---|---|---|---|---|---|---|
| | Fold | Fold | positive | | | | |
| | ≥1.2 | ≥1.2 | ≥12 | | | | |
| 375 | 0.93368 | 3.784231 | 8 | 3+4 | 2c | alive | |
| 376 | 0.054221 | 1.016775 | 13 | 3+3 | 2c | alive | |
| 377 | 0.418123 | 5.954581 | 14 | 3+4 | 2c | alive | |
| 378 | 0.790041 | 0.77164 | 12 | 4+3 | 2c | alive | |
| 379 | 3.869105 | 1.117287 | 16 | 4+3 | 3b | alive | |
| 380 | 4.30496 | 2.51926 | 14 | 3++3 | 2c | alive | |
| 381 | 1.816297 | 1.692317 | 14 | 3+4 | 2c | alive | |
| 382 | 4.4506 | 0.702222 | 8 | 3+4 | 2a | alive | |
| 383 | 1.283426 | 0.53812 | 13 | ? | 3c | alive | |
| 384 | 0.203063 | 0.734584 | 11 | 4+3 | 3a | alive | |
| 387 | 1.977942 | 1.271913 | 15 | 4+3 | 2c | alive | |
| 388 | 0.072645 | 2.306971 | 10 | 3+4 | 3a | dead | 3 |
| 389 | 9.842331 | 0.893166 | 11 | 3+3 | 2c | alive | |
| 390 | 5.712016 | 2.60088 | 15 | 3+4 | 2 | alive | |
| 391 | 0.088205 | 0.628071 | 10 | 3+4 | 2C | alive | |
| 392 | 5.925759 | 1.598812 | 11 | 3+3 | 2c | alive | |
| 393 | 4.793236 | 0.249827 | 13 | 3+4 | 2a | alive | |
| 394 | 0.162781 | 2.067661 | 13 | 3+3 | 2c | alive | |
| 395 | 0.257207 | 4.008326 | 11 | 3+3 | 2c | alive | |
| 396 | 3.071621 | 6.126232 | 12 | 3+4 | 2c | alive | |
| 397 | 0.541112 | 0.843816 | 10 | 3+3 | 2c | alive | |
| 398 | 0.098413 | 0.158549 | 10 | 3+3 | 2c | alive | |
| 399 | 0.247414 | 0.902501 | 10 | 4+3 | 3b | dead | 14 |
| 400 | 0.158879 | 0.102167 | 9 | 3+3 | 2c | alive | |
| 401 | 16.33619 | 2.228387 | 13 | 3+3 | 3 | dead | 48 |
| 402 | 3.655326 | 2.668446 | 13 | 3+3 | 2c | alive | |
| 403 | 0.850274 | 2.45377 | 15 | 3+3 | 3a | alive | |
| 404 | 4.655706 | 25.19386 | 8 | 3+3 | 2c | alive | |
| 405 | 13.25992 | 2.722628 | 13 | 3+3 | 2a | alive | |
| 406 | 43.683 | 5.555821 | 9 | 3+3 | 3a | dead | 24 |
| 410 | 2.987627 | 1.627886 | 13 | 3+3 | 2c | dead | 25 |
| 414 | 0.44074 | 0.853226 | 9 | 3+3 | 2c | dead | 78 |

| Positive | 17 | 18 | 17 |
|---|---|---|---|
| % | 53.1 | 56.3 | 53.1 |

FIG. 1D

| Patient # | | Ct | Ct-cont | CCND1 dCt | ddCt | F | Ct | Ct-cont | EGFR dCt | ddCt | F |
|---|---|---|---|---|---|---|---|---|---|---|---|
| 506 | N | 35.478 | 33.724 | 1.754 | | | 37.497 | 33.755 | 3.742 | | |
| | T | 33.598 | 31.679 | 1.919 | 0.165 | 0.89193 | 35.813 | 31.865 | 3.948 | 0.206 | 0.8669 |
| 507 | N | 34.232 | 31.41 | 2.822 | | | 35.894 | 31.497 | 4.397 | | |
| | T | 32.317 | 31.067 | 1.25 | -1.572 | 2.97317 | 34.599 | 31.045 | 3.554 | -0.843 | 1.7938 |
| 509 | N | 33.536 | 30.788 | 2.748 | | | 33.782 | 30.774 | 3.008 | | |
| | T | 31.047 | 28.91 | 2.137 | -0.611 | 1.52732 | 33.288 | 28.916 | 4.372 | 1.364 | 0.3885 |
| 510 | N | 35.205 | 34.604 | 0.601 | | | 40.5 | 34.232 | 6.268 | | |
| | T | 33.367 | 31.742 | 1.625 | 1.024 | 0.49175 | 35.926 | 31.673 | 4.253 | -2.015 | 4.0418 |
| 511 | N | 36.454 | 32.778 | 3.676 | | | 37.497 | 32.981 | 4.516 | | |
| | T | 33.936 | 30.369 | 3.567 | -0.109 | 1.07848 | 32.82 | 30.264 | 2.556 | -1.96 | 3.8906 |
| 512 | N | 36.668 | 34.851 | 1.817 | | | 38.781 | 34.503 | 4.278 | | |
| | T | 30.763 | 30.002 | 0.761 | -1.056 | 2.07916 | 34.756 | 29.693 | 5.063 | 0.785 | 0.5804 |
| 513 | N | 34.606 | 32.836 | 1.77 | | | 37.297 | 32.836 | 4.461 | | |
| | T | 33.831 | 31.552 | 2.279 | 0.509 | 0.70271 | 38.714 | 31.552 | 7.162 | 2.701 | 0.1538 |
| 515 | N | 38.657 | 33.293 | 5.364 | | | 38.626 | 33.293 | 5.333 | | |
| | T | 30.76 | 28.672 | 2.088 | -3.276 | 9.68667 | 33.613 | 28.672 | 4.941 | -0.392 | 1.3122 |
| 516 | N | 33.094 | 30.83 | 2.264 | | | 35.198 | 30.83 | 4.368 | | |
| | T | 28.104 | 26.368 | 1.736 | -0.528 | 1.44193 | 31.054 | 26.368 | 4.686 | 0.318 | 0.8022 |
| 517 | N | 35.346 | 32.952 | 2.394 | | | 37.051 | 32.952 | 4.099 | | |
| | T | 36.444 | 34.509 | 1.935 | -0.459 | 1.37459 | 40.5 | 34.509 | 5.991 | 1.892 | 0.2694 |
| 518 | N | 34.51 | 30.566 | 3.944 | | | 35.236 | 30.566 | 4.67 | | |
| | T | 29.674 | 26.738 | 2.936 | -1.008 | 2.01112 | 30.702 | 26.738 | 3.964 | -0.706 | 1.6313 |
| 519 | N | 35.93 | 31.961 | 3.969 | | | 35.575 | 31.961 | 3.614 | | |
| | T | 32.99 | 30.273 | 2.717 | -1.252 | 2.38171 | 34.044 | 30.273 | 3.771 | 0.157 | 0.8969 |
| 599 | N | 40 | 36.214 | 3.786 | | | 40 | 36.214 | 3.786 | | |
| | T | 39.39 | 37.068 | 2.322 | -1.464 | 2.75872 | 38.098 | 37.068 | 1.03 | -2.756 | 6.7552 |
| 611 | N | 36.883 | 36.372 | 0.511 | | | 36.365 | 36.372 | -0.007 | | |
| | T | 34.802 | 35.19 | -0.388 | -0.899 | 1.86477 | 36.694 | 35.19 | 1.504 | 1.511 | 0.3509 |
| 628 | N | 38.095 | 36.839 | 1.256 | | | 40.5 | 36.839 | 3.661 | | |
| | T | 34.164 | 34.444 | -0.28 | -1.536 | 2.89989 | 35.27 | 34.444 | 0.826 | -2.835 | 7.1354 |
| 634 | N | 40 | 36.165 | 3.835 | | | 42 | 36.165 | 5.835 | | |
| | T | 38.861 | 40 | -1.139 | -4.974 | 31.4285 | 42.5 | 40 | 2.5 | -3.335 | 10.091 |
| 635 | N | 38.156 | 40 | -1.844 | | | 38.59 | 40 | -1.41 | | |
| | T | 35.452 | 34.684 | 0.768 | 2.612 | 0.16357 | 35.881 | 34.684 | 1.197 | 2.607 | 0.1641 |

FIG. 2A

| Patient # | | Ct | Ct-cont | CCND1 dCt | ddCt | F | Ct | Ct-cont | EGFR dCt | ddCt | F |
|---|---|---|---|---|---|---|---|---|---|---|---|
| 636 | N | 38.425 | 40 | -1.575 | | | 40.3 | 40 | 0.3 | | |
| | T | 38.818 | 38.303 | 0.515 | 2.09 | 0.23488 | 39.324 | 38.303 | 1.021 | 0.721 | 0.6067 |
| 595 | N | 37.477 | 37.943 | -0.466 | | | 37.25 | 37.943 | -0.693 | | |
| | T | 35.123 | 32.385 | 2.738 | 3.204 | 0.10852 | 36.445 | 32.385 | 4.06 | 4.753 | 0.0371 |
| 596 | N | 40 | 37.09 | 2.91 | | | 36.817 | 37.09 | -0.273 | | |
| | T | 35.785 | 34.137 | 1.648 | -1.262 | 2.39828 | 36.038 | 34.137 | 1.901 | 2.174 | 0.2216 |
| 603 | N | 38.276 | 36.634 | 1.642 | | | 42 | 36.634 | 5.366 | | |
| | T | 35.667 | 34.305 | 1.362 | -0.28 | 1.2142 | 37.931 | 34.305 | 3.626 | -1.74 | 3.3404 |
| 604 | N | 38.341 | 37.806 | 0.535 | | | 42 | 37.806 | 4.194 | | |
| | T | 40 | 36.662 | 3.338 | 2.803 | 0.14329 | 40.6 | 36.662 | 3.938 | -0.256 | 1.2 |
| 609 | N | 38.991 | 37.267 | 1.724 | | | 42 | 37.267 | 4.733 | | |
| | T | 40 | 36.371 | 3.629 | 1.905 | 0.26702 | 38.633 | 36.371 | 2.262 | -2.471 | 5.5443 |
| 617 | N | 37.054 | 38.29 | -1.236 | | | 38.48 | 38.29 | 0.19 | | |
| | T | 40.1 | 35.408 | 4.692 | 5.928 | 0.01643 | 45 | 35.408 | 9.592 | 9.402 | 0.01 |
| 520 | N | 34.178 | 31.765 | 2.413 | | | 34.923 | 31.765 | 3.158 | | |
| | T | 29.172 | 27.702 | 1.47 | -0.943 | 1.92252 | 31.744 | 27.702 | 4.042 | 0.884 | 0.5419 |
| 521 | N | 32.505 | 30.813 | 1.692 | | | 34.519 | 30.813 | 3.706 | | |
| | T | 33.922 | 29.928 | 3.994 | 2.302 | 0.20278 | 33.68 | 29.928 | 3.752 | 0.046 | 0.9686 |
| 524 | N | 35.15 | 31.333 | 3.817 | | | 36.834 | 31.333 | 5.501 | | |
| | T | 29.836 | 26.999 | 2.837 | -0.98 | 1.97247 | 31.575 | 26.999 | 4.576 | -0.925 | 1.8987 |
| 529 | N | 34.045 | 31.22 | 2.825 | | | 34.653 | 31.22 | 3.433 | | |
| | T | 31.119 | 28.857 | 2.262 | -0.563 | 1.47734 | 33.529 | 28.857 | 4.672 | 1.239 | 0.4237 |
| 563 | N | 36.305 | 35.646 | 0.659 | | | 38.372 | 35.646 | 2.726 | | |
| | T | 36.704 | 34.09 | 2.614 | 1.955 | 0.25792 | 36.713 | 34.09 | 2.623 | -0.103 | 1.074 |
| 624 | N | 39.161 | 32.946 | 6.215 | | | 36.449 | 32.946 | 3.503 | | |
| | T | 32.259 | 28.347 | 3.912 | -2.303 | 4.93483 | 31.435 | 28.347 | 3.088 | -0.415 | 1.3333 |

FIG. 2A (Cont.)

| Patient # | | Ct | Ct-cont | miR-210 dCt | ddCt | F | Ct | Ct-cont | miR-21 dCt | ddCt | F |
|---|---|---|---|---|---|---|---|---|---|---|---|
| 506 | N | 28.585 | 24.354 | 4.231 | | | 22.101 | 24.354 | -2.253 | | |
| | T | 23.12 | 25.141 | -2.021 | -6.252 | 76.215 | 20.109 | 25.141 | -5.032 | -2.779 | 6.86376 |
| 507 | N | 26.666 | 23.327 | 3.339 | | | 21.446 | 23.327 | -1.881 | | |
| | T | 22.427 | 23.808 | -1.381 | -4.72 | 26.355 | 19.466 | 23.808 | -4.342 | -2.461 | 5.50598 |
| 509 | N | 24.974 | 22.033 | 2.941 | | | 19.164 | 22.033 | -2.869 | | |
| | T | 22.21 | 22.944 | -0.734 | -3.675 | 12.773 | 18.2 | 22.944 | -4.744 | -1.875 | 3.66802 |
| 510 | N | 27.025 | 24.699 | 2.326 | | | 21.4 | 24.699 | -3.299 | | |
| | T | 20.726 | 24.33 | -3.604 | -5.93 | 60.969 | 19.19 | 24.33 | -5.14 | -1.841 | 3.58258 |
| 511 | N | 26.306 | 23.903 | 2.403 | | | 20.006 | 23.903 | -3.897 | | |
| | T | 23.757 | 24.063 | -0.306 | -2.709 | 6.5387 | 18.928 | 24.063 | -5.135 | -1.238 | 2.35871 |
| 512 | N | 25.403 | 26.106 | -0.703 | | | 22.836 | 26.106 | -3.27 | | |
| | T | 22.609 | 23.404 | -0.795 | -0.092 | 1.0658 | 18.523 | 23.404 | -4.881 | -1.611 | 3.05464 |
| 513 | N | 25.875 | 22.522 | 3.353 | | | 21.257 | 22.522 | -1.265 | | |
| | T | 23.042 | 22.883 | 0.159 | -3.194 | 9.1514 | 18.421 | 22.883 | -4.462 | -3.197 | 9.1705 |
| 515 | N | 27.679 | 23.84 | 3.839 | | | 21.457 | 23.84 | -2.383 | | |
| | T | 20.383 | 21.506 | -1.123 | -4.962 | 31.168 | 17.851 | 21.506 | -3.655 | -1.272 | 2.41496 |
| 516 | N | 24.411 | 21.053 | 3.358 | | | 19.07 | 21.053 | -1.983 | | |
| | T | 18.104 | 19.394 | -1.29 | -4.648 | 25.072 | 15.834 | 19.394 | -3.56 | -1.577 | 2.98349 |
| 517 | N | 24.442 | 24.608 | -0.166 | | | 21.207 | 24.608 | -3.401 | | |
| | T | 21.883 | 25.987 | -4.104 | -3.938 | 15.327 | 18.382 | 25.987 | -7.605 | -4.204 | 18.4302 |
| 518 | N | 25.043 | 20.725 | 4.318 | | | 16.7 | 20.725 | -4.025 | | |
| | T | 19.337 | 20.012 | -0.675 | -4.993 | 31.845 | 15.503 | 20.012 | -4.509 | -0.484 | 1.39862 |
| 519 | N | 24.608 | 22.377 | 2.231 | | | 19.142 | 22.377 | -3.235 | | |
| | T | 20.863 | 22.307 | -1.444 | -3.675 | 12.773 | 17.716 | 22.307 | -4.591 | -1.356 | 2.55975 |
| 599 | N | 27.009 | 26.933 | 0.076 | | | 22.556 | 26.933 | -4.377 | | |
| | T | 22.735 | 27.471 | -4.736 | -4.812 | 28.09 | 21.69 | 27.471 | -5.781 | -1.404 | 2.64634 |

FIG. 2B

| Patient # | | Ct | Ct-cont | miR-210 dCt | ddCt | F | Ct | Ct-cont | miR-21 dCt | ddCt | F |
|---|---|---|---|---|---|---|---|---|---|---|---|
| 611 | N | 27.051 | 25.536 | 1.515 | | | 22.203 | 25.536 | -3.333 | | |
| | T | 24.139 | 27.192 | -3.053 | -4.568 | 23.719 | 22.851 | 27.192 | -4.341 | -1.008 | 2.01112 |
| 628 | N | 28.746 | 26.821 | 1.925 | | | 23.362 | 26.821 | -3.459 | | |
| | T | 22.601 | 25.031 | -2.43 | -4.355 | 20.464 | 20.319 | 25.031 | -4.712 | -1.253 | 2.38337 |
| 634 | N | 28.748 | 29.417 | -0.669 | | | 23.907 | 29.417 | -5.51 | | |
| | T | 25.096 | 30.016 | -4.92 | -4.251 | 19.041 | 22.753 | 30.016 | -7.263 | -1.753 | 3.37059 |
| 635 | N | 28.066 | 26.076 | 1.99 | | | 22.165 | 26.076 | -3.911 | | |
| | T | 22.807 | 26.128 | -3.321 | -5.311 | 39.698 | 19.749 | 26.128 | -6.379 | -2.468 | 5.53276 |
| 636 | N | 27.748 | 27.414 | 0.334 | | | 23.047 | 27.414 | -4.367 | | |
| | T | 23.58 | 27.217 | -3.637 | -3.971 | 15.682 | 21.199 | 27.217 | -6.018 | -1.651 | 3.14051 |
| 595 | N | 29.206 | 25.823 | 3.383 | | | 23.037 | 25.823 | -2.786 | | |
| | T | 23.857 | 26.414 | -2.557 | -5.94 | 61.393 | 20.17 | 26.414 | -6.244 | -3.458 | 10.9891 |
| 596 | N | 28.135 | 25.864 | 2.271 | | | 22.396 | 25.864 | -3.468 | | |
| | T | 22.257 | 26.214 | -3.957 | -6.228 | 74.957 | 20.522 | 26.214 | -5.692 | -2.224 | 4.67187 |
| 603 | N | 27.506 | 27.315 | 0.191 | | | 21.983 | 27.315 | -5.332 | | |
| | T | 24.128 | 27.026 | -2.898 | -3.089 | 8.5091 | 20.072 | 27.026 | -6.954 | -1.622 | 3.07801 |
| 604 | N | 29.055 | 31.142 | -2.087 | | | 24.831 | 31.142 | -6.311 | | |
| | T | 25.499 | 31.071 | -5.572 | -3.485 | 11.197 | 21.402 | 31.071 | -9.669 | -3.358 | 10.2532 |
| 609 | N | 29.551 | 28.357 | 1.194 | | | 23.07 | 28.357 | -5.287 | | |
| | T | 24.187 | 29.843 | -5.656 | -6.85 | 115.36 | 21.684 | 29.843 | -8.159 | -2.872 | 7.32079 |
| 617 | N | 27.506 | 26.1 | 1.406 | | | 22.811 | 26.1 | -3.289 | | |
| | T | 30.731 | 33.118 | -2.387 | -3.793 | 13.861 | 29.352 | 33.118 | -3.766 | -0.477 | 1.39185 |
| 520 | N | 24.543 | 21.3 | 3.243 | | | 17.926 | 21.3 | -3.374 | | |
| | T | 18.549 | 20.356 | -1.807 | -5.05 | 33.128 | 16.103 | 20.356 | -4.253 | -0.879 | 1.8391 |
| 521 | N | 22.869 | 21.484 | 1.385 | | | 18.497 | 21.484 | -2.987 | | |
| | T | 21.509 | 19.59 | 1.919 | 0.534 | 0.6906 | 16.015 | 19.59 | -3.575 | -0.588 | 1.50316 |
| 524 | N | 25.169 | 21.507 | 3.662 | | | 19.018 | 21.507 | -2.489 | | |
| | T | 19.025 | 19.787 | -0.762 | -4.424 | 21.466 | 15.214 | 19.787 | -4.573 | -2.084 | 4.23981 |
| 529 | N | 24.144 | 21.041 | 3.103 | | | 18.578 | 21.041 | -2.463 | | |
| | T | 19.816 | 21.402 | -1.586 | -4.689 | 25.795 | 16.72 | 21.402 | -4.682 | -2.219 | 4.65571 |
| 563 | N | 24.736 | 24.17 | 0.566 | | | 20.366 | 24.17 | -3.804 | | |
| | T | 19.187 | 23.395 | -4.208 | -4.774 | 27.36 | 16.81 | 23.395 | -6.585 | -2.781 | 6.87329 |
| 624 | N | 25.074 | 23.072 | 2.002 | | | 18.598 | 23.072 | -4.474 | | |
| | T | 20.57 | 21.714 | -1.144 | -3.146 | 8.852 | 17.321 | 21.714 | -4.393 | 0.081 | 0.9454 |

FIG. 2B (Cont.)

| Patient # | | Ct | Ct-cont | miR-23b dCt | ddCt | F | Ct | Ct-cont | miR-34b dCt | ddCt | F |
|---|---|---|---|---|---|---|---|---|---|---|---|
| 506 | N | 26.176 | 24.354 | 1.822 | | | 24.515 | 24.354 | 0.161 | | |
| | T | 26.484 | 25.141 | 1.343 | -0.479 | 1.39 | 25.385 | 25.141 | 0.244 | 0.083 | 0.94 |
| 507 | N | 24.483 | 23.327 | 1.156 | | | 23.864 | 23.327 | 0.537 | | |
| | T | 25.065 | 23.808 | 1.257 | 0.101 | 0.93 | 23.962 | 23.808 | 0.154 | -0.383 | 1.3 |
| 509 | N | 23.263 | 22.033 | 1.23 | | | 22.674 | 22.033 | 0.641 | | |
| | T | 24.581 | 22.944 | 1.637 | 0.407 | 0.75 | 23.566 | 22.944 | 0.622 | -0.019 | 1.01 |
| 510 | N | 25.323 | 24.699 | 0.624 | | | 24.605 | 24.699 | -0.094 | | |
| | T | 24.437 | 24.33 | 0.107 | -0.517 | 1.43 | 24.198 | 24.33 | -0.132 | -0.038 | 1.03 |
| 511 | N | 25.274 | 23.903 | 1.371 | | | 23.602 | 23.903 | -0.301 | | |
| | T | 27.073 | 24.063 | 3.01 | 1.639 | 0.32 | 22.57 | 24.063 | -1.493 | -1.192 | 2.28 |
| 512 | N | 26.386 | 26.106 | 0.28 | | | 24.02 | 26.106 | -2.086 | | |
| | T | 25.204 | 23.404 | 1.8 | 1.52 | 0.35 | 23.718 | 23.404 | 0.314 | 2.4 | 0.19 |
| 513 | N | 23.019 | 22.522 | 0.497 | | | 23.815 | 22.522 | 1.293 | | |
| | T | 24.978 | 22.883 | 2.095 | 1.598 | 0.33 | 24.851 | 22.883 | 1.968 | 0.675 | 0.63 |
| 515 | N | 26.064 | 23.84 | 2.224 | | | 25.407 | 23.84 | 1.567 | | |
| | T | 23.54 | 21.506 | 2.034 | -0.19 | 1.14 | 24.596 | 21.506 | 3.09 | 1.523 | 0.35 |
| 516 | N | 22.712 | 21.053 | 1.659 | | | 23.256 | 21.053 | 2.203 | | |
| | T | 21.889 | 19.394 | 2.495 | 0.836 | 0.56 | 23.915 | 19.394 | 4.521 | 2.318 | 0.2 |
| 517 | N | 24.043 | 24.608 | -0.565 | | | 25.181 | 24.608 | 0.573 | | |
| | T | 23.621 | 25.987 | -2.366 | -1.801 | 3.48 | 25.257 | 25.987 | -0.73 | -1.303 | 2.47 |
| 518 | N | 22.814 | 20.725 | 2.089 | | | 24.253 | 20.725 | 3.528 | | |
| | T | 23.085 | 20.012 | 3.073 | 0.984 | 0.51 | 24.033 | 20.012 | 4.021 | 0.493 | 0.71 |
| 519 | N | 23.24 | 22.377 | 0.863 | | | 23.517 | 22.377 | 1.14 | | |
| | T | 23.155 | 22.307 | 0.848 | -0.015 | 1.01 | 24.689 | 22.307 | 2.382 | 1.242 | 0.42 |
| 599 | N | 25.485 | 26.933 | -1.448 | | | 24.06 | 26.933 | -2.873 | | |
| | T | 25.792 | 27.471 | -1.679 | -0.231 | 1.17 | 24.017 | 27.471 | -3.454 | -0.581 | 1.5 |
| 611 | N | 25.385 | 25.536 | -0.151 | | | 24.093 | 25.536 | -1.443 | | |
| | T | 26.784 | 27.192 | -0.408 | -0.257 | 1.19 | 25.403 | 27.192 | -1.789 | -0.346 | 1.27 |
| 628 | N | 27.113 | 26.821 | 0.292 | | | 24.45 | 26.821 | -2.371 | | |
| | T | 25.376 | 25.031 | 0.345 | 0.053 | 0.96 | 23.049 | 25.031 | -1.982 | 0.389 | 0.76 |

FIG. 2C

| Patient # | | miR-23b | | | | | miR-34b | | | | |
|---|---|---|---|---|---|---|---|---|---|---|---|
| | | Ct | Ct-cont | dCt | ddCt | F | Ct | Ct-cont | dCt | ddCt | F |
| 634 | N | 27.087 | 29.417 | -2.33 | | | 25.157 | 29.417 | -4.26 | | |
| | T | 27.77 | 30.016 | -2.246 | 0.084 | 0.94 | 24.81 | 30.016 | -5.206 | -0.946 | 1.93 |
| 635 | N | 26.203 | 26.076 | 0.127 | | | 25.001 | 26.076 | -1.075 | | |
| | T | 25.535 | 26.128 | -0.593 | -0.72 | 1.65 | 24.093 | 26.128 | -2.035 | -0.96 | 1.95 |
| 636 | N | 25.844 | 27.414 | -1.57 | | | 23.939 | 27.414 | -3.475 | | |
| | T | 26.782 | 27.217 | -0.435 | 1.135 | 0.46 | 23.768 | 27.217 | -3.449 | 0.026 | 0.98 |
| 595 | N | 26.297 | 25.823 | 0.474 | | | 24.614 | 25.823 | -1.209 | | |
| | T | 26.27 | 26.414 | -0.144 | -0.618 | 1.53 | 23.83 | 26.414 | -2.584 | -1.375 | 2.59 |
| 596 | N | 25.623 | 25.864 | -0.241 | | | 24.031 | 25.864 | -1.833 | | |
| | T | 25.707 | 26.214 | -0.507 | -0.266 | 1.2 | 24.528 | 26.214 | -1.686 | 0.147 | 0.9 |
| 603 | N | 25.672 | 27.315 | -1.643 | | | 24.047 | 27.315 | -3.268 | | |
| | T | 26.533 | 27.026 | -0.493 | 1.15 | 0.45 | 24.089 | 27.026 | -2.937 | 0.331 | 0.79 |
| 604 | N | 27.852 | 31.142 | -3.29 | | | 25.189 | 31.142 | -5.953 | | |
| | T | 29.569 | 31.071 | -1.502 | 1.788 | 0.29 | 24.847 | 31.071 | -6.224 | -0.271 | 1.21 |
| 609 | N | 26.16 | 28.357 | -2.197 | | | 25.352 | 28.357 | -3.005 | | |
| | T | 26.906 | 29.843 | -2.937 | -0.74 | 1.67 | 24.416 | 29.843 | -5.427 | -2.422 | 5.36 |
| 617 | N | 25.175 | 26.1 | -0.925 | | | 24.031 | 26.1 | -2.069 | | |
| | T | 31.837 | 33.118 | -1.281 | -0.356 | 1.28 | 29.484 | 33.118 | -3.634 | -1.565 | 2.96 |
| 520 | N | 23.08 | 21.3 | 1.78 | | | 23.431 | 21.3 | 2.131 | | |
| | T | 21.691 | 20.356 | 1.335 | -0.445 | 1.36 | 23.597 | 20.356 | 3.241 | 1.11 | 0.46 |
| 521 | N | 22.398 | 21.484 | 0.914 | | | 25.572 | 21.484 | 4.088 | | |
| | T | 25.613 | 19.59 | 6.023 | 5.109 | 0.03 | 25.192 | 19.59 | 5.602 | 1.514 | 0.35 |
| 524 | N | 23.085 | 21.507 | 1.578 | | | 26.04 | 21.507 | 4.533 | | |
| | T | 22.235 | 19.787 | 2.448 | 0.87 | 0.55 | 25.706 | 19.787 | 5.919 | 1.386 | 0.38 |
| 529 | N | 22.785 | 21.041 | 1.744 | | | 24.946 | 21.041 | 3.905 | | |
| | T | 23.185 | 21.402 | 1.783 | 0.039 | 0.97 | 25.058 | 21.402 | 3.656 | -0.249 | 1.19 |
| 563 | N | 24.242 | 24.17 | 0.072 | | | 24.801 | 24.17 | 0.631 | | |
| | T | 23.266 | 23.395 | -0.129 | -0.201 | 1.15 | 25.129 | 23.395 | 1.734 | 1.103 | 0.47 |
| 624 | N | 22.777 | 23.072 | -0.295 | | | 26.403 | 23.072 | 3.331 | | |
| | T | 24.045 | 21.714 | 2.331 | 2.626 | 0.16 | 26.69 | 21.714 | 4.976 | 1.645 | 0.32 |

FIG. 2C (Cont.)

| Patient # | | Ct-m | Ct-u | TIG1 meth dCt | ddCt | % | Ct-m | Ct-u | BNC1 meth dCt | ddCt | % |
|---|---|---|---|---|---|---|---|---|---|---|---|
| 506 | N | 34.937 | 21.662 | 13.275 | | | 30.437 | 21.118 | 9.319 | | |
| | T | 31.383 | 21.745 | 9.638 | -3.637 | 18.185 | 28.504 | 19.816 | 8.688 | -0.631 | 3.155 |
| 507 | N | 31.734 | 20.844 | 10.89 | | | 25.685 | 19.71 | 5.975 | | |
| | T | 30.295 | 20.704 | 9.591 | -1.299 | 6.495 | 28.105 | 19.826 | 8.279 | 2.304 | 0 |
| 509 | N | 25.008 | 18.421 | 6.587 | | | 26.475 | 17.765 | 8.71 | | |
| | T | 29.621 | 19.336 | 10.285 | 3.698 | 0 | 23.767 | 18.953 | 4.814 | -3.896 | 19.48 |
| 510 | N | 34.018 | 22.274 | 11.744 | | | 27.923 | 21.803 | 6.12 | | |
| | T | 33.729 | 22.124 | 11.605 | -0.139 | 0.695 | 28.312 | 19.403 | 8.909 | 2.789 | 0 |
| 511 | N | 33.773 | 21.313 | 12.46 | | | 29.366 | 20.049 | 9.317 | | |
| | T | 27.981 | 20.01 | 7.971 | -4.489 | 22.445 | 21.152 | 20.429 | 0.723 | -8.594 | 42.97 |
| 512 | N | 34.205 | 22.136 | 12.069 | | | 27.851 | 24.545 | 3.306 | | |
| | T | 31.863 | 18.518 | 13.345 | 1.276 | 0 | 24.342 | 18.427 | 5.915 | 2.609 | 0 |
| 513 | N | 33.914 | 19.606 | 14.308 | | | 26.781 | 19.276 | 7.505 | | |
| | T | 25.817 | 20.407 | 5.41 | -8.898 | 44.49 | 28.41 | 19.706 | 8.704 | 1.199 | 0 |
| 515 | N | 25.579 | 20.285 | 5.294 | | | 25.343 | 19.912 | 5.431 | | |
| | T | 30.776 | 19.835 | 10.941 | 5.647 | 0 | 24.365 | 19.537 | 4.828 | -0.603 | 3.015 |
| 516 | N | 29.317 | 18.692 | 10.625 | | | 25.131 | 17.564 | 7.567 | | |
| | T | 25.863 | 18.687 | 7.176 | -3.449 | 17.245 | 21.94 | 17.975 | 3.965 | -3.602 | 18.01 |
| 517 | N | 32.229 | 25.004 | 7.225 | | | 28.892 | 23.695 | 5.197 | | |
| | T | 34.855 | 22.74 | 12.115 | 4.89 | 0 | 25.385 | 22.106 | 3.279 | -1.918 | 9.59 |
| 518 | N | 24.511 | 19.716 | 4.795 | | | 23.553 | 17.711 | 5.842 | | |
| | T | 23.568 | 19.683 | 3.885 | -0.91 | 4.55 | 21.594 | 18.157 | 3.437 | -2.405 | 12.025 |
| 519 | N | 26.447 | 20.923 | 5.524 | | | 27.621 | 19.97 | 7.651 | | |
| | T | 30.546 | 20.174 | 10.372 | 4.848 | 0 | 25.436 | 18.969 | 6.467 | -1.184 | 5.92 |
| 599 | N | 34.288 | 24.417 | 9.871 | | | 31.532 | 22.6 | 8.932 | | |
| | T | 38.07 | 24.6 | 13.47 | 3.599 | 0 | 28.821 | 21.31 | 7.511 | -1.421 | 7.105 |
| 611 | N | 37.026 | 23.995 | 13.031 | | | 30.366 | 22.158 | 8.208 | | |
| | T | 33.736 | 21.751 | 11.985 | -1.046 | 5.23 | 28.731 | 19.784 | 8.947 | 0.739 | 0 |

FIG. 2D

| Patient # | | Ct-m | Ct-u | TIG1 meth dCt | ddCt | % | Ct-m | Ct-u | BNC1 meth dCt | ddCt | % |
|---|---|---|---|---|---|---|---|---|---|---|---|
| 628 | N | 33.968 | 22.258 | 11.71 | | | 29.874 | 20.314 | 9.56 | | |
| | T | 33.159 | 22.888 | 10.271 | -1.439 | 7.195 | 23.471 | 20.135 | 3.336 | -6.224 | 31.12 |
| 634 | N | 33.404 | 25.485 | 7.919 | | | 30.145 | 23.499 | 6.646 | | |
| | T | 31.531 | 23.196 | 8.335 | 0.416 | 0 | 30.696 | 22.841 | 7.855 | 1.209 | 0 |
| 635 | N | 25.42 | 21.825 | 3.595 | | | 25.341 | 20.09 | 5.251 | | |
| | T | 30.408 | 22.343 | 8.065 | 4.47 | 0 | 28.927 | 20.101 | 8.826 | 3.575 | 0 |
| 636 | N | 31.401 | 23.5 | 7.901 | | | 30.104 | 20.979 | 9.125 | | |
| | T | 31.617 | 22.863 | 8.754 | 0.853 | 0 | 26.94 | 20.822 | 6.118 | -3.007 | 15.035 |
| 595 | N | 32.114 | 21.424 | 10.69 | | | 27.654 | 19.075 | 8.579 | | |
| | T | 33.305 | 22.244 | 11.061 | 0.371 | 0 | 27.048 | 19.615 | 7.433 | -1.146 | 5.73 |
| 596 | N | 35.032 | 22.197 | 12.835 | | | 29.154 | 20.361 | 8.793 | | |
| | T | 31.349 | 22.609 | 8.74 | -4.095 | 20.475 | 24.93 | 21.14 | 3.79 | -5.003 | 25.015 |
| 603 | N | 31.624 | 21.714 | 9.91 | | | 29.185 | 20.422 | 8.763 | | |
| | T | 33.879 | 23.213 | 10.666 | 0.756 | 0 | 27.086 | 21.55 | 5.536 | -3.227 | 16.135 |
| 604 | N | 33.734 | 23.785 | 9.949 | | | 30.09 | 20.651 | 9.439 | | |
| | T | 31.371 | 24.275 | 7.096 | -2.853 | 14.265 | 23.967 | 21.768 | 2.199 | -7.24 | 36.2 |
| 609 | N | 33.507 | 25.548 | 7.959 | | | 28.769 | 20.375 | 8.394 | | |
| | T | 30.23 | 25.303 | 4.927 | -3.032 | 15.16 | 23.545 | 22.293 | 1.252 | -7.142 | 35.71 |
| 617 | N | 35.019 | 21.663 | 13.356 | | | 27.013 | 19.872 | 7.141 | | |
| | T | 29.122 | 22.473 | 6.649 | -6.707 | 33.535 | 27.359 | 20.118 | 7.241 | 0.1 | 0 |
| 520 | N | 28.632 | 18.93 | 9.702 | | | 26.677 | 17.727 | 8.95 | | |
| | T | 30.036 | 18.542 | 11.494 | 1.792 | 0 | 24.243 | 18.019 | 6.224 | -2.726 | 13.63 |

FIG. 2D (Cont. 1)

| Patient # | | Ct-m | Ct-u | TIG1 meth dCt | ddCt | % | Ct-m | Ct-u | BNC1 meth dCt | ddCt | % |
|---|---|---|---|---|---|---|---|---|---|---|---|
| 521 | N | 31.223 | 20.294 | 10.929 | | | 29.697 | 20.147 | 9.55 | | |
| | T | 31.093 | 21.505 | 9.588 | -1.341 | 6.705 | 28.442 | 20.406 | 8.036 | -1.514 | 7.57 |
| 524 | N | 25.855 | 20.118 | 5.737 | | | 27.272 | 18.732 | 8.54 | | |
| | T | 25.832 | 19.645 | 6.187 | 0.45 | 0 | 23.551 | 18.182 | 5.369 | -3.171 | 15.855 |
| 529 | N | 29.115 | 19.045 | 10.07 | | | 26.784 | 18.019 | 8.765 | | |
| | T | 30.159 | 21.846 | 8.313 | -1.757 | 8.785 | 26.135 | 19.047 | 7.088 | -1.677 | 8.385 |
| 563 | N | 33.031 | 22.385 | 10.646 | | | 30.191 | 21.371 | 8.82 | | |
| | T | 29.417 | 22.147 | 7.27 | -3.376 | 16.88 | 29.975 | 21.569 | 8.406 | -0.414 | 2.07 |
| 624 | N | 28.924 | 20.043 | 8.881 | | | 27.139 | 20.121 | 7.018 | | |
| | T | 29.006 | 19.199 | 9.807 | 0.926 | 0 | 22.317 | 18.356 | 3.961 | -3.057 | 15.285 |

FIG. 2D (Cont. 2)

| Patient # | | | | ZFAS1 | | |
|---|---|---|---|---|---|---|
| | | Ct | Ct-cont | dCt | ddCt | F |
| 506 | N | 36.28 | 32.577 | 3.703 | | |
| | T | 33.571 | 31.15 | 2.421 | -1.282 | 2.431759 |
| 507 | N | 34.746 | 30.22 | 4.526 | | |
| | T | 32.901 | 29.825 | 3.076 | -1.45 | 2.732081 |
| 509 | N | 33.333 | 29.338 | 3.995 | | |
| | T | 33.064 | 28.152 | 4.912 | 0.917 | 0.529609 |
| 510 | N | 45 | 33.269 | 11.731 | | |
| | T | 45 | 30.604 | 14.396 | 2.665 | 0.157672 |
| 511 | N | 39.748 | 31.925 | 7.823 | | |
| | T | 33.098 | 28.327 | 4.771 | -3.052 | 8.293609 |
| 512 | N | 40 | 32.648 | 7.352 | | |
| | T | 33.179 | 29.013 | 4.166 | -3.186 | 9.100842 |
| 513 | N | 40 | 31.306 | 8.694 | | |
| | T | 34.819 | 31.272 | 3.547 | -5.147 | 35.43247 |
| 515 | N | 40 | 32.494 | 7.506 | | |
| | T | 32.306 | 27.988 | 4.318 | -3.188 | 9.113467 |
| 516 | N | 35.507 | 29.552 | 5.955 | | |
| | T | 30.698 | 25.257 | 5.441 | -0.514 | 1.428004 |
| 517 | N | 41 | 31.566 | 9.434 | | |
| | T | 45 | 33.538 | 11.462 | 2.028 | 0.245195 |
| 518 | N | 32.892 | 29.169 | 3.723 | | |
| | T | 30.255 | 25.457 | 4.798 | 1.075 | 0.474671 |
| 519 | N | 35.86 | 30.341 | 5.519 | | |
| | T | 32.83 | 29.357 | 3.473 | -2.046 | 4.129594 |
| 599 | N | 45 | 37.281 | 7.719 | | |
| | T | 45 | 39.602 | 5.398 | -2.321 | 4.996785 |
| 611 | N | 45 | 34.461 | 10.539 | | |
| | T | 45 | 34.741 | 10.259 | -0.28 | 1.214195 |
| 628 | N | 46 | 38.268 | 7.732 | | |
| | T | 41 | 35.029 | 5.971 | -1.761 | 3.38933 |
| 634 | N | 45 | 36.165 | 8.835 | | |
| | T | 45 | 39.623 | 5.377 | -3.458 | 10.98909 |

FIG. 2E

| Patient # | | Ct | Ct-cont | ZFAS1 dCt | ddCt | F |
|---|---|---|---|---|---|---|
| 635 | N | 45 | 35.843 | 9.157 | | |
| | T | 45 | 38.019 | 6.981 | -2.176 | 4.518989 |
| 636 | N | 45 | 37.82 | 7.18 | | |
| | T | 45 | 36.16 | 8.84 | 1.66 | 0.316439 |
| 595 | N | 45 | 34.469 | 10.531 | | |
| | T | 39.855 | 33.039 | 6.816 | -3.715 | 13.13187 |
| 596 | N | 45 | 35.194 | 9.806 | | |
| | T | 39.868 | 34.741 | 5.127 | -4.679 | 25.61647 |
| 603 | N | 45 | 37.999 | 7.001 | | |
| | T | 37.993 | 35.137 | 2.856 | -4.145 | 17.69169 |
| 604 | N | 45 | 37.806 | 7.194 | | |
| | T | 45 | 38.601 | 6.399 | -0.795 | 1.735077 |
| 609 | N | 45 | 37.267 | 7.733 | | |
| | T | 45 | 38.371 | 6.629 | -1.104 | 2.149498 |
| 617 | N | 45 | 38.29 | 6.71 | | |
| | T | 45 | 35.408 | 9.592 | 2.882 | 0.135654 |
| 520 | N | 41 | 29.993 | 11.007 | | |
| | T | 31.961 | 25.849 | 6.112 | -4.895 | 29.75376 |
| 521 | N | 34.765 | 30.133 | 4.632 | | |
| | T | 35.173 | 28.644 | 6.529 | 1.897 | 0.268501 |
| 524 | N | 36.05 | 30.14 | 5.91 | | |
| | T | 29.321 | 25.25 | 4.071 | -1.839 | 3.57762 |
| 529 | N | 35.572 | 30.274 | 5.298 | | |
| | T | 31.729 | 27.991 | 3.738 | -1.56 | 2.948538 |
| 563 | N | 45 | 34.1 | 10.9 | | |
| | T | 45 | 32.095 | 12.905 | 2.005 | 0.249135 |
| 624 | N | 41 | 32.395 | 8.605 | | |
| | T | 31.029 | 27.255 | 3.774 | -4.831 | 28.46269 |

FIG. 2E (Cont.)

| \multicolumn{6}{c}{miR-96} |
|---|---|---|---|---|---|
| Patient ID | Ct | Ctc | dCt | ddCt | Fold |
| 375N | 30.491 | 23.938 | 6.553 | | |
| 375T | 31.143 | 23.83 | 7.313 | 0.76 | 0.590496 |
| 376N | 32.236 | 22.854 | 9.382 | | |
| 376T | 30.969 | 22.988 | 7.981 | -1.401 | 2.640846 |
| 377N | 34.062 | 25.873 | 8.189 | | |
| 377T | 32.338 | 25.132 | 7.206 | -0.983 | 1.976571 |
| 378N | 30.095 | 21.962 | 8.133 | | |
| 378T | 30.355 | 20.32 | 10.035 | 1.902 | 0.267572 |
| 379N | 34 | 26.085 | 7.915 | | |
| 379T | 30.492 | 22.927 | 7.565 | -0.35 | 1.274561 |
| 380N | 30.754 | 24.27 | 6.484 | | |
| 380T | 29.495 | 20.029 | 9.466 | 2.982 | 0.126569 |
| 381N | 31.719 | 24.415 | 7.304 | | |
| 381T | 32.01 | 24.941 | 7.069 | -0.235 | 1.176907 |
| 382N | 30.371 | 23.139 | 7.232 | | |
| 382T | 32.947 | 27.031 | 5.916 | -1.316 | 2.489748 |
| 383N | 33.302 | 25.45 | 7.852 | | |
| 383T | 31.648 | 25.093 | 6.555 | -1.297 | 2.457174 |
| 384N | 32.032 | 24.976 | 7.056 | | |
| 384T | 31.827 | 24.638 | 7.189 | 0.133 | 0.911933 |
| 387N | 30.317 | 24.938 | 5.379 | | |
| 387T | 31.674 | 25.294 | 6.38 | 1.001 | 0.499654 |
| 388N | 36.052 | 30.258 | 5.794 | | |
| 388T | 30.385 | 26.828 | 3.557 | -2.237 | 4.714158 |
| 389N | 31.938 | 26.652 | 5.286 | | |
| 389T | 30.868 | 25.251 | 5.617 | 0.331 | 0.794985 |
| 390N | 32.737 | 27.453 | 5.284 | | |
| 390T | 26.547 | 21.093 | 5.454 | 0.17 | 0.888843 |
| 391N | 30.577 | 26.584 | 3.993 | | |
| 391T | 29.298 | 25.338 | 3.96 | -0.033 | 1.023137 |
| 392N | 28.443 | 24.665 | 3.778 | | |
| 392T | 30.406 | 25.59 | 4.816 | 1.038 | 0.487002 |
| 393N | 30.36 | 25.634 | 4.726 | | |
| 393T | 28.599 | 22.297 | 6.302 | 1.576 | 0.335411 |
| 394N | 27.793 | 22.942 | 4.851 | | |
| 394T | 28.899 | 23.457 | 5.442 | 0.591 | 0.663883 |

FIG. 3

| Patient ID | Ct | Ctc | dCt | ddCt | Fold |
|---|---|---|---|---|---|
| | miR-96 | | | | |
| 395N | 29.826 | 23.346 | 6.48 | | |
| 395T | 32.199 | 25.652 | 6.547 | 0.067 | 0.954621 |
| 396N | 31.381 | 24.684 | 6.697 | | |
| 396T | 29.631 | 23.028 | 6.603 | -0.094 | 1.067325 |
| 397N | 32.571 | 26.011 | 6.56 | | |
| 397T | 36.538 | 27.584 | 8.954 | 2.394 | 0.190254 |
| 398N | 30.506 | 24.887 | 5.619 | | |
| 398T | 36.303 | 26.267 | 10.036 | 4.417 | 0.046811 |
| 399N | 34.574 | 27.599 | 6.975 | | |
| 399T | 29.096 | 23.474 | 5.622 | -1.353 | 2.554428 |
| 400N | 31.89 | 26.115 | 5.775 | | |
| 400T | 33.069 | 26.629 | 6.44 | 0.665 | 0.630689 |
| 401N | 33.304 | 25.331 | 7.973 | | |
| 401T | 30.847 | 24.311 | 6.536 | -1.437 | 2.707573 |
| 402N | 33.997 | 27.238 | 6.759 | | |
| 402T | 30.232 | 24.169 | 6.063 | -0.696 | 1.620007 |
| 403N | 33.154 | 35.804 | -2.65 | | |
| 403T | 29.688 | 31.456 | -1.768 | 0.882 | 0.542615 |
| 404N | 33.136 | 27.513 | 5.623 | | |
| 404T | 32.159 | 29.684 | 2.475 | -3.148 | 8.864259 |
| 405N | 32.537 | 26.499 | 6.038 | | |
| 405T | 31.455 | 24.074 | 7.381 | 1.343 | 0.3942 |
| 406N | 33.62 | 27.564 | 6.056 | | |
| 406T | 32.441 | 27.507 | 4.934 | -1.122 | 2.176485 |
| 407N | 33.247 | 28.361 | 4.886 | | |
| 407T | 33.024 | 29.033 | 3.991 | -0.895 | 1.85961 |
| 408N | 32.055 | 28.453 | 3.602 | | |
| 408T | 32.779 | 27.638 | 5.141 | 1.539 | 0.344124 |
| 409N | 32.092 | 27.734 | 4.358 | | |
| 409T | 29.162 | 22.954 | 6.208 | 1.85 | 0.277392 |
| 410N | 30.66 | 24.898 | 5.762 | | |
| 410T | 29.615 | 22.696 | 6.919 | 1.157 | 0.448444 |
| 411N | 33.599 | 29.583 | 4.016 | | |
| 411T | 31.836 | 26.729 | 5.107 | 1.091 | 0.469436 |
| 412N | 35.957 | 29.174 | 6.783 | | |
| 412T | 32.999 | 28.239 | 4.76 | -2.023 | 4.064281 |

FIG. 3 (Cont. 1)

| miR-96 | | | | | |
|---|---|---|---|---|---|
| Patient ID | Ct | Ctc | dCt | ddCt | Fold |
| 413N | 33.208 | 29.069 | 4.139 | | |
| 413T | 32.234 | 26.497 | 5.737 | 1.598 | 0.330335 |
| 414N | 33.637 | 26.826 | 6.811 | | |
| 414T | 33.948 | 25.561 | 8.387 | 1.576 | 0.335411 |
| 903N | 32.292 | 28.509 | 3.783 | | |
| 903T | 31.872 | 28.672 | 3.2 | -0.583 | 1.497961 |
| 904N | 31.997 | 27.961 | 4.036 | | |
| 904T | 31.129 | 25.816 | 5.313 | 1.277 | 0.412653 |
| 905N | 29.291 | 26.532 | 2.759 | | |
| 905T | 30.413 | 27.259 | 3.154 | 0.395 | 0.760489 |
| 906N | 29.941 | 26.245 | 3.696 | | |
| 906T | 30.812 | 26.809 | 4.003 | 0.307 | 0.808321 |
| 907N | 31.963 | 28.491 | 3.472 | | |
| 907T | 30.206 | 27.425 | 2.781 | -0.691 | 1.614402 |
| 908N | 31.274 | 27.217 | 4.057 | | |
| 908T | 27.595 | 22.476 | 5.119 | 1.062 | 0.478968 |
| 914N | 30.931 | 26.96 | 3.971 | | |
| 914T | 30.556 | 25.607 | 4.949 | 0.978 | 0.507683 |
| 920N | 30.432 | 28.428 | 2.004 | | |
| 920T | 28.619 | 25.269 | 3.35 | 1.346 | 0.393381 |
| 921N | 30.54 | 26.935 | 3.605 | | |
| 921T | 33.375 | 29.275 | 4.1 | 0.495 | 0.709562 |
| 922N | 34.33 | 30.57 | 3.76 | | |
| 922T | 30.254 | 27.516 | 2.738 | -1.022 | 2.030732 |
| 923N | 33.591 | 27.705 | 5.886 | | |
| 923T | 31.105 | 26.491 | 4.614 | -1.272 | 2.414961 |
| 925N | 29.293 | 28.219 | 1.074 | | |
| 925T | 31.655 | 28.961 | 2.694 | 1.62 | 0.325335 |
| 927N | 31.332 | 26.745 | 4.587 | | |
| 927T | 31.499 | 26.487 | 5.012 | 0.425 | 0.744839 |
| 928N | 28.462 | 25.539 | 2.923 | | |
| 928T | 28.197 | 25.25 | 2.947 | 0.024 | 0.983502 |
| 930N | 27.701 | 24.836 | 2.865 | | |
| 930T | 27.63 | 25.725 | 1.905 | -0.96 | 1.94531 |
| 934N | 30.829 | 26.524 | 4.305 | | |
| 934T | 28.862 | 23.701 | 5.161 | 0.856 | 0.552482 |

FIG. 3 (Cont. 2)

| | miR-96 | | | | |
|---|---|---|---|---|---|
| Patient ID | Ct | Ctc | dCt | ddCt | Fold |
| 936N | 31.509 | 27.923 | 3.586 | | |
| 936T | 27.698 | 28.59 | -0.892 | -4.478 | 22.28498 |
| 941N | 31.951 | 28.312 | 3.639 | | |
| 941T | 29.394 | 26.736 | 2.658 | -0.981 | 1.973833 |
| 946N | 29.77 | 25.261 | 4.509 | | |
| 946T | 29.364 | 23.726 | 5.638 | 1.129 | 0.457233 |
| 948N | 32.969 | 28.337 | 4.632 | | |
| 948T | 31.19 | 26.97 | 4.22 | -0.412 | 1.330529 |
| 950N | 30.403 | 24.977 | 5.426 | | |
| 950T | 32.734 | 26.941 | 5.793 | 0.367 | 0.775393 |
| 956N | 33.069 | 30.698 | 2.371 | | |
| 956T | 30.184 | 26.909 | 3.275 | 0.904 | 0.534403 |
| 958N | 30.399 | 28.509 | 1.89 | | |
| 958T | 30.13 | 26.841 | 3.289 | 1.399 | 0.379192 |
| 961N | 31.73 | 27.56 | 4.17 | | |
| 961T | 34.444 | 30.769 | 3.675 | -0.495 | 1.409321 |
| 962N | 32.601 | 26.002 | 6.599 | | |
| 962T | 35.961 | 29.66 | 6.301 | -0.298 | 1.229439 |
| 970N | 33.47 | 28.114 | 5.356 | | |
| 970T | 30.83 | 26.228 | 4.602 | -0.754 | 1.686462 |
| 971N | 32.86 | 27.74 | 5.12 | | |
| 971T | 30.003 | 25.332 | 4.671 | -0.449 | 1.365094 |
| 974N | 31.181 | 27.936 | 3.245 | | |
| 974T | 29.927 | 24.948 | 4.979 | 1.734 | 0.300617 |
| 975N | 30.794 | 26.349 | 4.445 | | |
| 975T | 29.754 | 25.674 | 4.08 | -0.365 | 1.287882 |
| 976N | 30.165 | 26.076 | 4.089 | | |
| 976T | 32.084 | 26.342 | 5.742 | 1.653 | 0.317978 |
| 992N | 36.975 | 33.888 | 3.087 | | |
| 992T | 32.842 | 31.897 | 0.945 | -2.142 | 4.413735 |
| 994N | 32.656 | 29.911 | 2.745 | | |
| 994T | 31.367 | 28.492 | 2.875 | 0.13 | 0.913831 |

FIG. 3 (Cont. 3)

|  | TWIST1 | | | | | CCND1 | | | | |
|---|---|---|---|---|---|---|---|---|---|---|
|  | Ct | Ctcon | dCt | ddCt | Fold | Ct | Ctcon | dCt | ddCt | Fold |
| 301N | 40 | 33.232 | 6.768 | | | 35.273 | 33.232 | 2.041 | | |
| 301T | 34.33 | 31.35 | 2.98 | -3.788 | 13.8 | 34.624 | 31.35 | 3.274 | 1.23 | 0.4 |
| 302N | 38.02 | 32.788 | 5.232 | | | 38 | 32.788 | 5.212 | | |
| 302T | 36.194 | 35.092 | 1.102 | -4.13 | 17.5 | 37.242 | 35.092 | 2.15 | -3.06 | 8.4 |
| 303N | 40 | 36.551 | 3.449 | | | 37.401 | 36.551 | 0.85 | | |
| 303T | 36.487 | 32.62 | 3.867 | 0.418 | 0.75 | 35.869 | 32.62 | 3.249 | 2.4 | 0.2 |
| 304N | 40 | 36.809 | 3.191 | | | 42 | 36.809 | 5.191 | | |
| 304T | 37.793 | 36.617 | 1.176 | -2.015 | 4.04 | 42 | 36.617 | 5.383 | 0.19 | 0.9 |
| 305N | 40 | 31.68 | 8.32 | | | 35.635 | 31.68 | 3.955 | | |
| 305T | 37.59 | 31.327 | 6.263 | -2.057 | 4.16 | 34.082 | 31.327 | 2.755 | -1.2 | 2.3 |
| 306N | 39.02 | 32.225 | 6.795 | | | 35.636 | 32.225 | 3.411 | | |
| 306T | 32.81 | 29.486 | 3.324 | -3.471 | 11.1 | 32.492 | 29.486 | 3.006 | -0.41 | 1.3 |
| 307N | 37.005 | 30.068 | 6.937 | | | 33.382 | 30.068 | 3.314 | | |
| 307T | 32.79 | 28.533 | 4.257 | -2.68 | 6.41 | 28.324 | 28.533 | -0.209 | -3.52 | 11 |
| 308N | 37.364 | 30.147 | 7.217 | | | 32.625 | 30.147 | 2.478 | | |
| 308T | 32.621 | 27.715 | 4.906 | -2.311 | 4.96 | 31.167 | 27.715 | 3.452 | 0.97 | 0.5 |
| 309N | 38.268 | 32.121 | 6.147 | | | 34.885 | 32.121 | 2.764 | | |
| 309T | 37.162 | 29.487 | 7.675 | 1.528 | 0.35 | 31.357 | 29.487 | 1.87 | -0.89 | 1.9 |
| 310N | 42 | 32.257 | 9.743 | | | 34.007 | 32.257 | 1.75 | | |
| 310T | 35.498 | 29.59 | 5.908 | -3.835 | 14.3 | 31.571 | 29.59 | 1.981 | 0.23 | 0.9 |

FIG. 4A

|      | TWIST1 | | | | | CCND1 | | | | |
|------|--------|---|---|---|---|-------|---|---|---|---|
|      | Ct | Ctcon | dCt | ddCt | Fold | Ct | Ctcon | dCt | ddCt | Fold |
| 311N | 38.152 | 29.434 | 8.718 | | | 32.752 | 29.434 | 3.318 | | |
| 311T | 33.667 | 28.256 | 5.411 | -3.307 | 9.9 | 32.194 | 28.256 | 3.938 | 0.62 | 0.7 |
| 312N | 37.146 | 31.506 | 5.64 | | | 34.518 | 31.506 | 3.012 | | |
| 312T | 34.245 | 30.704 | 3.541 | -2.099 | 4.28 | 33.263 | 30.704 | 2.559 | -0.45 | 1.4 |
| 313N | 37.735 | 34.119 | 3.616 | | | 36.529 | 34.119 | 2.41 | | |
| 313T | 36.023 | 30.196 | 5.827 | 2.211 | 0.22 | 32.723 | 30.196 | 2.527 | 0.12 | 0.9 |
| 314N | 36.075 | 29.745 | 6.33 | | | 33.199 | 29.745 | 3.454 | | |
| 314T | 34.115 | 29.395 | 4.72 | -1.61 | 3.05 | 31.689 | 29.395 | 2.294 | -1.16 | 2.2 |
| 315N | 40 | 30.511 | 9.489 | | | 33.355 | 30.511 | 2.844 | | |
| 315T | 31.059 | 28.871 | 2.188 | -7.301 | 158 | 30.629 | 28.871 | 1.758 | -1.09 | 2.1 |
| 316N | 36.639 | 31.676 | 4.963 | | | 34.543 | 31.676 | 2.867 | | |
| 316T | 34.916 | 30.329 | 4.587 | -0.376 | 1.3 | 32.356 | 30.329 | 2.027 | -0.84 | 1.8 |
| 317N | 42 | 30.378 | 11.622 | | | 33.574 | 30.378 | 3.196 | | |
| 317T | 33.37 | 28.294 | 5.076 | -6.546 | 93.4 | 30.538 | 28.294 | 2.244 | -0.95 | 1.9 |
| 318N | 36.359 | 29.421 | 6.938 | | | 32.309 | 29.421 | 2.888 | | |
| 318T | 33.662 | 26.732 | 6.93 | -0.008 | 1.01 | 29.177 | 26.732 | 2.445 | -0.44 | 1.4 |
| 319N | 37.144 | 29.814 | 7.33 | | | 33.846 | 29.814 | 4.032 | | |
| 319T | 34.762 | 28.487 | 6.275 | -1.055 | 2.08 | 31.474 | 28.487 | 2.987 | -1.04 | 2.1 |
| 320N | 37.093 | 29.214 | 7.879 | | | 32.926 | 29.214 | 3.712 | | |
| 320T | 36.424 | 26.735 | 9.689 | 1.81 | 0.29 | 29.803 | 26.735 | 3.068 | -0.64 | 1.6 |
| 321N | 38.74 | 28.552 | 10.188 | | | 31.569 | 28.552 | 3.017 | | |
| 321T | 32.792 | 26.062 | 6.73 | -3.458 | 11 | 29.139 | 26.062 | 3.077 | 0.06 | 1 |
| 322N | 36.476 | 28.455 | 8.021 | | | 31.797 | 28.455 | 3.342 | | |
| 322T | 29.418 | 24.533 | 4.885 | -3.136 | 8.79 | 27.198 | 24.533 | 2.665 | -0.68 | 1.6 |
| 323N | 36.494 | 29.817 | 6.677 | | | 32.466 | 29.817 | 2.649 | | |
| 323T | 32.952 | 28.452 | 4.5 | -2.177 | 4.52 | 29.57 | 28.452 | 1.118 | -1.53 | 2.9 |
| 324N | 37.023 | 31.236 | 5.787 | | | 34.029 | 31.236 | 2.793 | | |
| 324T | 32.622 | 29.336 | 3.286 | -2.501 | 5.66 | 31.839 | 29.336 | 2.503 | -0.29 | 1.2 |

FIG. 4A (Cont. 1)

|      | MET    |        |       |      |       | SOX4  |        |       |      |          |
|------|--------|--------|-------|------|-------|-------|--------|-------|------|----------|
|      | Ct     | Ctcon  | dCt   | ddCt | Fold  | Ct    | Ctcon  | dCt   | ddCt | Fold     |
| 301N | 36.06  | 33.232 | 2.828 |      |       | 33.12 | 33.23  | -0.12 |      |          |
| 301T | 34.042 | 31.35  | 2.692 | -0   | 1.099 | 31.48 | 31.35  | 0.125 | 0.2  | 0.845572 |
| 302N | 35.644 | 32.788 | 2.856 |      |       | 33.24 | 32.79  | 0.451 |      |          |
| 302T | 36.783 | 35.092 | 1.691 | -1   | 2.242 | 35.69 | 35.09  | 0.597 | 0.1  | 0.903753 |
| 303N | 43     | 36.551 | 6.449 |      |       | 38.4  | 36.55  | 1.844 |      |          |
| 303T | 37.963 | 32.62  | 5.343 | -1   | 2.152 | 33.52 | 32.62  | 0.9   | -1   | 1.923855 |
| 304N | 37.944 | 36.809 | 1.135 |      |       | 36.9  | 36.81  | 0.086 |      |          |
| 304T | 38.973 | 36.617 | 2.356 | 1.2  | 0.429 | 33.71 | 36.62  | -2.9  | -3   | 7.939235 |
| 305N | 35.263 | 31.68  | 3.583 |      |       | 33.15 | 31.68  | 1.465 |      |          |
| 305T | 34.976 | 31.327 | 3.649 | 0.1  | 0.955 | 31.16 | 31.33  | -0.17 | -2   | 3.105876 |
| 306N | 34.894 | 32.225 | 2.669 |      |       | 32.38 | 32.23  | 0.15  |      |          |
| 306T | 34.629 | 29.486 | 5.143 | 2.5  | 0.18  | 32.07 | 29.49  | 2.587 | 2.4  | 0.184667 |
| 307N | 34.441 | 30.068 | 4.373 |      |       | 31.08 | 30.07  | 1.009 |      |          |
| 307T | 32.057 | 28.533 | 3.524 | -1   | 1.801 | 28.58 | 28.53  | 0.051 | -1   | 1.942615 |
| 308N | 33.603 | 30.147 | 3.456 |      |       | 30.24 | 30.15  | 0.092 |      |          |
| 308T | 31.635 | 27.715 | 3.92  | 0.5  | 0.725 | 28.43 | 27.72  | 0.713 | 0.6  | 0.65022  |
| 309N | 36.388 | 32.121 | 4.267 |      |       | 33.19 | 32.12  | 1.066 |      |          |
| 309T | 31.74  | 29.487 | 2.253 | -2   | 4.039 | 29.06 | 29.49  | -0.43 | -1   | 2.812786 |
| 310N | 36.379 | 32.257 | 4.122 |      |       | 32.94 | 32.26  | 0.684 |      |          |
| 310T | 32.41  | 29.59  | 2.82  | -1   | 2.466 | 28.79 | 29.59  | -0.8  | -1   | 2.803055 |

FIG. 4A (Cont. 2)

|  | MET | | | | | SOX4 | | | | |
|---|---|---|---|---|---|---|---|---|---|---|
|  | Ct | Ctcon | dCt | ddCt | Fold | Ct | Ctcon | dCt | ddCt | Fold |
| 311N | 33.126 | 29.434 | 3.692 |  |  | 30.6 | 29.43 | 1.162 |  |  |
| 311T | 33.126 | 28.256 | 4.87 | 1.2 | 0.442 | 30.67 | 28.26 | 2.41 | 1.2 | 0.421031 |
| 312N | 37.272 | 31.506 | 5.766 |  |  | 32.31 | 31.51 | 0.805 |  |  |
| 312T | 36.537 | 30.704 | 5.833 | 0.1 | 0.955 | 31.42 | 30.7 | 0.712 | -0 | 1.066586 |
| 313N | 40.5 | 34.119 | 6.381 |  |  | 33.94 | 34.12 | -0.18 |  |  |
| 313T | 35.078 | 30.196 | 4.882 | -1 | 2.826 | 31.69 | 30.2 | 1.489 | 1.7 | 0.313601 |
| 314N | 33.495 | 29.745 | 3.75 |  |  | 31.15 | 29.75 | 1.404 |  |  |
| 314T | 33.676 | 29.395 | 4.281 | 0.5 | 0.692 | 30.34 | 29.4 | 0.94 | -0 | 1.379361 |
| 315N | 34.19 | 30.511 | 3.679 |  |  | 31.57 | 30.51 | 1.06 |  |  |
| 315T | 31.092 | 28.871 | 2.221 | -1 | 2.747 | 28.47 | 28.87 | -0.4 | -1 | 2.749177 |
| 316N | 35.777 | 31.676 | 4.101 |  |  | 32.61 | 31.68 | 0.933 |  |  |
| 316T | 34.092 | 30.329 | 3.763 | -0 | 1.264 | 31.39 | 30.33 | 1.06 | 0.1 | 0.915734 |
| 317N | 34.487 | 30.378 | 4.109 |  |  | 31.62 | 30.38 | 1.237 |  |  |
| 317T | 30.194 | 28.294 | 1.9 | -2 | 4.624 | 28.47 | 28.29 | 0.174 | -1 | 2.089272 |
| 318N | 33.158 | 29.421 | 3.737 |  |  | 29.65 | 29.42 | 0.23 |  |  |
| 318T | 31.141 | 26.732 | 4.409 | 0.7 | 0.628 | 28.34 | 26.73 | 1.607 | 1.4 | 0.385019 |
| 319N | 34.656 | 29.814 | 4.842 |  |  | 32.11 | 29.81 | 2.293 |  |  |
| 319T | 33.642 | 28.487 | 5.155 | 0.3 | 0.805 | 30.44 | 28.49 | 1.956 | -0 | 1.263127 |
| 320N | 33.895 | 29.214 | 4.681 |  |  | 30.82 | 29.21 | 1.607 |  |  |
| 320T | 28.93 | 26.735 | 2.195 | -2 | 5.602 | 28.17 | 26.74 | 1.434 | -0 | 1.1274 |
| 321N | 33.716 | 28.552 | 5.164 |  |  | 30.54 | 28.55 | 1.986 |  |  |
| 321T | 31.236 | 26.062 | 5.174 | 0 | 0.993 | 28.2 | 26.06 | 2.137 | 0.2 | 0.900626 |
| 322N | 33.844 | 28.455 | 5.389 |  |  | 30.59 | 28.46 | 2.136 |  |  |
| 322T | 28.636 | 24.533 | 4.103 | -1 | 2.439 | 26.6 | 24.53 | 2.062 | -0 | 1.052631 |
| 323N | 34.929 | 29.817 | 5.112 |  |  | 30.98 | 29.82 | 1.159 |  |  |
| 323T | 31.404 | 28.452 | 2.952 | -2 | 4.469 | 27.85 | 28.45 | -0.61 | -2 | 3.396385 |
| 324N | 35.178 | 31.236 | 3.942 |  |  | 32.93 | 31.24 | 1.693 |  |  |
| 324T | 31.886 | 29.336 | 2.55 | -1 | 2.624 | 30.12 | 29.34 | 0.782 | -1 | 1.880348 |

FIG. 4A (Cont. 3)

|  | miR-182 | | | | | miR-183 | | | | |
|---|---|---|---|---|---|---|---|---|---|---|
|  | Ct | Ctcon | dCt | ddCt | Fold | Ct | Ctcon | dCt | ddCt | Fold |
| 301N | 26.755 | 21.605 | 5.15 | | | 27.859 | 21.605 | 6.254 | | |
| 301T | 24.379 | 21.668 | 2.711 | -2.439 | 5.42266 | 25.725 | 21.668 | 4.057 | -2.197 | 4.5852 |
| 302N | 26.909 | 22.5 | 4.409 | | | 27.843 | 22.5 | 5.343 | | |
| 302T | 26.441 | 23.953 | 2.488 | -1.921 | 3.78685 | 27.23 | 23.953 | 3.277 | -2.066 | 4.1872 |
| 303N | 29.439 | 26.199 | 3.24 | | | 30.331 | 26.199 | 4.132 | | |
| 303T | 26.194 | 24.195 | 1.999 | -1.241 | 2.36362 | 26.753 | 24.195 | 2.558 | -1.574 | 2.9773 |
| 304N | 28.4 | 24.292 | 4.108 | | | 29.345 | 24.292 | 5.053 | | |
| 304T | 26.499 | 24.435 | 2.064 | -2.044 | 4.12387 | 26.794 | 24.435 | 2.359 | -2.694 | 6.4711 |
| 305N | 27.354 | 21.938 | 5.416 | | | 28.612 | 21.938 | 6.674 | | |
| 305T | 25.199 | 21.193 | 4.006 | -1.41 | 2.65737 | 26.241 | 21.193 | 5.048 | -1.626 | 3.0866 |
| 306N | 27.534 | 22.036 | 5.498 | | | 28.532 | 22.036 | 6.496 | | |
| 306T | 25.406 | 21.737 | 3.669 | -1.829 | 3.55291 | 26.254 | 21.737 | 4.517 | -1.979 | 3.9422 |
| 307N | 26.901 | 21.27 | 5.631 | | | 28.067 | 21.27 | 6.797 | | |
| 307T | 25.157 | 18.938 | 6.219 | 0.588 | 0.66526 | 26.249 | 18.938 | 7.311 | 0.514 | 0.7003 |
| 308N | 26.438 | 20.235 | 6.203 | | | 27.749 | 20.235 | 7.514 | | |
| 308T | 23.525 | 19.33 | 4.195 | -2.008 | 4.02224 | 24.802 | 19.33 | 5.472 | -2.042 | 4.1182 |
| 309N | 26.996 | 22.532 | 4.464 | | | 28.156 | 22.532 | 5.624 | | |
| 309T | 24.182 | 20.711 | 3.471 | -0.993 | 1.99032 | 24.939 | 20.711 | 4.228 | -1.396 | 2.6317 |
| 310N | 27.806 | 22.298 | 5.508 | | | 28.969 | 22.298 | 6.671 | | |
| 310T | 24.493 | 20.624 | 3.869 | -1.639 | 3.1145 | 25.338 | 20.624 | 4.714 | -1.957 | 3.8825 |

FIG. 4B

|      | miR-182 |        |      |       |         | miR-183 |        |       |        |        |
|------|---------|--------|------|-------|---------|---------|--------|-------|--------|--------|
|      | Ct      | Ctcon  | dCt  | ddCt  | Fold    | Ct      | Ctcon  | dCt   | ddCt   | Fold   |
| 311N | 26.086  | 20.654 | 5.432|       |         | 27.711  | 20.654 | 7.057 |        |        |
| 311T | 26.186  | 21.624 | 4.562| -0.87 | 1.82766 | 27.344  | 21.624 | 5.72  | -1.337 | 2.5263 |
| 312N | 26.98   | 21.649 | 5.331|       |         | 28.012  | 21.649 | 6.363 |        |        |
| 312T | 27.263  | 21.093 | 6.17 | 0.839 | 0.55903 | 28.163  | 21.093 | 7.07  | 0.707  | 0.6126 |
| 313N | 27.187  | 22.39  | 4.797|       |         | 28.211  | 22.39  | 5.821 |        |        |
| 313T | 25.582  | 21.388 | 4.194| -0.603| 1.51887 | 27.006  | 21.388 | 5.618 | -0.203 | 1.1511 |
| 314N | 26.598  | 20.352 | 6.246|       |         | 28.05   | 20.352 | 7.698 |        |        |
| 314T | 24.67   | 19.689 | 4.981| -1.265| 2.40327 | 26.172  | 19.689 | 6.483 | -1.215 | 2.3214 |
| 315N | 26.646  | 21.023 | 5.623|       |         | 28.026  | 21.023 | 7.003 |        |        |
| 315T | 24.603  | 19.431 | 5.172| -0.451| 1.36699 | 25.157  | 19.431 | 5.726 | -1.277 | 2.4233 |
| 316N | 27.221  | 20.984 | 6.237|       |         | 27.82   | 20.984 | 6.836 |        |        |
| 316T | 24.814  | 20.707 | 4.107| -2.13 | 4.37717 | 26.597  | 20.707 | 5.89  | -0.946 | 1.9265 |
| 317N | 27.15   | 21.601 | 5.549|       |         | 28.445  | 21.601 | 6.844 |        |        |
| 317T | 24.817  | 19.486 | 5.331| -0.218| 1.16312 | 26.127  | 19.486 | 6.641 | -0.203 | 1.1511 |
| 318N | 25.976  | 20.238 | 5.738|       |         | 27.665  | 20.238 | 7.427 |        |        |
| 318T | 24.056  | 19.958 | 4.098| -1.64 | 3.11666 | 25.353  | 19.958 | 5.395 | -2.032 | 4.0897 |
| 319N | 27.216  | 21.036 | 6.18 |       |         | 28.481  | 21.036 | 7.445 |        |        |
| 319T | 25.624  | 21.229 | 4.395| -1.785| 3.44618 | 27.072  | 21.229 | 5.843 | -1.602 | 3.0356 |
| 320N | 26.856  | 20.812 | 6.044|       |         | 28.183  | 20.812 | 7.371 |        |        |
| 320T | 23.626  | 19.095 | 4.531| -1.513| 2.85403 | 25.578  | 19.095 | 6.483 | -0.888 | 1.8506 |
| 321N | 26.285  | 20.128 | 6.157|       |         | 28.03   | 20.128 | 7.902 |        |        |
| 321T | 24.893  | 19.909 | 4.984| -1.173| 2.2548  | 26.402  | 19.909 | 6.493 | -1.409 | 2.6555 |
| 322N | 26.872  | 20.068 | 6.804|       |         | 28.411  | 20.068 | 8.343 |        |        |
| 322T | 24.176  | 18.357 | 5.819| -0.985| 1.97931 | 25.184  | 18.357 | 6.827 | -1.516 | 2.86   |
| 323N | 28.013  | 20.811 | 7.202|       |         | 28.987  | 20.811 | 8.176 |        |        |
| 323T | 24.439  | 18.999 | 5.44 | -1.762| 3.39168 | 25.291  | 18.999 | 6.292 | -1.884 | 3.691  |
| 324N | 28.306  | 21.709 | 6.597|       |         | 29.198  | 21.709 | 7.489 |        |        |
| 324T | 25.464  | 20.576 | 4.888| -1.709| 3.26934 | 26.919  | 20.576 | 6.343 | -1.146 | 2.213  |

FIG. 4B (Cont. 1)

|      | miR-210 | | | | | miR-21 | | | | |
|------|--------|--------|--------|--------|--------|--------|--------|--------|--------|--------|
|      | Ct | Ctcon | dCt | ddCt | Fold | Ct | Ctcon | dCt | ddCt | Fold |
| 301N | 21.772 | 21.605 | 0.167 | | | 17.537 | 21.605 | -4.068 | | |
| 301T | 20.794 | 21.668 | -0.874 | -1.041 | 2.0577 | 16.497 | 21.668 | -5.171 | -1.103 | 2.148009 |
| 302N | 21.421 | 22.5 | -1.079 | | | 17.881 | 22.5 | -4.619 | | |
| 302T | 20.62 | 23.953 | -3.333 | -2.254 | 4.77 | 17.391 | 23.953 | -6.562 | -1.943 | 3.845044 |
| 303N | 23.847 | 26.199 | -2.352 | | | 19.279 | 26.199 | -6.92 | | |
| 303T | 21.192 | 24.195 | -3.003 | -0.651 | 1.5703 | 17.425 | 24.195 | -6.77 | 0.15 | 0.90125 |
| 304N | 22.923 | 24.292 | -1.369 | | | 18.098 | 24.292 | -6.194 | | |
| 304T | 22.964 | 24.435 | -1.471 | -0.102 | 1.0733 | 18.336 | 24.435 | -6.099 | 0.095 | 0.936272 |
| 305N | 22.717 | 21.938 | 0.779 | | | 17.605 | 21.938 | -4.333 | | |
| 305T | 22.559 | 21.193 | 1.366 | 0.587 | 0.6657 | 17.012 | 21.193 | -4.181 | 0.152 | 0.900002 |
| 306N | 22.114 | 22.036 | 0.078 | | | 17.523 | 22.036 | -4.513 | | |
| 306T | 21.28 | 21.737 | -0.457 | -0.535 | 1.4489 | 16.236 | 21.737 | -5.501 | -0.988 | 1.983433 |
| 307N | 22.287 | 21.27 | 1.017 | | | 18.183 | 21.27 | -3.087 | | |
| 307T | 19.657 | 18.938 | 0.719 | -0.298 | 1.2294 | 15.475 | 18.938 | -3.463 | -0.376 | 1.297739 |
| 308N | 21.069 | 20.235 | 0.834 | | | 17.171 | 20.235 | -3.064 | | |
| 308T | 19.532 | 19.33 | 0.202 | -0.632 | 1.5497 | 15.662 | 19.33 | -3.668 | -0.604 | 1.519925 |
| 309N | 22.182 | 22.532 | -0.35 | | | 17.745 | 22.532 | -4.787 | | |
| 309T | 20.65 | 20.711 | -0.061 | 0.289 | 0.8185 | 17.084 | 20.711 | -3.627 | 1.16 | 0.447513 |
| 310N | 22.181 | 22.298 | -0.117 | | | 17.765 | 22.298 | -4.533 | | |
| 310T | 20.674 | 20.624 | 0.05 | 0.167 | 0.8907 | 15.859 | 20.624 | -4.765 | -0.232 | 1.174462 |

FIG. 4B (Cont. 2)

|      | miR-210 |        |        |        |        | miR-21 |        |        |        |          |
|------|---------|--------|--------|--------|--------|--------|--------|--------|--------|----------|
|      | Ct      | Ctcon  | dCt    | ddCt   | Fold   | Ct     | Ctcon  | dCt    | ddCt   | Fold     |
| 311N | 20.58   | 20.654 | -0.074 |        |        | 17.019 | 20.654 | -3.635 |        |          |
| 311T | 22.333  | 21.624 | 0.709  | 0.783  | 0.5812 | 17.186 | 21.624 | -4.438 | -0.803 | 1.744725 |
| 312N | 22.378  | 21.649 | 0.729  |        |        | 17.124 | 21.649 | -4.525 |        |          |
| 312T | 22.485  | 21.093 | 1.392  | 0.663  | 0.6316 | 15.84  | 21.093 | -5.253 | -0.728 | 1.656341 |
| 313N | 22.609  | 22.39  | 0.219  |        |        | 18.527 | 22.39  | -3.863 |        |          |
| 313T | 20.088  | 21.388 | -1.3   | -1.519 | 2.8659 | 17.296 | 21.388 | -4.092 | -0.229 | 1.172022 |
| 314N | 21.138  | 20.352 | 0.786  |        |        | 17.973 | 20.352 | -2.379 |        |          |
| 314T | 21.081  | 19.689 | 1.392  | 0.606  | 0.657  | 15.669 | 19.689 | -4.02  | -1.641 | 3.118819 |
| 315N | 21.442  | 21.023 | 0.419  |        |        | 17.58  | 21.023 | -3.443 |        |          |
| 315T | 20.861  | 19.431 | 1.43   | 1.011  | 0.4962 | 15.242 | 19.431 | -4.189 | -0.746 | 1.677136 |
| 316N | 21.962  | 20.984 | 0.978  |        |        | 17.391 | 20.984 | -3.593 |        |          |
| 316T | 21.781  | 20.707 | 1.074  | 0.096  | 0.9356 | 16.9   | 20.707 | -3.807 | -0.214 | 1.1599   |
| 317N | 21.706  | 21.601 | 0.105  |        |        | 18.068 | 21.601 | -3.533 |        |          |
| 317T | 20.245  | 19.486 | 0.759  | 0.654  | 0.6355 | 16.193 | 19.486 | -3.293 | 0.24   | 0.846745 |
| 318N | 20.835  | 20.238 | 0.597  |        |        | 17.073 | 20.238 | -3.165 |        |          |
| 318T | 19.11   | 19.958 | -0.848 | -1.445 | 2.7226 | 16.039 | 19.958 | -3.919 | -0.754 | 1.686462 |
| 319N | 20.829  | 21.036 | -0.207 |        |        | 18.001 | 21.036 | -3.035 |        |          |
| 319T | 21.5    | 21.229 | 0.271  | 0.478  | 0.718  | 16.79  | 21.229 | -4.439 | -1.404 | 2.646343 |
| 320N | 22.112  | 20.812 | 1.3    |        |        | 18.828 | 20.812 | -1.984 |        |          |
| 320T | 22.248  | 19.095 | 3.153  | 1.853  | 0.2768 | 17.032 | 19.095 | -2.063 | -0.079 | 1.056286 |
| 321N | 21.901  | 20.128 | 1.773  |        |        | 18.028 | 20.128 | -2.1   |        |          |
| 321T | 20.872  | 19.909 | 0.963  | -0.81  | 1.7532 | 17.513 | 19.909 | -2.396 | -0.296 | 1.227736 |
| 322N | 21.763  | 20.068 | 1.695  |        |        | 18.11  | 20.068 | -1.958 |        |          |
| 322T | 19.16   | 18.357 | 0.803  | -0.892 | 1.8557 | 16.348 | 18.357 | -2.009 | -0.051 | 1.035983 |
| 323N | 23.235  | 20.811 | 2.424  |        |        | 18.386 | 20.811 | -2.425 |        |          |
| 323T | 19.986  | 18.999 | 0.987  | -1.437 | 2.7076 | 16.907 | 18.999 | -2.092 | 0.333  | 0.793884 |
| 324N | 22.522  | 21.709 | 0.813  |        |        | 19.074 | 21.709 | -2.635 |        |          |
| 324T | 20.499  | 20.576 | -0.077 | -0.89  | 1.8532 | 17.039 | 20.576 | -3.537 | -0.902 | 1.868655 |

FIG. 4B (Cont. 3)

|  | OSMR | | | | | SFRP1 | | | | |
|---|---|---|---|---|---|---|---|---|---|---|
|  | Ctm | Ctu | dCt | dCt-4 | % | Ctm | Ctu | dCt | ddCt | % |
| 301N | 34.035 | 20.45 | 13.585 | 9.585 | 0 | 28.899 | 22.29 | 6.609 | | |
| 301T | 21.199 | 26.384 | -5.185 | -9.185 | 91.85 | 28.297 | 23.986 | 4.311 | -2.298 | 11.49 |
| 302N | 28.166 | 24.183 | 3.983 | -0.017 | 0.17 | 28.904 | 23.257 | 5.647 | | |
| 302T | 31.039 | 25.486 | 5.553 | 1.553 | 0 | 28.716 | 24.053 | 4.663 | -0.984 | 4.92 |
| 303N | 32.667 | 27.353 | 5.314 | 1.314 | 0 | 27.833 | 23.254 | 4.579 | | |
| 303T | 33.779 | 25.233 | 8.546 | 4.546 | 0 | 23.125 | 22.221 | 0.904 | -3.675 | 18.375 |
| 304N | 34.018 | 27.994 | 6.024 | 2.024 | 0 | 27.367 | 24.276 | 3.091 | | |
| 304T | 33.238 | 28.312 | 4.926 | 0.926 | 0 | 27.379 | 23.285 | 4.094 | 1.003 | 0 |
| 305N | 33.95 | 26.893 | 7.057 | 3.057 | 0 | 30.236 | 24.447 | 5.789 | | |
| 305T | 21.592 | 22.046 | -0.454 | -4.454 | 44.54 | 22.674 | 23.329 | -0.655 | -6.444 | 32.22 |
| 306N | 28.123 | 20.691 | 7.432 | 3.432 | 0 | 26.843 | 21.49 | 5.353 | | |
| 306T | 20.303 | 22.052 | -1.749 | -5.749 | 57.49 | 21.681 | 20.638 | 1.043 | -4.31 | 21.55 |
| 307N | 31.967 | 21.135 | 10.832 | 6.832 | 0 | 26.972 | 21.587 | 5.385 | | |
| 307T | 17.374 | 19.329 | -1.955 | -5.955 | 59.55 | 21.393 | 20.661 | 0.732 | -4.653 | 23.265 |
| 308N | 19.697 | 17.389 | 2.308 | -1.692 | 16.92 | 21.914 | 18.606 | 3.308 | | |
| 308T | 16.864 | 18.654 | -1.79 | -5.79 | 57.9 | 19.895 | 20.223 | -0.328 | -3.636 | 18.18 |
| 309N | 23.038 | 25.04 | -2.002 | -6.002 | 60.02 | 25.664 | 22.871 | 2.793 | | |
| 309T | 18.342 | 21.685 | -3.343 | -7.343 | 73.43 | 21.442 | 22.791 | -1.349 | -4.142 | 20.71 |
| 310N | 25.062 | 22.232 | 2.83 | -1.17 | 11.7 | 26.001 | 22.284 | 3.717 | | |
| 310T | 18.554 | 20.974 | -2.42 | -6.42 | 64.2 | 20.944 | 21.35 | -0.406 | -4.123 | 20.615 |
| 311N | 25.464 | 19.841 | 5.623 | 1.623 | 0 | 23.288 | 20.421 | 2.867 | | |
| 311T | 19.232 | 20.207 | -0.975 | -4.975 | 49.75 | 21.575 | 20.469 | 1.106 | -1.761 | 8.805 |
| 312N | 25.089 | 20.447 | 4.642 | 0.642 | 0 | 25.617 | 21.883 | 3.734 | | |
| 312T | 20.33 | 22.135 | -1.805 | -5.805 | 58.05 | 23.502 | 22.107 | 1.395 | -2.339 | 11.695 |

FIG. 4C

|      | OSMR |  |  |  |  | SFRP1 |  |  |  |  |
|------|------|------|------|------|------|------|------|------|------|------|
|      | Ctm | Ctu | dCt | dCt-4 | % | Ctm | Ctu | dCt | ddCt | % |
| 313N | 34.11 | 22.944 | 11.166 | 7.166 | 0 | 26.055 | 23.758 | 2.297 |  |  |
| 313T | 20.471 | 19.315 | 1.156 | -2.844 | 28.44 | 21.295 | 21.538 | -0.243 | -2.54 | 12.7 |
| 314N | 21.408 | 20.226 | 1.182 | -2.818 | 28.18 | 25.157 | 21.825 | 3.332 |  |  |
| 314T | 18.659 | 20.012 | -1.353 | -5.353 | 53.53 | 20.553 | 20.464 | 0.089 | -3.243 | 16.215 |
| 315N | 20.737 | 19.235 | 1.502 | -2.498 | 24.98 | 23.789 | 20.226 | 3.563 |  |  |
| 315T | 19.309 | 20.505 | -1.196 | -5.196 | 51.96 | 22.202 | 21.277 | 0.925 | -2.638 | 13.19 |
| 316N | 26.225 | 19.64 | 6.585 | 2.585 | 0 | 25.17 | 20.327 | 4.843 |  |  |
| 316T | 28.936 | 26.033 | 2.903 | -1.097 | 10.97 | 23.677 | 23.278 | 0.399 | -4.444 | 22.22 |
| 317N | 31.956 | 19.175 | 12.781 | 8.781 | 0 | 25.357 | 21.004 | 4.353 |  |  |
| 317T | 18.542 | 19.515 | -0.973 | -4.973 | 49.73 | 19.904 | 20.078 | -0.174 | -4.527 | 22.635 |
| 318N | 23.889 | 19.105 | 4.784 | 0.784 | 0 | 23.188 | 20.587 | 2.601 |  |  |
| 318T | 18.314 | 18.801 | -0.487 | -4.487 | 44.87 | 21.139 | 20.461 | 0.678 | -1.923 | 9.615 |
| 319N | 24.066 | 21.219 | 2.847 | -1.153 | 11.53 | 24.382 | 21.05 | 3.332 |  |  |
| 319T | 19.914 | 19.531 | 0.383 | -3.617 | 36.17 | 22.829 | 21.165 | 1.664 | -1.668 | 8.34 |
| 320N | 21.51 | 19.91 | 1.6 | -2.4 | 24 | 23.837 | 20.958 | 2.879 |  |  |
| 320T | 17.965 | 18.638 | -0.673 | -4.673 | 46.73 | 20.757 | 20.419 | 0.338 | -2.541 | 12.705 |
| 321N | 20.07 | 18.672 | 1.398 | -2.602 | 26.02 | 23.277 | 20.478 | 2.799 |  |  |
| 321T | 17.975 | 20.045 | -2.07 | -6.07 | 60.7 | 21.134 | 20.065 | 1.069 | -1.73 | 8.65 |
| 322N | 24.474 | 22.826 | 1.648 | -2.352 | 23.52 | 24.273 | 21.684 | 2.589 |  |  |
| 322T | 17.184 | 16.955 | 0.229 | -3.771 | 37.71 | 20.249 | 18.08 | 2.169 | -0.42 | 2.1 |
| 323N | 23.568 | 22.388 | 1.18 | -2.82 | 28.2 | 24.042 | 22.56 | 1.482 |  |  |
| 323T | 19.422 | 18.735 | 0.687 | -3.313 | 33.13 | 22.486 | 21.362 | 1.124 | -0.358 | 1.79 |
| 324N | 21.173 | 20.883 | 0.29 | -3.71 | 37.1 | 24.739 | 21.717 | 3.022 |  |  |
| 324T | 20.141 | 21.3 | -1.159 | -5.159 | 51.59 | 22.986 | 23.344 | -0.358 | -3.38 | 16.9 |

FIG. 4C (Cont. 1)

| MGMT | | | | | TIMP3 | | | | |
|---|---|---|---|---|---|---|---|---|---|
| Ctm | Ctu | dCt | ddCt | % | Ctm | Ctu | dCt | ddCt | % |
| 29.763 | 20.189 | 9.574 | | | 29.082 | 22.477 | 6.605 | | |
| 29.704 | 22.386 | 7.318 | -2.256 | 11.28 | 23.702 | 21.907 | 1.795 | -4.81 | 24.05 |
| 29.332 | 21.407 | 7.925 | | | 28.363 | 23.541 | 4.822 | | |
| 25.343 | 22.33 | 3.013 | -4.912 | 24.56 | 29.406 | 23.261 | 6.145 | 1.323 | 0 |
| 29.988 | 22.344 | 7.644 | | | 28.881 | 22.754 | 6.127 | | |
| 25.065 | 20.581 | 4.484 | -3.16 | 15.8 | 24.687 | 22.189 | 2.498 | -3.629 | 18.145 |
| 29.735 | 22.222 | 7.513 | | | 28.449 | 23.276 | 5.173 | | |
| 30.136 | 21.805 | 8.331 | 0.818 | 0 | 28.771 | 23.174 | 5.597 | 0.424 | 0 |
| 30.249 | 21.484 | 8.765 | | | 29.374 | 23.157 | 6.217 | | |
| 21.733 | 19.973 | 1.76 | -7.005 | 35.025 | 29.782 | 21.346 | 8.436 | 2.219 | 0 |
| 27.072 | 18.818 | 8.254 | | | 28.952 | 20.89 | 8.062 | | |
| 26.613 | 18.647 | 7.966 | -0.288 | 1.44 | 22.348 | 21.692 | 0.656 | -7.406 | 37.03 |
| 29.448 | 18.026 | 11.422 | | | 28.874 | 20.972 | 7.902 | | |
| 28.882 | 16.683 | 12.199 | 0.777 | 0 | 28.564 | 18.619 | 9.945 | 2.043 | 0 |
| 19.21 | 16.518 | 2.692 | | | 23.991 | 18.687 | 5.304 | | |
| 24.372 | 16.728 | 7.644 | 4.952 | 0 | 27.675 | 18.238 | 9.437 | 4.133 | 0 |
| 28.267 | 21.531 | 6.736 | | | 28.796 | 22.837 | 5.959 | | |
| 17.85 | 22.614 | -4.764 | -11.5 | 57.5 | 28.723 | 20.441 | 8.282 | 2.323 | 0 |
| 24.319 | 20.085 | 4.234 | | | 29.032 | 22.51 | 6.522 | | |
| 20.31 | 18.906 | 1.404 | -2.83 | 14.15 | 27.049 | 21.169 | 5.88 | -0.642 | 3.21 |
| 21.462 | 17.449 | 4.013 | | | 27.673 | 19.714 | 7.959 | | |
| 18.513 | 19.003 | -0.49 | -4.503 | 22.515 | 22.344 | 21.016 | 1.328 | -6.631 | 33.155 |
| 24.028 | 18.895 | 5.133 | | | 27.709 | 21.044 | 6.665 | | |
| 27.399 | 22.187 | 5.212 | 0.079 | 0 | 28.503 | 22.1 | 6.403 | -0.262 | 1.31 |

FIG. 4C (Cont. 2)

| MGMT | | | | | TIMP3 | | | | |
|---|---|---|---|---|---|---|---|---|---|
| Ctm | Ctu | dCt | ddCt | % | Ctm | Ctu | dCt | ddCt | % |
| 30.012 | 20.179 | 9.833 | | | 28.65 | 22.312 | 6.338 | | |
| 29.189 | 18.756 | 10.433 | 0.6 | 0 | 24.837 | 21.445 | 3.392 | -2.946 | 14.73 |
| 29.096 | 19.69 | 9.406 | | | 28.529 | 21.574 | 6.955 | | |
| 17.578 | 19.28 | -1.702 | -11.108 | 55.54 | 20.21 | 21.28 | -1.07 | -8.025 | 40.125 |
| 20.218 | 17.679 | 2.539 | | | 26.411 | 19.862 | 6.549 | | |
| 19.584 | 19.951 | -0.367 | -2.906 | 14.53 | 29.197 | 20.228 | 8.969 | 2.42 | 0 |
| 26.082 | 18.586 | 7.496 | | | 28.876 | 21.043 | 7.833 | | |
| 20.021 | 24.128 | -4.107 | -11.603 | 58.015 | 25.914 | 23.603 | 2.311 | -5.522 | 27.61 |
| 25.755 | 18.791 | 6.964 | | | 28.463 | 20.661 | 7.802 | | |
| 27.959 | 17.688 | 10.271 | 3.307 | 0 | 28.455 | 19.386 | 9.069 | 1.267 | 0 |
| 26.998 | 17.403 | 9.595 | | | 27.735 | 20.14 | 7.595 | | |
| 17.946 | 17.933 | 0.013 | -9.582 | 47.91 | 28.115 | 19.449 | 8.666 | 1.071 | 0 |
| 28.664 | 18.305 | 10.359 | | | 28.745 | 20.56 | 8.185 | | |
| 17.585 | 18.451 | -0.866 | -11.225 | 56.125 | 22.58 | 20.338 | 2.242 | -5.943 | 29.715 |
| 23.477 | 17.746 | 5.731 | | | 28.022 | 20.275 | 7.747 | | |
| 17.179 | 19.383 | -2.204 | -7.935 | 39.675 | 24.365 | 19.128 | 5.237 | -2.51 | 12.55 |
| 20.241 | 17.668 | 2.573 | | | 24.784 | 19.737 | 5.047 | | |
| 17.605 | 18.245 | -0.64 | -3.213 | 16.065 | 28.04 | 19.094 | 8.946 | 3.899 | 0 |
| 24.168 | 20.263 | 3.905 | | | 28.671 | 21.084 | 7.587 | | |
| 17.722 | 16.553 | 1.169 | -2.736 | 13.68 | 20.018 | 18.181 | 1.837 | -5.75 | 28.75 |
| 20.69 | 19.428 | 1.262 | | | 26.194 | 21.208 | 4.986 | | |
| 26.393 | 18.319 | 8.074 | 6.812 | 0 | 27.94 | 19.724 | 8.216 | 3.23 | 0 |
| 22.152 | 19.258 | 2.894 | | | 28.298 | 22.061 | 6.237 | | |
| 27.772 | 19.414 | 8.358 | 5.464 | 0 | 29.836 | 20.977 | 8.859 | 2.622 | 0 |

FIG. 4C (Cont. 3)

|  | BNC1 | | | | | RARB | | | | |
| --- | --- | --- | --- | --- | --- | --- | --- | --- | --- | --- |
|  | Ctm | Ctu | dCt | ddCt | % | Ctm | Ctu | dCt | ddCt | % |
| 301N | 26.199 | 25.478 | 0.721 |  |  | 24.749 | 22.199 | 2.55 |  |  |
| 301T | 26.048 | 25.46 | 0.588 | -0.133 | 0.665 | 21.82 | 21.812 | 0.008 | -2.542 | 12.71 |
| 302N | 32.347 | 29.154 | 3.193 |  |  | 21.981 | 21.836 | 0.145 |  |  |
| 302T | 30.849 | 27 | 3.849 | 0.656 | 0 | 23.534 | 21.642 | 1.892 | 1.747 | 0 |
| 303N | 33.552 | 26.91 | 6.642 |  |  | 28.82 | 22.339 | 6.481 |  |  |
| 303T | 25.49 | 22.256 | 3.234 | -3.408 | 17.04 | 21.736 | 20.974 | 0.762 | -5.719 | 28.595 |
| 304N | 31.227 | 26.888 | 4.339 |  |  | 23.774 | 22.858 | 0.916 |  |  |
| 304T | 28.406 | 26.019 | 2.387 | -1.952 | 9.76 | 20.695 | 21 | -0.305 | -1.221 | 6.105 |
| 305N | 26.674 | 24.487 | 2.187 |  |  | 22.901 | 22.153 | 0.748 |  |  |
| 305T | 21.684 | 23.393 | -1.709 | -3.896 | 19.48 | 17.826 | 19 | -1.174 | -1.922 | 9.61 |
| 306N | 29.226 | 24.851 | 4.375 |  |  | 20.369 | 21.469 | -1.1 |  |  |
| 306T | 22.809 | 21.868 | 0.941 | -3.434 | 17.17 | 18.488 | 20.267 | -1.779 | -0.679 | 3.395 |
| 307N | 28.526 | 26.204 | 2.322 |  |  | 21.859 | 20.872 | 0.987 |  |  |
| 307T | 19.294 | 21.491 | -2.197 | -4.519 | 22.595 | 17.338 | 21.353 | -4.015 | -5.002 | 25.01 |
| 308N | 26.964 | 25.525 | 1.439 |  |  | 15.795 | 18.258 | -2.463 |  |  |
| 308T | 18.652 | 20.238 | -1.586 | -3.025 | 15.125 | 17.055 | 19.523 | -2.468 | -0.005 | 0.025 |
| 309N | 31.764 | 28.168 | 3.596 |  |  | 29.791 | 22 | 7.791 |  |  |
| 309T | 21.872 | 23.12 | -1.248 | -4.844 | 24.22 | 17.216 | 14.949 | 2.267 | -5.524 | 27.62 |
| 310N | 31 | 25.185 | 5.815 |  |  | 22.32 | 20.752 | 1.568 |  |  |
| 310T | 23.231 | 24.022 | -0.791 | -6.606 | 33.03 | 16.217 | 15.037 | 1.18 | -0.388 | 1.94 |
| 311N | 25.073 | 21.678 | 3.395 |  |  | 20 | 20.009 | -0.009 |  |  |
| 311T | 23.83 | 22.283 | 1.547 | -1.848 | 9.24 | 16.115 | 15.18 | 0.935 | 0.944 | 0 |
| 312N | 30.958 | 27.478 | 3.48 |  |  | 18.976 | 20.85 | -1.874 |  |  |
| 312T | 24.211 | 24.533 | -0.322 | -3.802 | 19.01 | 18.033 | 14.97 | 3.063 | 4.937 | 0 |

FIG. 4C (Cont. 4)

|  | BNC1 | | | | | RARB | | | | |
|---|---|---|---|---|---|---|---|---|---|---|
|  | Ctm | Ctu | dCt | ddCt | % | Ctm | Ctu | dCt | ddCt | % |
| 313N | 33.385 | 32.12 | 1.265 | | | 20.707 | 18.414 | 2.293 | | |
| 313T | 31.937 | 31.34 | 0.597 | -0.668 | 3.34 | 18.034 | 16.838 | 1.196 | -1.097 | 5.485 |
| 314N | 34.074 | 31.609 | 2.465 | | | 21.326 | 19.249 | 2.077 | | |
| 314T | 23.914 | 25.809 | -1.895 | -4.36 | 21.8 | 16.549 | 17.146 | -0.597 | -2.674 | 13.37 |
| 315N | 33.095 | 31.629 | 1.466 | | | 16.918 | 18.443 | -1.525 | | |
| 315T | 31.882 | 30.171 | 1.711 | 0.245 | 0 | 19.514 | 19.149 | 0.365 | 1.89 | 0 |
| 316N | 33.725 | 31.394 | 2.331 | | | 18.716 | 19 | -0.284 | | |
| 316T | 27.464 | 26.199 | 1.265 | -1.066 | 5.33 | 18.124 | 19.002 | -0.878 | -0.594 | 2.97 |
| 317N | 33.379 | 31.251 | 2.128 | | | 18.216 | 17.985 | 0.231 | | |
| 317T | 32.606 | 30.306 | 2.3 | 0.172 | 0 | 21.743 | 15.905 | 5.838 | 5.607 | 0 |
| 318N | 34.025 | 30.446 | 3.579 | | | 18.279 | 17.736 | 0.543 | | |
| 318T | 25.318 | 23.988 | 1.33 | -2.249 | 11.245 | 14.654 | 15.467 | -0.813 | -1.356 | 6.78 |
| 319N | 34.716 | 31.707 | 3.009 | | | 21.767 | 18.581 | 3.186 | | |
| 319T | 25.987 | 23.325 | 2.662 | -0.347 | 1.735 | 21.077 | 13.379 | 7.698 | 4.512 | 0 |
| 320N | 28.147 | 25.748 | 2.399 | | | 19 | 17.015 | 1.985 | | |
| 320T | 23.463 | 24.031 | -0.568 | -2.967 | 14.835 | 19.352 | 16.985 | 2.367 | 0.382 | 0 |
| 321N | 26.622 | 24.947 | 1.675 | | | 17.294 | 18.647 | -1.353 | | |
| 321T | 22.314 | 21.713 | 0.601 | -1.074 | 5.37 | 16.611 | 16.38 | 0.231 | 1.584 | 0 |
| 322N | 34.122 | 31.217 | 2.905 | | | 32.494 | 28.894 | 3.6 | | |
| 322T | 20.461 | 19.265 | 1.196 | -1.709 | 8.545 | 15.365 | 16.189 | -0.824 | -4.424 | 22.12 |
| 323N | 33.811 | 31.518 | 2.293 | | | 22.43 | 18.763 | 3.667 | | |
| 323T | 22.039 | 21.056 | 0.983 | -1.31 | 6.55 | 15.071 | 15.696 | -0.625 | -4.292 | 21.46 |
| 324N | 32.758 | 29.752 | 3.006 | | | 17.627 | 17.276 | 0.351 | | |
| 324T | 21.715 | 19.187 | 2.528 | -0.478 | 2.39 | 14.197 | 11.465 | 2.732 | 2.381 | 0 |

FIG. 4C (Cont. 5)

|      | H19 | | | | | ZFAS1 | | | | |
|------|-------|--------|--------|--------|------|--------|--------|-------|--------|------|
|      | Ct | Ctcon | dCt | ddCt | Fold | Ct | Ctcon | dCt | ddCt | Fold |
| 301N | 40.2 | 33.232 | 6.968 | | | 33.929 | 33.232 | 0.697 | | |
| 301T | 35.868 | 31.35 | 4.518 | -2.45 | 5.46 | 31.813 | 31.35 | 0.463 | -0.234 | 1.2 |
| 302N | 33.339 | 32.788 | 0.551 | | | 34.53 | 32.788 | 1.742 | | |
| 302T | 32.024 | 35.092 | -3.068 | -3.619 | 12.3 | 34.294 | 35.092 | -0.798 | -2.54 | 5.8 |
| 303N | 34.073 | 36.511 | -2.438 | | | 40 | 36.511 | 3.489 | | |
| 303T | 31.244 | 32.62 | -1.376 | 1.062 | 0.48 | 33.207 | 32.62 | 0.587 | -2.902 | 7.5 |
| 304N | 34.796 | 36.809 | -2.013 | | | 38.667 | 36.809 | 1.858 | | |
| 304T | 27.043 | 36.617 | -9.574 | -7.561 | 189 | 37.706 | 36.617 | 1.089 | -0.769 | 1.7 |
| 305N | 30.901 | 31.68 | -0.779 | | | 32.848 | 31.68 | 1.168 | | |
| 305T | 26.393 | 31.327 | -4.934 | -4.155 | 17.8 | 30.254 | 31.327 | -1.073 | -2.241 | 4.7 |
| 306N | 30.308 | 32.225 | -1.917 | | | 33.567 | 32.225 | 1.342 | | |
| 306T | 25.459 | 29.486 | -4.027 | -2.11 | 4.32 | 30.894 | 29.486 | 1.408 | 0.066 | 1 |
| 307N | 32.931 | 30.37 | 2.561 | | | 31.887 | 30.37 | 1.517 | | |
| 307T | 33.694 | 28.853 | 4.841 | 2.28 | 0.21 | 28.301 | 28.853 | -0.552 | -2.069 | 4.2 |
| 308N | 29.479 | 29.453 | 0.026 | | | 31.835 | 29.453 | 2.382 | | |
| 308T | 21.926 | 27.044 | -5.118 | -5.144 | 35.4 | 27.187 | 27.044 | 0.143 | -2.239 | 4.7 |
| 309N | 29.151 | 31.725 | -2.574 | | | 33.516 | 31.725 | 1.791 | | |
| 309T | 32.637 | 28.077 | 4.56 | 7.134 | 0.01 | 29.96 | 28.077 | 1.883 | 0.092 | 0.9 |
| 310N | 36.514 | 30.911 | 5.603 | | | 34.033 | 30.911 | 3.122 | | |
| 310T | 36.673 | 28.379 | 8.294 | 2.691 | 0.15 | 28.925 | 28.379 | 0.546 | -2.576 | 6 |

FIG. 4D

|      | H19 | | | | | ZFAS1 | | | | |
|------|------|------|------|------|------|------|------|------|------|------|
|      | Ct | Ctcon | dCt | ddCt | Fold | Ct | Ctcon | dCt | ddCt | Fold |
| 311N | 40.01 | 28.6 | 11.41 | | | 31.406 | 28.6 | 2.806 | | |
| 311T | 30.854 | 28.108 | 2.746 | -8.664 | 406 | 29.622 | 28.108 | 1.514 | -1.292 | 2.4 |
| 312N | 31.827 | 30.437 | 1.39 | | | 32.474 | 30.437 | 2.037 | | |
| 312T | 27.541 | 29.897 | -2.356 | -3.746 | 13.4 | 31.445 | 29.897 | 1.548 | -0.489 | 1.4 |
| 313N | 36.964 | 32.282 | 4.682 | | | 35.322 | 32.282 | 3.04 | | |
| 313T | 37.234 | 28.253 | 8.981 | 4.299 | 0.05 | 31.534 | 28.253 | 3.281 | 0.241 | 0.8 |
| 314N | 30.966 | 28.869 | 2.097 | | | 33.176 | 28.869 | 4.307 | | |
| 314T | 27.141 | 28.32 | -1.179 | -3.276 | 9.69 | 30.643 | 28.32 | 2.323 | -1.984 | 4 |
| 315N | 35.893 | 30.03 | 5.863 | | | 31.775 | 30.03 | 1.745 | | |
| 315T | 28.551 | 28.786 | -0.235 | -6.098 | 68.5 | 29.038 | 28.786 | 0.252 | -1.493 | 2.8 |
| 316N | 33.699 | 29.944 | 3.755 | | | 32.614 | 29.944 | 2.67 | | |
| 316T | 27.876 | 28.455 | -0.579 | -4.334 | 20.2 | 31.155 | 28.455 | 2.7 | 0.03 | 1 |
| 317N | 32.372 | 30.043 | 2.329 | | | 31.851 | 30.043 | 1.808 | | |
| 317T | 24.705 | 27.325 | -2.62 | -4.949 | 30.9 | 28.459 | 27.325 | 1.134 | -0.674 | 1.6 |
| 318N | 28.549 | 27.432 | 1.117 | | | 31.437 | 27.432 | 4.005 | | |
| 318T | 23.47 | 25.215 | -1.745 | -2.862 | 7.27 | 27.477 | 25.215 | 2.262 | -1.743 | 3.3 |
| 319N | 31.798 | 29.509 | 2.289 | | | 31.185 | 29.509 | 1.676 | | |
| 319T | 33.103 | 28.342 | 4.761 | 2.472 | 0.18 | 29.499 | 28.342 | 1.157 | -0.519 | 1.4 |
| 320N | 30.778 | 30.124 | 0.654 | | | 30.769 | 30.124 | 0.645 | | |
| 320T | 22.168 | 27.221 | -5.053 | -5.707 | 52.2 | 27.302 | 27.221 | 0.081 | -0.564 | 1.5 |
| 321N | 29.007 | 28.083 | 0.924 | | | 31.144 | 28.083 | 3.061 | | |
| 321T | 24.608 | 25.595 | -0.987 | -1.911 | 3.76 | 28.001 | 25.595 | 2.406 | -0.655 | 1.6 |
| 322N | 30.046 | 29.463 | 0.583 | | | 31.174 | 29.463 | 1.711 | | |
| 322T | 21.557 | 25.315 | -3.758 | -4.341 | 20.3 | 25.366 | 25.315 | 0.051 | -1.66 | 3.2 |
| 323N | 27.991 | 30.616 | -2.625 | | | 31.64 | 30.616 | 1.024 | | |
| 323T | 26.448 | 27.344 | -0.896 | 1.729 | 0.3 | 29.095 | 27.344 | 1.751 | 0.727 | 0.6 |
| 324N | 31.892 | 31.661 | 0.231 | | | 32.024 | 31.661 | 0.363 | | |
| 324T | 26.645 | 28.72 | -2.075 | -2.306 | 4.95 | 29.137 | 28.72 | 0.417 | 0.054 | 1 |

FIG. 4D (Cont.)

|     | SOX4 | | | | | AMACR | | | | | MET | | | | |
| --- | --- | --- | --- | --- | --- | --- | --- | --- | --- | --- | --- | --- | --- | --- | --- |
|     | Ct | Ctc | dCt | ddCt | F | Ct | Ctc | dCt | ddCt | F | Ct | Ctc | dCt | ddCt | F |
| 1N | 36.254 | 33.196 | 3.058 | | | 31.228 | 33.196 | -1.968 | | | 34.717 | 33.196 | 1.521 | | |
| 1T | 36.706 | 33.473 | 3.233 | 0.175 | 0.89 | 30.929 | 33.473 | -2.544 | -0.576 | 1.5 | 34.631 | 33.473 | 1.158 | -0.363 | 1.29 |
| 2N | 34.027 | 35.443 | -1.416 | | | 34.64 | 35.443 | -0.803 | | | 36.056 | 35.443 | 0.613 | | |
| 2T | 36.308 | 37.852 | -1.544 | -0.128 | 1.09 | 35.713 | 37.852 | -2.139 | -1.336 | 2.5 | 45 | 37.852 | 7.148 | 6.535 | 0.01 |
| 3N | 34.306 | 33.086 | 1.22 | | | 32.065 | 33.086 | -1.021 | | | 34.626 | 33.086 | 1.54 | | |
| 3T | 38.41 | 37.014 | 1.396 | 0.176 | 0.89 | 35.596 | 37.014 | -1.418 | -0.397 | 1.3 | 45 | 37.014 | 7.986 | 6.446 | 0.01 |
| 4N | 34.176 | 32.644 | 1.532 | | | 33.231 | 32.644 | 0.587 | | | 34.168 | 32.644 | 1.524 | | |
| 4T | 33.816 | 36.5 | -2.684 | -4.216 | 18.6 | 34.183 | 36.5 | -2.317 | -2.904 | 7.5 | 37.447 | 36.5 | 0.947 | -0.577 | 1.49 |
| 5N | 37.047 | 33.013 | 4.034 | | | 31.024 | 33.013 | -1.989 | | | 35.045 | 33.013 | 2.032 | | |
| 5T | 34.649 | 35.043 | -0.394 | -4.428 | 21.5 | 33.449 | 35.043 | -1.594 | 0.395 | 0.8 | 34.611 | 35.043 | -0.432 | -2.464 | 5.52 |
| 6N | 33.657 | 36.435 | -2.778 | | | 34.74 | 36.435 | -1.695 | | | 39.196 | 36.435 | 2.761 | | |
| 6T | 34.107 | 36.165 | -2.058 | 0.72 | 0.61 | 32.746 | 36.165 | -3.419 | -1.724 | 3.3 | 36.625 | 36.165 | 0.46 | -2.301 | 4.93 |
| 7N | 34.583 | 31.6 | 2.983 | | | 31.616 | 31.6 | 0.016 | | | 33.455 | 31.6 | 1.855 | | |
| 7T | 32.149 | 31.511 | 0.638 | -2.345 | 5.08 | 33.093 | 31.511 | 1.582 | 1.566 | 0.3 | 34.333 | 31.511 | 2.822 | 0.967 | 0.51 |
| 8N | 36.009 | 33.212 | 2.797 | | | 31.124 | 33.212 | -2.088 | | | 35 | 33.212 | 1.788 | | |
| 8T | 32.595 | 32.703 | -0.108 | -2.905 | 7.49 | 31.696 | 32.703 | -1.007 | 1.081 | 0.5 | 34.171 | 32.703 | 1.468 | -0.32 | 1.25 |
| 9N | 36.21 | 30.98 | 5.23 | | | 32.755 | 30.98 | 1.775 | | | 34.496 | 30.98 | 3.516 | | |
| 9T | 45 | 40 | 5 | -0.23 | 1.17 | 37.131 | 40 | -2.869 | -4.644 | 25 | 40 | 40 | 0 | -3.516 | 11.4 |

FIG. 5A

| | | | | | | | | | | | | | | |
|---|---|---|---|---|---|---|---|---|---|---|---|---|---|---|
| 10N | 35.164 | 32.708 | 2.456 | | | 33.416 | 32.708 | 0.708 | | | 35.99 | 32.708 | 3.282 | | |
| 10T | 31.81 | 33.074 | -1.264 | -3.72 | 13.2 | 36.905 | 33.074 | 3.831 | 3.123 | 0.1 | 34.849 | 33.074 | 1.775 | -1.507 | 2.84 |
| 11N | 32.745 | 29.627 | 3.118 | | | 31.118 | 29.627 | 1.491 | | | 32.891 | 29.627 | 3.264 | | |
| 11T | 30.187 | 30.892 | -0.705 | 3.823 | 14.2 | 33.761 | 30.892 | 2.869 | 1.378 | 0.4 | 31.873 | 30.892 | 0.981 | -2.283 | 4.87 |
| 12N | 33.837 | 30.971 | 2.866 | | | 29.976 | 30.971 | -0.995 | | | 32.651 | 30.971 | 1.68 | | |
| 12T | 33.752 | 31.419 | 2.333 | 0.533 | 1.45 | 29.142 | 31.419 | -2.277 | -1.282 | 2.4 | 31.104 | 31.419 | -0.315 | -1.995 | 3.99 |
| 13N | 33.881 | 30.843 | 3.038 | | | 31.735 | 30.843 | 0.892 | | | 34.019 | 30.843 | 3.176 | | |
| 13T | 33.623 | 32.585 | 1.038 | -2 | 4 | 32.512 | 32.585 | -0.073 | -0.965 | 2 | 35.795 | 32.585 | 3.21 | 0.034 | 0.98 |
| 14N | 42 | 36.555 | 5.445 | | | 38.545 | 36.555 | 1.99 | | | 39.214 | 36.555 | 2.659 | | |
| 14T | 33.856 | 30.725 | 3.131 | 2.314 | 4.97 | 30.151 | 30.725 | -0.574 | -2.564 | 5.9 | 30.827 | 30.725 | 0.102 | -2.557 | 5.88 |
| 15N | 38.819 | 35.859 | 2.96 | | | 35.843 | 35.859 | -0.016 | | | 36.946 | 35.859 | 1.087 | | |
| 15T | 37.078 | 37.415 | -0.337 | 3.297 | 9.83 | 35.6 | 37.415 | -1.815 | -1.799 | 3.5 | 38.593 | 37.415 | 1.178 | 0.091 | 0.94 |
| 16N | 34.613 | 29.756 | 4.857 | | | 30.371 | 29.756 | 0.615 | | | 32.283 | 29.756 | 2.527 | | |
| 16T | 33.974 | 30.187 | 3.787 | -1.07 | 2.1 | 30.458 | 30.187 | 0.271 | -0.344 | 1.3 | 30.954 | 30.187 | 0.767 | -1.76 | 3.39 |
| 17N | 40 | 36.045 | 3.955 | | | 36.329 | 36.045 | 0.284 | | | 37.148 | 36.045 | 1.103 | | |
| 17T | 30.766 | 31.115 | -0.349 | 4.304 | 19.8 | 31.955 | 31.115 | 0.84 | 0.556 | 0.7 | 33.433 | 31.115 | 2.318 | 1.215 | 0.43 |

FIG. 5A (Cont. 1)

|  | MMP 2 | | | | | EGFR | | | | |
|---|---|---|---|---|---|---|---|---|---|---|
|  | Ct | Ctc | dCt | ddCt | F | Ct | Ctc | dCt | ddCt | F |
| 1N | 34.84 | 33.19 | 1.649 | | | 33.6 | 33.19 | 0.40 | | |
| 1T | 36.26 | 33.47 | 2.794 | 1.15 | 0.4521 | 34.54 | 33.47 | 1.07 | 0.672 | 0.62763 |
| 2N | 33.80 | 35.44 | -1.635 | | | 36.07 | 35.44 | 0.63 | | |
| 2T | 33.43 | 37.85 | -4.42 | -2.8 | 6.892 | 37.86 | 37.85 | 0.01 | -0.62 | 1.54007 |
| 3N | 34.02 | 33.08 | 0.934 | | | 34.39 | 33.08 | 1.31 | | |
| 3T | 37.78 | 37.01 | 0.771 | -0.2 | 1.119 | 38.64 | 37.01 | 1.63 | 0.322 | 0.79996 |
| 4N | 32.8 | 32.64 | 0.164 | | | 34.80 | 32.64 | 2.15 | | |
| 4T | 33.48 | 36.5 | -3.012 | -3.2 | 9.037 | 41 | 36.5 | 4.5 | 2.342 | 0.19723 |
| 5N | 34.82 | 33.01 | 1.812 | | | 34.03 | 33.01 | 1.01 | | |
| 5T | 33.61 | 35.04 | -1.433 | -3.2 | 9.480 | 34.69 | 35.04 | -0.34 | -1.36 | 2.5721 |
| 6N | 34.97 | 36.43 | -1.465 | | | 38.52 | 36.43 | 2.08 | | |
| 6T | 42 | 36.16 | 5.835 | 7.3 | 0.0063 | 42 | 36.16 | 5.83 | 3.748 | 0.0744 |
| 7N | 31.90 | 31.6 | 0.301 | | | 31.61 | 31.6 | 0.01 | | |
| 7T | 31.98 | 31.51 | 0.475 | 0.17 | 0.8863 | 32.79 | 31.51 | 1.28 | 1.272 | 0.4140 |
| 8N | 34.05 | 33.21 | 0.838 | | | 33.57 | 33.21 | 0.35 | | |
| 8T | 34.46 | 32.70 | 1.762 | 0.92 | 0.5270 | 32.94 | 32.70 | 0.24 | -0.12 | 1.0844 |
| 9N | 32.72 | 30.98 | 1.746 | | | 32.08 | 30.98 | 1.10 | | |
| 9T | 38.88 | 40 | -1.113 | -2.9 | 7.255 | 39.17 | 40 | -0.82 | -1.92 | 3.794 |
| 10N | 32.07 | 32.70 | -0.629 | | | 33.50 | 32.70 | 0.8 | | |
| 10T | 33.96 | 33.07 | 0.893 | 1.52 | 0.3482 | 33.95 | 33.07 | 0.87 | 0.076 | 0.9486 |
| 11N | 31.61 | 29.62 | 1.99 | | | 31.27 | 29.62 | 1.64 | | |
| 11T | 33.20 | 30.89 | 2.309 | 0.32 | 0.8016 | 33.33 | 30.89 | 2.44 | 0.799 | 0.57474 |
| 12N | 31.48 | 30.97 | 0.514 | | | 30.67 | 30.97 | -0.29 | | |
| 12T | 34.30 | 31.41 | 2.882 | 2.37 | 0.1937 | 31.25 | 31.41 | -0.16 | 0.128 | 0.91509 |
| 13N | 31.865 | 30.843 | 1.022 | | | 32.617 | 30.843 | 1.774 | | |
| 13T | 31.387 | 32.585 | -1.198 | -2.2 | 4.6589 | 33.479 | 32.585 | 0.89 | -0.88 | 1.84037 |
| 14N | 35.41 | 36.55 | -1.143 | | | 37.29 | 36.55 | 0.73 | | |
| 14T | 30.70 | 30.72 | -0.02 | 1.12 | 0.4591 | 30.23 | 30.72 | -0.489 | -1.23 | 2.3391 |
| 15N | 36.264 | 35.859 | 0.405 | | | 36.621 | 35.859 | 0.762 | | |
| 15T | 34.249 | 37.415 | -3.166 | -3.6 | 11.8844 | 36.905 | 37.415 | -0.51 | -1.27 | 2.414961 |
| 16N | 32.016 | 29.756 | 2.26 | | | 30.398 | 29.756 | 0.642 | | |
| 16T | 31.314 | 30.187 | 1.127 | -1.1 | 2.19314 | 30.017 | 30.187 | -0.17 | -0.81 | 1.755644 |

FIG. 5A (Cont. 2)

| | | 36.04 | | | | | 36.04 | | | |
|---|---|---|---|---|---|---|---|---|---|---|
| 17N | 35.48 | 5 | -0.565 | | | 34.91 | 5 | -1.135 | | |
| 17T | 34.26 | 31.11 5 | 3.145 | 3.71 | 0.0764 2 | 34.78 | 31.11 5 | 3.665 | 4.8 | 0.03589 7 |

FIG. 5A (Cont. 3)

|  | miR-182 | | | | | miR-183 | | | | | miR-222 | | | | | miR-21 | | | | |
|---|---|---|---|---|---|---|---|---|---|---|---|---|---|---|---|---|---|---|---|---|
|  | Ct | Ctc | dCt | ddCt | F | Ct | Ctc | dCt | ddCt | F | Ct | Ctc | dCt | ddCt | F | Ct | Ctc | dCt | ddCt | F |
| 1N | 32.6 | 25.4 | 7.189 | | | 38.16 | 25.37 | 12.79 | | | 26.4 | 25.37 | 1.006 | | | 22.4 | 25.37 | -2.956 | | |
| 1T | 35 | 25.7 | 9.3 | 2.111 | 0.2 | 38.23 | 25.74 | 12.49 | -0.3 | 1.23 | 28.4 | 25.74 | 2.683 | 1.68 | 0.31 | 25.8 | 25.74 | 0.051 | 3.007 | 0.124 |
| 2N | 30.1 | 26.7 | 3.417 | | | 33.35 | 26.73 | 6.622 | | | 27.1 | 26.73 | 0.356 | | | 23 | 26.73 | -3.729 | | |
| 2T | 33.9 | 27.6 | 6.311 | 2.894 | 0.1 | 40 | 27.62 | 12.38 | 5.76 | 0.02 | 27.6 | 27.62 | -0.03 | -0.39 | 1.31 | 22.9 | 27.62 | -4.758 | -1.029 | 2.041 |
| 3N | 32.4 | 23.7 | 8.746 | | | 36.66 | 23.65 | 13 | | | 27.9 | 23.65 | 4.272 | | | 22.7 | 23.65 | -0.958 | | |
| 3T | 31 | 26.1 | 4.949 | -3.797 | 14 | 34.28 | 26.09 | 8.188 | -4.81 | 28.1 | 26.9 | 26.09 | 0.838 | -3.43 | 10.8 | 22.8 | 26.09 | -3.305 | -2.347 | 5.088 |
| 4N | 30 | 27.2 | 2.825 | | | 34.47 | 27.21 | 7.264 | | | 27.4 | 27.21 | 0.162 | | | 20.9 | 27.21 | -6.336 | | |
| 4T | 27.1 | 26.9 | 0.148 | -2.677 | 6.4 | 28.84 | 26.95 | 1.897 | -5.37 | 41.3 | 23.1 | 26.95 | -3.86 | -4.03 | 16.3 | 21.4 | 26.95 | -5.517 | 0.819 | 0.567 |
| 5N | 33.1 | 23.8 | 9.39 | | | 35.79 | 23.76 | 12.03 | | | 27.7 | 23.76 | 3.927 | | | 23 | 23.76 | -0.753 | | |
| 5T | 26.9 | 25.7 | 1.14 | -8.25 | 304 | 30.49 | 25.73 | 4.76 | -7.27 | 155 | 27.1 | 25.73 | 1.355 | -2.57 | 5.95 | 23.7 | 25.73 | -2.02 | -1.267 | 2.407 |
| 6N | 30 | 28.3 | 1.81 | | | 33.6 | 28.33 | 5.28 | | | 27 | 28.33 | -1.22 | | | 23 | 28.3 | - | | |

FIG. 5B

|   | 1 | 3 | 9 |   |   | 1 | 3 | 4 |   |   | 1 |   |   |   |   | 5 | 3 | 4.816 |   |   |
|---|---|---|---|---|---|---|---|---|---|---|---|---|---|---|---|---|---|---|---|---|
| 6T | 31.3 | 24.3 | 6.974 | 5.155 | 0 | 34.37 | 24.29 | 10.09 | 4.8 | 0.04 | 28.1 | 24.29 | 3.777 | 4.99 | 0.03 | 22.9 | 24.29 | -1.346 | 3.47 | 0.09 |
| 7N | 29.8 | 19.8 | 10.04 |   |   | 35.87 | 19.76 | 16.11 |   |   | 26.7 | 19.76 | 6.917 |   |   | 22.2 | 19.76 | 2.418 |   |   |
| 7T | 27.3 | 20.4 | 6.853 | 3.191 | 9.1 | 31.27 | 20.44 | 10.83 | -5.28 | 38.7 | 24 | 20.44 | 3.547 | -3.37 | 10.3 | 20.9 | 20.44 | 0.508 | -1.91 | 3.758 |
| 8N | 31.1 | 23.3 | 7.864 |   |   | 37.31 | 23.26 | 14.06 |   |   | 27.2 | 23.26 | 3.938 |   |   | 22.6 | 23.26 | -0.7 |   |   |
| 8T | 27.3 | 22 | 5.316 | -2.548 | 5.8 | 31.28 | 22.02 | 9.261 | -4.79 | 27.7 | 27.1 | 22.02 | 5.042 | 1.1 | 0.47 | 21.3 | 22.02 | -0.688 | 0.012 | 0.992 |
| 9N | 31.1 | 21.5 | 9.617 |   |   | 35.08 | 21.45 | 13.63 |   |   | 25.8 | 21.45 | 4.32 |   |   | 22.1 | 21.45 | 0.696 |   |   |
| 9T | 35.9 | 28.1 | 7.747 | -1.87 | 3.7 | 45 | 28.12 | 16.89 | 3.26 | 0.1 | 33.3 | 28.12 | 5.208 | 0.89 | 0.54 | 29.2 | 28.12 | 1.115 | 0.419 | 0.748 |
| 10N | 29.9 | 21.6 | 8.33 |   |   | 35.13 | 21.6 | 13.53 |   |   | 25.6 | 21.6 | 3.951 |   |   | 22.2 | 21.6 | 0.565 |   |   |
| 10T | 27.6 | 22.4 | 5.247 | -3.083 | 8.5 | 31.54 | 22.39 | 9.156 | -4.38 | 20.8 | 22.8 | 22.39 | 0.417 | -3.53 | 11.6 | 19.1 | 22.39 | -3.304 | -3.869 | 14.61 |
| 11N | 28.2 | 19.3 | 8.883 |   |   | 33.05 | 19.33 | 13.72 |   |   | 24.1 | 19.33 | 4.738 |   |   | 20.3 | 19.33 | 0.95 |   |   |
| 11T | 25.2 | 20 | 5.22 | -3.663 | 13 | 29.27 | 20.01 | 9.26 | -4.46 | 22.1 | 25 | 20.01 | 4.966 | 0.23 | 0.85 | 19.4 | 20.01 | -0.608 | -1.558 | 2.944 |
| 12N | 29.5 | 19.9 | 9.627 |   |   | 34.22 | 19.91 | 14.31 |   |   | 25.5 | 19.91 | 5.597 |   |   | 21 | 19.91 | 1.103 |   |   |
| 12T | 28.4 | 19.2 | 9.199 | -0.428 | 1.3 | 33.04 | 19.2 | 13.84 | -0.47 | 1.39 | 24.4 | 19.2 | 5.187 | -0.41 | 1.33 | 20.3 | 19.2 | -1.056 | -0.047 | 1.033 |

FIG. 5B (Cont. 1)

| 13N | 28.4 | 20.8 | 7.52 | | | 34.32 | 20.83 | 13.49 | | | 24.1 | 20.83 | 3.30 | | | | 22 | 20.83 | 1.173 | | |
|---|---|---|---|---|---|---|---|---|---|---|---|---|---|---|---|---|---|---|---|---|---|
| 13T | 26.8 | 20.7 | 6.107 | -1.417 | 2.7 | 31.63 | 20.67 | 10.97 | -2.53 | 5.76 | 24 | 20.67 | 3.315 | 0.01 | 0.99 | 20.9 | 20.67 | 0.245 | -0.928 | 1.903 |
| 14N | 32.4 | 25.9 | 6.494 | | | 36.88 | 25.9 | 10.98 | | | 28.8 | 25.9 | 2.95 | | | | 27.1 | 25.9 | 1.153 | | |
| 14T | 30.3 | 18.5 | 11.86 | 5.368 | 0 | 35.07 | 18.47 | 16.6 | 5.62 | 0.02 | 24.1 | 18.47 | 5.576 | 2.63 | 0.16 | 20.8 | 18.47 | 2.294 | 1.141 | 0.453 |
| 15N | 32.5 | 24.2 | 8.33 | | | 38.75 | 24.21 | 14.54 | | | 26.2 | 24.21 | 1.99 | | | | 24.1 | 24.21 | -0.096 | | |
| 15T | 32.6 | 26.1 | 6.502 | -1.831 | 3.6 | 35.12 | 26.14 | 8.986 | -5.56 | 47.1 | 26.1 | 26.14 | 0.004 | -1.99 | 3.96 | 22.4 | 26.14 | -3.691 | 3.595 | 12.08 |
| 16N | 30.2 | 19.5 | 10.73 | | | 35.54 | 19.47 | 16.07 | | | 25.4 | 19.47 | 5.925 | | | | 21.4 | 19.47 | 1.969 | | |
| 16T | 25.9 | 19.8 | 6.177 | 4.551 | .23 | 31.18 | 19.77 | 11.41 | -4.66 | 25.3 | 25.3 | 19.77 | 5.486 | -0.44 | 1.36 | 21.1 | 19.77 | 1.295 | 0.674 | 1.595 |
| 17N | 31.7 | 24.3 | 7.383 | | | 37.04 | 24.28 | 12.76 | | | 28.8 | 24.28 | 4.501 | | | | 24.3 | 24.28 | 0.068 | | |
| 17T | 25.8 | 19.5 | 6.28 | 1.103 | 2.1 | 30.94 | 19.54 | 11.4 | -1.36 | 2.57 | 23.2 | 19.54 | 3.708 | -0.79 | 1.73 | 20.2 | 19.54 | 0.654 | 0.586 | 0.666 |

FIG. 5B (Cont. 2)

|  | BNC1m | | | | | MGMTm | | | | |
| --- | --- | --- | --- | --- | --- | --- | --- | --- | --- | --- |
|  | Ctm | Ctu | dCt | ddCt | % | Ctm | Ctu | dCt | ddCt | % |
| 1N | 25.047 | 15.921 | 9.126 |  |  | 30.159 | 25.131 | 5.028 |  |  |
| 1T | 22.688 | 14.635 | 8.053 | -1.07 | 5.37 | 29.191 | 21.02 | 8.171 | 3.143 | 0 |
| 3N | 24.631 | 14.556 | 10.08 |  |  | 29.308 | 21.387 | 7.921 |  |  |
| 3T | 23.228 | 14.736 | 8.492 | -1.58 | 7.92 | 29.718 | 21.614 | 8.104 | 0.183 | 0 |
| 4N | 23.327 | 14.613 | 8.714 |  |  | 29.083 | 21.177 | 7.906 |  |  |
| 4T | 21.414 | 14.379 | 7.035 | -1.68 | 8.4 | 28.45 | 20.448 | 8.002 | 0.096 | 0 |
| 5N | 28.216 | 15.993 | 12.22 |  |  | 30.674 | 24.248 | 6.426 |  |  |
| 5T | 20.288 | 14.4 | 5.888 | -6.34 | 31.7 | 22.697 | 20.584 | 2.113 | -4.31 | 21.57 |
| 6N | 24.006 | 14.885 | 9.121 |  |  | 28.684 | 21.745 | 6.939 |  |  |
| 6T | 20.328 | 14.427 | 5.901 | -3.22 | 16.1 | 25.928 | 21.277 | 4.651 | -2.29 | 11.44 |
| 7N | 23.42 | 14.734 | 8.686 |  |  | 27.895 | 21.429 | 6.466 |  |  |
| 7T | 20.854 | 14.313 | 6.541 | -2.15 | 10.7 | 27.125 | 20.185 | 6.94 | 0.474 | 0 |
| 8N | 23.643 | 15.463 | 8.18 |  |  | 29.434 | 21.478 | 7.956 |  |  |
| 8T | 19.651 | 14.409 | 5.242 | -2.94 | 14.7 | 23.306 | 20.86 | 2.446 | -5.51 | 27.55 |
| 9N | 24.211 | 14.926 | 9.285 |  |  | 26.315 | 21.76 | 4.555 |  |  |
| 9T | 22.212 | 14.568 | 7.644 | -1.64 | 8.21 | 28.675 | 21.048 | 7.627 | 3.072 | 0 |
| 10N | 22.652 | 14.588 | 8.064 |  |  | 27.667 | 20.3 | 7.367 |  |  |
| 10T | 18.073 | 14.149 | 3.924 | -4.14 | 20.7 | 20.638 | 18.873 | 1.765 | -5.6 | 28.01 |
| 11N | 22.054 | 14.456 | 7.598 |  |  | 24.817 | 20.143 | 4.674 |  |  |
| 11T | 17.571 | 14.061 | 3.51 | -4.09 | 20.4 | 19.759 | 19.42 | 0.339 | -4.34 | 21.68 |
| 12N | 22.683 | 15.128 | 7.555 |  |  | 26.939 | 22.132 | 4.807 |  |  |
| 12T | 21.092 | 14.457 | 6.635 | -0.92 | 4.6 | 24.229 | 20.252 | 3.977 | -0.83 | 4.15 |
| 13N | 22.899 | 14.665 | 8.234 |  |  | 28.462 | 21.751 | 6.711 |  |  |
| 13T | 20.748 | 14.443 | 6.305 | -1.93 | 9.65 | 23.071 | 21.964 | 1.107 | -5.6 | 28.02 |
| 14N | 24.679 | 15.27 | 9.409 |  |  | 29.549 | 22.385 | 7.164 |  |  |
| 14T | 21.472 | 14.901 | 6.571 | -2.84 | 14.2 | 28.997 | 21.393 | 7.604 | 0.44 | 0 |
| 15N | 24.128 | 15.133 | 8.995 |  |  | 29.248 | 22.464 | 6.784 |  |  |
| 15T | 19.954 | 14.363 | 5.591 | -3.4 | 17 | 28.098 | 20.542 | 7.556 | 0.772 | 0 |

FIG. 5C

| | | | | | | | | | |
|---|---|---|---|---|---|---|---|---|---|
| 16N | 23.414 | 15.157 | 8.257 | | | 24.968 | 22.277 | 2.691 | | |
| 16T | 22.193 | 14.475 | 7.718 | 0.54 | 2.7 | 28.346 | 22.907 | 5.439 | 2.748 | 0 |
| 17N | 23.557 | 15.037 | 8.52 | | | 29.112 | 21.648 | 7.464 | | |
| 17T | 21.874 | 14.756 | 7.118 | -1.4 | 7.01 | 28.775 | 21.476 | 7.299 | -0.16 | 0.83 |
| 18N | 24.181 | 15.381 | 8.8 | | | 29.476 | 22.434 | 7.042 | | |
| 18T | 19.127 | 14.341 | 4.786 | -4.01 | 20.1 | 27.964 | 20.071 | 7.893 | 0.851 | 0 |
| 19N | 23.312 | 15.173 | 8.139 | | | 29.484 | 23.003 | 6.481 | | |
| 19T | 21.473 | 15.14 | 6.333 | 1.81 | 9.03 | 28.511 | 22.338 | 6.173 | -0.31 | 1.54 |
| 20N | 22.865 | 15.145 | 7.72 | | | 29.05 | 22.037 | 7.013 | | |
| 20T | 21.373 | 14.684 | 6.689 | 1.03 | 5.16 | 28.871 | 21.506 | 7.365 | 0.352 | 0 |
| 21N | 22.997 | 15.038 | 7.959 | | | 29.392 | 21.56 | 7.832 | | |
| 21T | 20.226 | 14.588 | 5.638 | -2.32 | 11.6 | 23.348 | 21.946 | 1.402 | -6.43 | 32.15 |
| 22N | 24.115 | 15.522 | 8.593 | | | 29.042 | 23.402 | 5.64 | | |
| 22T | 20.019 | 14.855 | 5.164 | -3.43 | 17.2 | 22.599 | 22.095 | 0.504 | -5.14 | 25.68 |
| 23N | 23.783 | 15.466 | 8.317 | | | 28.71 | 22.731 | 5.979 | | |
| 23T | 21.949 | 14.85 | 7.099 | 1.22 | 6.09 | 28.804 | 21.197 | 7.607 | 1.628 | 0 |
| 24N | 24.621 | 15.575 | 9.046 | | | 29.735 | 22.686 | 7.049 | | |
| 24T | 20.184 | 14.379 | 5.805 | -3.24 | 16.2 | 27.715 | 20.156 | 7.559 | 0.51 | 0 |
| 25N | 23.731 | 15.251 | 8.48 | | | 29.408 | 22.42 | 6.988 | | |
| 25T | 19.525 | 14.706 | 4.819 | -3.66 | 18.3 | 23.292 | 21.29 | 2.002 | -4.99 | 24.93 |

FIG. 5C (Cont. 1)

|  | RASSF1m | | | | | SFRP1m | | | | |
|---|---|---|---|---|---|---|---|---|---|---|
|  | Ctm | Ctu | dCt | ddCt | % | Ctm | Ctu | dCt | ddCt | % |
| 1N | 26.812 | 21.21 | 5.602 |  |  | 25.555 | 21.663 | 3.892 |  |  |
| 1T | 25.762 | 19.478 | 6.284 | 0.682 | 0 | 23.741 | 19.762 | 3.979 | 0.087 | 0 |
| 3N | 27.243 | 21.259 | 5.984 |  |  | 24.895 | 21.122 | 3.773 |  |  |
| 3T | 25.544 | 19.969 | 5.575 | -0.409 | 2.05 | 23.213 | 20.699 | 2.514 | -1.259 | 12.59 |
| 4N | 25.702 | 19.523 | 6.179 |  |  | 23.56 | 19.788 | 3.772 |  |  |
| 4T | 24.48 | 18.073 | 6.407 | 0.228 | 0 | 22.901 | 18.895 | 4.006 | 0.234 | 0 |
| 5N | 29.265 | 24.812 | 4.453 |  |  | 24.997 | 21.927 | 3.07 |  |  |
| 5T | 23.336 | 17.639 | 5.697 | 1.244 | 0 | 22.554 | 18.357 | 4.197 | 1.127 | 0 |
| 6N | 26.009 | 19.66 | 6.349 |  |  | 23.797 | 20.533 | 3.264 |  |  |
| 6T | 20.063 | 18.838 | 1.225 | -5.124 | 25.62 | 22.904 | 21.171 | 1.733 | -1.531 | 15.31 |
| 7N | 24.585 | 19.294 | 5.291 |  |  | 23.726 | 20.141 | 3.585 |  |  |
| 7T | 23.017 | 17.769 | 5.248 | -0.043 | 0.22 | 22.145 | 18.805 | 3.34 | -0.245 | 2.45 |
| 8N | 25.686 | 20.295 | 5.391 |  |  | 24.869 | 21.565 | 3.304 |  |  |
| 8T | 22.074 | 18.761 | 3.313 | -2.078 | 10.39 | 20.312 | 19.307 | 1.005 | -2.299 | 22.99 |
| 9N | 25.607 | 20.439 | 5.168 |  |  | 23.812 | 21.969 | 1.843 |  |  |
| 9T | 22.188 | 18.827 | 3.361 | -1.807 | 9.04 | 23.439 | 19.869 | 3.57 | 1.727 | 0 |
| 10N | 24.009 | 18.5 | 5.509 |  |  | 23.355 | 19.634 | 3.721 |  |  |
| 10T | 17.966 | 17.217 | 0.749 | -4.76 | 23.8 | 18.634 | 17.558 | 1.076 | -2.645 | 26.45 |
| 11N | 21.575 | 18.165 | 3.41 |  |  | 22.438 | 19.319 | 3.119 |  |  |
| 11T | 17.095 | 17.304 | -0.209 | -3.619 | 18.2 | 18.101 | 17.658 | 0.443 | -2.676 | 26.76 |
| 12N | 23.508 | 21.113 | 2.395 |  |  | 21.92 | 20.298 | 1.622 |  |  |
| 12T | 22.975 | 18.198 | 4.777 | 2.382 | 0 | 22.371 | 18.927 | 3.444 | 1.822 | 0 |
| 13N | 24.621 | 19.183 | 5.438 |  |  | 23.314 | 20.206 | 3.108 |  |  |
| 13T | 19.371 | 18.928 | 0.443 | -4.995 | 24.98 | 22.27 | 18.751 | 3.519 | 0.411 | 0 |
| 14N | 26.116 | 20.515 | 5.601 |  |  | 24.426 | 20.553 | 3.873 |  |  |
| 14T | 24.672 | 19.184 | 5.488 | -0.113 | 0.57 | 21.232 | 20.664 | 0.568 | -3.305 | 33.05 |
| 15N | 25.272 | 20.082 | 5.19 |  |  | 23.078 | 20.853 | 2.225 |  |  |
| 15T | 22.953 | 18.154 | 4.799 | -0.391 | 1.96 | 21.668 | 18.587 | 3.081 | 0.856 | 0 |
| 16N | 26.851 | 20.67 | 6.181 |  |  | 23.86 | 21.175 | 2.685 |  |  |
| 16T | 25.485 | 20.597 | 4.888 | -1.293 | 6.47 | 23.343 | 21.003 | 2.34 | -0.345 | 3.45 |
| 17N | 25.383 | 19.777 | 5.606 |  |  | 23.509 | 20.737 | 2.772 |  |  |
| 17T | 24.414 | 19.031 | 5.383 | -0.223 | 1.12 | 22.818 | 20.172 | 2.646 | -0.126 | 1.26 |
| 18N | 26.635 | 20.951 | 5.684 |  |  | 23.655 | 21.394 | 2.261 |  |  |
| 18T | 19.558 | 17.848 | 1.71 | -3.974 | 19.87 | 19.571 | 18.322 | 1.249 | -1.012 | 10.12 |
| 19N | 25 | 19.81 | 5.19 |  |  | 23.229 | 20.478 | 2.751 |  |  |
| 19T | 21.771 | 21.072 | 0.699 | -4.491 | 22.46 | 23.092 | 20.189 | 2.903 | 0.152 | 0 |
| 20N | 25.532 | 20.088 | 5.444 |  |  | 23.994 | 21.083 | 2.911 |  |  |
| 20T | 24.411 | 19.01 | 5.401 | -0.043 | 0.22 | 22.819 | 20.344 | 2.475 | -0.436 | 4.36 |

FIG. 5C (Cont. 2)

| 21N | 23.427 | 19.328 | 4.099 | | | 23.329 | 20.368 | 2.961 | | |
|---|---|---|---|---|---|---|---|---|---|---|
| 21T | 21.53 | 18.514 | 3.016 | -1.083 | 5.42 | 21.096 | 18.988 | 2.108 | -0.853 | 8.53 |
| 22N | 26.066 | 23.455 | 2.611 | | | 22.107 | 20.482 | 1.625 | | |
| 22T | 20.778 | 18.723 | 2.055 | -0.556 | 2.78 | 20.21 | 20.086 | 0.124 | -1.501 | 15.01 |
| 23N | 25.339 | 20.529 | 4.81 | | | 22.867 | 20.978 | 1.889 | | |
| 23T | 22.779 | 18.29 | 4.489 | -0.321 | 1.61 | 22.164 | 19.582 | 2.582 | 0.693 | 0 |
| 24N | 27.838 | 23.006 | 4.832 | | | 23.059 | 21.716 | 1.343 | | |
| 24T | 17.463 | 18.885 | -1.422 | -6.254 | 31.27 | 20.303 | 17.373 | 2.93 | 1.587 | 0 |
| 25N | 23.531 | 20.998 | 2.533 | | | 23.087 | 20.63 | 2.457 | | |
| 25T | 18.964 | 18.596 | 0.368 | -2.165 | 10.83 | 20.422 | 18.926 | 1.496 | -0.961 | 9.61 |

FIG. 5C (Cont. 3)

|  | MALAT1 | | | | |
|---|---|---|---|---|---|
|  | Ct | Ctc | dCt | ddCt | F |
| 1N | 30.738 | 42 | -11.262 | | |
| 1T | 29.444 | 33.024 | -3.58 | 7.682 | 0.00487 |
| 3N | 29.135 | 36.042 | -6.907 | | |
| 3T | 26.332 | 35.784 | -9.452 | -2.545 | 5.836081 |
| 4N | 26.389 | 33.401 | -7.012 | | |
| 4T | 26.432 | 29.387 | -2.955 | 4.057 | 0.060079 |
| 5N | 26.722 | 33.672 | -6.95 | | |
| 5T | 22.313 | 32.457 | -10.144 | -3.194 | 9.151448 |
| 6N | 28.084 | 38.182 | -10.098 | | |
| 6T | 24.165 | 30.314 | -6.149 | 3.949 | 0.064749 |
| 7N | 26.283 | 30.191 | -3.908 | | |
| 7T | 25.65 | 28.149 | -2.499 | 1.409 | 0.376573 |
| 8N | 27.511 | 31.168 | -3.657 | | |
| 8T | 22.38 | 26.854 | -4.474 | -0.817 | 1.761739 |
| 9N | 27.04 | 31.139 | -4.099 | | |
| 9T | 24.414 | 26.642 | -2.228 | 1.871 | 0.273384 |
| 10N | 25.329 | 29.268 | -3.939 | | |
| 10T | 21.795 | 22.66 | -0.865 | 3.074 | 0.11875 |
| 11N | 24.318 | 28.497 | -4.179 | | |
| 11T | 21.568 | 24.178 | -2.61 | 1.569 | 0.337042 |
| 12N | 27.362 | 31.049 | -3.687 | | |
| 12T | 23.485 | 25.339 | -1.854 | 1.833 | 0.28068 |
| 13N | 29.369 | 31.445 | -2.076 | | |
| 13T | 27.225 | 27.723 | -0.498 | 1.578 | 0.334946 |
| 14N | 29.173 | 31.226 | -2.053 | | |
| 14T | 26.019 | 27.901 | -1.882 | 0.171 | 0.888227 |
| 15N | 27.099 | 31.403 | -4.304 | | |
| 15T | 24.125 | 27.063 | -2.938 | 1.366 | 0.387965 |
| 16N | 25.418 | 31.115 | -5.697 | | |
| 16T | 27.341 | 30.375 | -3.034 | 2.663 | 0.157891 |
| 17N | 28.88 | 32.304 | -3.424 | | |
| 17T | 23.799 | 27.82 | -4.021 | -0.597 | 1.512568 |
| 18N | 28.763 | 31.553 | -2.79 | | |
| 18T | 24.08 | 26.082 | -2.002 | 0.788 | 0.579146 |
| 19N | 28.523 | 33.168 | -4.645 | | |
| 19T | 25.619 | 27.809 | -2.19 | 2.455 | 0.182378 |
| 20N | 26.16 | 31.372 | -5.212 | | |
| 20T | 25.374 | 25.597 | -0.223 | 4.989 | 0.031489 |

FIG. 5D

| 21N | 28.033 | 30.504 | -2.471 | | |
|---|---|---|---|---|---|
| 21T | 22.518 | 25.57 | -3.052 | -0.581 | 1.495886 |
| 22N | 28.956 | 32.403 | -3.447 | | |
| 22T | 25.373 | 28.145 | -2.772 | 0.675 | 0.626332 |
| 23N | 27.147 | 32.483 | -5.336 | | |
| 23T | 24.525 | 28.596 | -4.071 | 1.265 | 0.416099 |
| 24N | 29.807 | 34.599 | -4.792 | | |
| 24T | 27.227 | 27.085 | 0.142 | 4.934 | 0.032713 |
| 25N | 30.393 | 40.05 | -9.657 | | |
| 24.081 | 34.088 | -10.007 | -0.35 | 1.274561 | |

FIG. 5D (Cont.)

| | SOX4 | | | | | AMACR | | | | | MET | | | | |
|---|---|---|---|---|---|---|---|---|---|---|---|---|---|---|---|
| | Ct | Ctc | dCt | ddCt | F | Ct | Ctc | dCt | ddCt | F | Ct | Ctc | dCt | ddCt | F |
| 1N | 36.25 | 33.2 | 3.058 | | | 31.23 | 33.2 | -1.968 | | | 34.72 | 33.2 | 1.521 | | |
| 1T | 36.71 | 33.5 | 3.233 | 0.175 | 0.89 | 30.93 | 33.5 | -2.544 | -0.576 | 1.5 | 34.63 | 33.47 | 1.158 | -0.363 | 1.29 |
| 2N | 34.03 | 35.4 | -1.416 | | | 34.64 | 35.4 | -0.803 | | | 36.06 | 35.44 | 0.613 | | |
| 2T | 36.31 | 37.9 | -1.544 | -0.128 | 1.09 | 35.71 | 37.9 | -2.139 | -1.336 | 2.5 | 45 | 37.85 | 7.148 | 6.535 | 0.01 |
| 3N | 34.31 | 33.1 | 1.22 | | | 32.07 | 33.1 | -1.021 | | | 34.63 | 33.09 | 1.54 | | |
| 3T | 38.41 | 37 | 1.396 | 0.176 | 0.89 | 35.6 | 37 | -1.418 | -0.397 | 1.3 | 45 | 37.01 | 7.986 | 6.446 | 0.01 |
| 4N | 34.18 | 32.6 | 1.532 | | | 33.23 | 32.6 | 0.587 | | | 34.17 | 32.64 | 1.524 | | |
| 4T | 33.82 | 36.5 | -2.684 | -4.216 | 18.6 | 34.18 | 36.5 | -2.317 | -2.904 | 7.5 | 37.45 | 36.5 | 0.947 | -0.577 | 1.49 |
| 5N | 37.05 | 33 | 4.034 | | | 31.02 | 33 | -1.989 | | | 35.05 | 33.01 | 2.032 | | |
| 5T | 34.65 | 35 | -0.394 | -4.428 | 21.5 | 33.45 | 35 | -1.594 | 0.395 | 0.8 | 34.61 | 35.04 | -0.432 | -2.464 | 5.52 |
| 6N | 33.66 | 36.4 | -2.778 | | | 34.74 | 36.4 | -1.695 | | | 39.2 | 36.44 | 2.761 | | |
| 6T | 34.11 | 36.2 | -2.058 | 0.72 | 0.61 | 32.75 | 36.2 | -3.419 | -1.724 | 3.3 | 36.63 | 36.17 | 0.46 | -2.301 | 4.93 |
| 7N | 34.58 | 31.6 | 2.983 | | | 31.62 | 31.6 | 0.016 | | | 33.46 | 31.6 | 1.855 | | |
| 7T | 32.15 | 31.5 | 0.638 | -2.345 | 5.08 | 33.09 | 31.5 | 1.582 | 1.566 | 0.3 | 34.33 | 31.51 | 2.822 | 0.967 | 0.51 |
| 8N | 36.01 | 33.2 | 2.797 | | | 31.12 | 33.2 | -2.088 | | | 35 | 33.21 | 1.788 | | |
| 8T | 32.6 | 32.7 | -0.108 | -2.905 | 7.49 | 31.7 | 32.7 | -1.007 | 1.081 | 0.5 | 34.17 | 32.7 | 1.468 | -0.32 | 1.25 |
| 9N | 36.21 | 31 | 5.23 | | | 32.76 | 31 | 1.775 | | | 34.5 | 30.98 | 3.516 | | |

FIG. 6A

| 9T | 45 | 40 | 5 | -0.23 | 1.17 | 37.13 | 40 | -2.869 | 4.644 | -25 | 40 | 40 | 0 | 3.516 | -11.4 |
|---|---|---|---|---|---|---|---|---|---|---|---|---|---|---|---|
| 10N | 35.16 | 32.7 | 2.456 | | | 33.42 | 32.7 | 0.708 | | | 35.99 | 32.71 | 3.282 | | |
| 10T | 31.81 | 33.1 | 1.264 | -3.72 | -13.2 | 36.91 | 33.1 | 3.831 | 3.123 | 0.1 | 34.85 | 33.07 | 1.775 | -1.507 | 2.84 |
| 11N | 32.75 | 29.6 | 3.118 | | | 31.12 | 29.6 | 1.491 | | | 32.89 | 29.63 | 3.264 | | |
| 11T | 30.19 | 30.9 | 0.705 | -3.823 | -14.2 | 33.76 | 30.9 | 2.869 | 1.378 | 0.4 | 31.87 | 30.89 | 0.981 | -2.283 | 4.87 |
| 12N | 33.84 | 31 | 2.866 | | | 29.98 | 31 | -0.995 | | | 32.65 | 30.97 | 1.68 | | |
| 12T | 33.75 | 31.4 | 2.333 | 0.533 | 1.45 | 29.14 | 31.4 | -2.277 | 1.282 | -2.4 | 31.1 | 31.42 | -0.315 | -1.995 | -3.99 |
| 13N | 33.88 | 30.8 | 3.038 | | | 31.74 | 30.8 | 0.892 | | | 34.02 | 30.84 | 3.176 | | |
| 13T | 33.62 | 32.6 | 1.038 | -2 | 4 | 32.51 | 32.6 | -0.073 | 0.965 | 2 | 35.8 | 32.59 | 3.21 | 0.034 | 0.98 |
| 14N | 42 | 36.6 | 5.445 | | | 38.55 | 36.6 | 1.99 | | | 39.21 | 36.56 | 2.659 | | |
| 14T | 33.86 | 30.7 | 3.131 | 2.314 | 4.97 | 30.15 | 30.7 | -0.574 | 2.564 | 5.9 | 30.83 | 30.73 | 0.102 | -2.557 | 5.88 |
| 15N | 38.82 | 35.9 | 2.96 | | | 35.84 | 35.9 | -0.016 | | | 36.95 | 35.86 | 1.087 | | |
| 15T | 37.08 | 37.4 | 0.337 | -3.297 | -9.83 | 35.6 | 37.4 | -1.815 | 1.799 | -3.5 | 38.59 | 37.42 | 1.178 | 0.091 | 0.94 |
| 16N | 34.61 | 29.8 | 4.857 | | | 30.37 | 29.8 | 0.615 | | | 32.28 | 29.76 | 2.527 | | |
| 16T | 33.97 | 30.2 | 3.787 | -1.07 | -2.1 | 30.46 | 30.2 | 0.271 | 0.344 | 1.3 | 30.95 | 30.19 | 0.767 | -1.76 | 3.39 |
| 17N | 40 | 36 | 3.955 | | | 36.33 | 36 | 0.284 | | | 37.15 | 36.05 | 1.103 | | |
| 17T | 30.77 | 31.1 | -0.349 | -4.304 | -19.8 | 31.96 | 31.1 | 0.84 | 0.556 | 0.7 | 33.43 | 31.12 | 2.318 | 1.215 | 0.43 |

FIG. 6A (Cont. 1)

|  | MMP2 | | | | | EGFR | | | | |
| --- | --- | --- | --- | --- | --- | --- | --- | --- | --- | --- |
|  | Ct | Ctc | dCt | ddCt | F | Ct | Ctc | dCt | ddCt | F |
| 1N | 34.85 | 33.2 | 1.649 | | | 33.6 | 33.2 | 0.404 | | |
| 1T | 36.27 | 33.47 | 2.794 | 1.145 | 0.5 | 34.549 | 33.47 | 1.076 | 0.672 | 0.6 |
| 2N | 33.81 | 35.44 | -1.635 | | | 36.078 | 35.44 | 0.635 | | |
| 2T | 33.43 | 37.85 | -4.42 | -2.79 | 6.9 | 37.864 | 37.85 | 0.012 | -0.623 | 1.5 |
| 3N | 34.02 | 33.09 | 0.934 | | | 34.399 | 33.09 | 1.313 | | |
| 3T | 37.79 | 37.01 | 0.771 | -0.16 | 1.1 | 38.649 | 37.01 | 1.635 | 0.322 | 0.8 |
| 4N | 32.81 | 32.64 | 0.164 | | | 34.802 | 32.64 | 2.158 | | |
| 4T | 33.49 | 36.5 | -3.012 | -3.18 | 9 | 41 | 36.5 | 4.5 | 2.342 | 0.2 |
| 5N | 34.83 | 33.01 | 1.812 | | | 34.031 | 33.01 | 1.018 | | |
| 5T | 33.61 | 35.04 | -1.433 | -3.25 | 9.5 | 34.698 | 35.04 | -0.345 | -1.363 | 2.6 |
| 6N | 34.97 | 36.44 | -1.465 | | | 38.522 | 36.44 | 2.087 | | |
| 6T | 42 | 36.17 | 5.835 | 7.3 | 0 | 42 | 36.17 | 5.835 | 3.748 | 0.1 |
| 7N | 31.9 | 31.6 | 0.301 | | | 31.61 | 31.6 | 0.01 | | |
| 7T | 31.99 | 31.51 | 0.475 | 0.174 | 0.9 | 32.793 | 31.51 | 1.282 | 1.272 | 0.4 |
| 8N | 34.05 | 33.21 | 0.838 | | | 33.571 | 33.21 | 0.359 | | |
| 8T | 34.47 | 32.7 | 1.762 | 0.924 | 0.5 | 32.945 | 32.7 | 0.242 | -0.117 | 1.1 |
| 9N | 32.73 | 30.98 | 1.746 | | | 32.083 | 30.98 | 1.103 | | |
| 9T | 38.89 | 40 | -1.113 | -2.86 | 7.3 | 39.179 | 40 | -0.821 | -1.924 | 3.8 |
| 10N | 32.08 | 32.71 | -0.629 | | | 33.508 | 32.71 | 0.8 | | |
| 10T | 33.97 | 33.07 | 0.893 | 1.522 | 0.3 | 33.95 | 33.07 | 0.876 | 0.076 | 0.9 |
| 11N | 31.62 | 29.63 | 1.99 | | | 31.27 | 29.63 | 1.643 | | |

FIG. 6A (Cont. 2)

| 11T | 33.2 | 30.89 | 2.309 | 0.319 | 0.8 | 33.334 | 30.89 | 2.442 | 0.799 | 0.6 |
|---|---|---|---|---|---|---|---|---|---|---|
| 12N | 31.49 | 30.97 | 0.514 | | | 30.675 | 30.97 | -0.296 | | |
| 12T | 34.3 | 31.42 | 2.882 | 2.368 | 0.2 | 31.251 | 31.42 | -0.168 | 0.128 | 0.9 |
| 13N | 31.87 | 30.84 | 1.022 | | | 32.617 | 30.84 | 1.774 | | |
| 13T | 31.39 | 32.59 | -1.198 | -2.22 | 4.7 | 33.479 | 32.59 | 0.894 | -0.88 | 1.8 |
| 14N | 35.41 | 36.56 | -1.143 | | | 37.292 | 36.56 | 0.737 | | |
| 14T | 30.71 | 30.73 | -0.02 | 1.123 | 0.5 | 30.236 | 30.73 | -0.489 | -1.226 | 2.3 |
| 15N | 36.26 | 35.86 | 0.405 | | | 36.621 | 35.86 | 0.762 | | |
| 15T | 34.25 | 37.42 | -3.166 | -3.57 | 12 | 36.905 | 37.42 | -0.51 | 1.272 | 2.4 |
| 16N | 32.02 | 29.76 | 2.26 | | | 30.398 | 29.76 | 0.642 | | |
| 16T | 31.31 | 30.19 | 1.127 | -1.13 | 2.2 | 30.017 | 30.19 | -0.17 | 0.812 | 1.8 |
| 17N | 35.48 | 36.05 | -0.565 | | | 34.91 | 36.05 | -1.135 | | |
| 17T | 34.26 | 31.12 | 3.145 | 3.71 | 0.1 | 34.78 | 31.12 | 3.665 | 4.8 | 0 |

FIG. 6A (Cont. 3)

| | miR-182 | | | | | miR-183 | | | | | miR-222 | | | | | miR-21 | | | | |
|---|---|---|---|---|---|---|---|---|---|---|---|---|---|---|---|---|---|---|---|---|
| | Ct | Ctc | dCt | ddCt | F | Ct | Ctc | dCt | ddCt | F | Ct | Ctc | dCt | ddCt | F | Ct | Ctc | dCt | ddCt | F |
| 1N | 32.6 | 25.4 | 7.189 | | | 38.157 | 25.37 | 12.787 | | | 26.4 | 25.37 | 1.006 | | | 22.41 | 25.37 | -2.956 | | |
| 1T | 35 | 25.7 | 9.3 | 2.111 | 0.231 | 38.225 | 25.74 | 12.485 | -0.302 | 1.2329 | 28.4 | 25.74 | 2.683 | 1.677 | 0.31 | 25.79 | 25.74 | 0.051 | 3.007 | 0.12 |
| 2N | 30.1 | 26.7 | 3.417 | | | 33.347 | 26.725 | 6.622 | | | 27.1 | 26.73 | 0.356 | | | 23 | 26.725 | -3.729 | | |
| 2T | 33.9 | 27.6 | 6.311 | 2.894 | 0.135 | 40 | 27.618 | 12.382 | 5.76 | 0.0185 | 27.6 | 27.62 | -0.03 | -0.388 | 1.31 | 22.86 | 27.618 | -4.758 | -1.029 | 2.04 |
| 3N | 32.4 | 23.7 | 8.746 | | | 36.655 | 23.653 | 13.002 | | | 27.9 | 23.65 | 4.272 | | | 22.7 | 23.653 | -0.958 | | |
| 3T | 31 | 26.1 | 4.949 | -3.8 | 13.9 | 34.278 | 26.09 | 8.188 | -4.814 | 28.129 | 26.9 | 26.09 | 0.838 | -3.434 | 10.8 | 22.79 | 26.09 | -3.305 | -2.347 | 5.09 |
| 4N | 30 | 27.2 | 2.825 | | | 34.469 | 27.205 | 7.264 | | | 27.4 | 27.21 | 0.162 | | | 20.87 | 27.205 | -6.336 | | |
| 4T | 27.1 | 26.9 | 0.148 | -2.68 | 6.395 | 28.844 | 26.947 | 1.897 | -5.367 | 41.269 | 23.1 | 26.95 | -3.86 | -4.026 | 16.3 | 21.43 | 26.947 | -5.517 | 0.819 | 0.57 |
| 5N | 33.1 | 23.8 | 9.39 | | | 35.789 | 23.757 | 12.032 | | | 27.7 | 23.76 | 3.927 | | | 23 | 23.757 | -0.753 | | |
| 5T | 26.9 | 25.7 | 1.14 | -8.25 | 304.4 | 30.494 | 25.734 | 4.76 | -7.272 | 154.56 | 27.1 | 25.73 | 1.355 | -2.572 | 5.95 | 23.71 | 25.734 | -2.02 | -1.267 | 2.41 |
| 6N | 30.1 | 28.3 | 1.819 | | | 33.609 | 28.325 | 5.284 | | | 27.1 | 28.33 | -1.22 | | | 23.51 | 28.325 | -4.816 | | |
| 6T | 31.3 | 24.3 | 6.974 | 5.155 | 0.028 | 34.371 | 24.286 | 10.085 | 4.801 | 0.0359 | 28.1 | 24.29 | 3.777 | 4.993 | 0.03 | 22.94 | 24.286 | -1.346 | 3.47 | 0.09 |
| 7N | 29.8 | 19.8 | 10.04 | | | 35.867 | 19.76 | 16.107 | | | 26.7 | 19.76 | 6.917 | | | 22.18 | 19.76 | 2.418 | | |
| 7T | 27.3 | 20.4 | 6.853 | -3.19 | 9.132 | 31.273 | 20.441 | 10.832 | -5.275 | 38.72 | 24 | 20.44 | 3.547 | -3.37 | 10.3 | 20.95 | 20.441 | 0.508 | -1.91 | 3.76 |

FIG. 6B

| | | | | | | | | | | | | | | | | | | | |
|---|---|---|---|---|---|---|---|---|---|---|---|---|---|---|---|---|---|---|---|
| 8N | 31.1 | 23.3 | 7.864 | | | 37.31 | 23.255 | 14.055 | | | 27.2 | 23.26 | 3.938 | | | 22.56 | 23.255 | -0.7 | | |
| 8T | 27.3 | 22 | 5.316 | -2.55 | 5.848 | 31.282 | 22.021 | 9.261 | 4.794 | -27.742 | 27.1 | 22.02 | 5.042 | 1.104 | 0.47 | 21.33 | 22.021 | -0.688 | 0.012 | 0.99 |
| 9N | 31.1 | 21.5 | 9.617 | | | 35.079 | 21.452 | 13.627 | | | 25.8 | 21.45 | 4.32 | | | 22.15 | 21.452 | 0.696 | | |
| 9T | 35.9 | 28.1 | 7.747 | -1.87 | 3.655 | 45 | 28.115 | 16.885 | 3.258 | 0.1045 | 33.3 | 28.12 | 5.208 | 0.888 | 0.54 | 29.23 | 28.115 | 1.115 | 0.419 | 0.75 |
| 10N | 29.9 | 21.6 | 8.33 | | | 35.132 | 21.599 | 13.533 | | | 25.6 | 21.6 | 3.951 | | | 22.16 | 21.599 | 0.565 | | |
| 10T | 27.6 | 22.4 | 5.247 | -3.08 | 8.474 | 31.542 | 22.386 | 9.156 | 4.377 | 20.778 | 22.8 | 22.39 | 0.417 | 3.534 | 11.6 | 19.08 | 22.386 | -3.304 | 3.869 | 14.6 |
| 11N | 28.2 | 19.3 | 8.883 | | | 33.05 | 19.326 | 13.724 | | | 24.1 | 19.33 | 4.738 | | | 20.28 | 19.326 | 0.95 | | |
| 11T | 25.2 | 20 | 5.22 | -3.66 | 12.67 | 29.27 | 20.01 | 9.26 | 4.464 | 22.07 | 25 | 20.01 | 4.966 | 0.228 | 0.85 | 19.4 | 20.01 | -0.608 | 1.558 | 2.94 |
| 12N | 29.5 | 19.9 | 9.627 | | | 34.22 | 19.906 | 14.314 | | | 25.5 | 19.91 | 5.597 | | | 21.01 | 19.906 | 1.103 | | |
| 12T | 28.4 | 19.2 | 9.199 | -0.43 | 1.345 | 33.039 | 19.198 | 13.841 | 0.473 | 1.388 | 24.4 | 19.2 | 5.187 | -0.41 | 1.33 | 20.25 | 19.198 | 1.056 | 0.047 | 1.03 |
| 13N | 28.4 | 20.8 | 7.524 | | | 34.319 | 20.826 | 13.493 | | | 24.1 | 20.83 | 3.303 | | | 22 | 20.826 | 1.173 | | |
| 13T | 26.8 | 20.7 | 6.107 | -1.42 | 2.67 | 31.634 | 20.667 | 10.967 | 2.526 | -5.7597 | 24 | 20.67 | 3.315 | 0.012 | 0.99 | 20.91 | 20.667 | 0.245 | 0.928 | -1.9 |
| 14N | 32.4 | 25.9 | 6.494 | | | 36.882 | 25.898 | 10.984 | | | 28.8 | 25.9 | 2.95 | | | 27.05 | 25.898 | 1.153 | | |
| 14T | 30.3 | 18.5 | 11.86 | 5.368 | 0.024 | 35.073 | 18.474 | 16.599 | 5.615 | 0.0204 | 24.1 | 18.47 | 5.576 | 2.626 | 0.16 | 20.77 | 18.474 | 2.294 | 1.141 | 0.45 |
| 15N | 32.5 | 24.2 | 8.333 | | | 38.753 | 24.21 | 14.543 | | | 26.2 | 24.21 | 1.99 | | | 24.11 | 24.21 | 0.096 | | |
| 15T | 32.6 | 26.1 | 6.502 | -1.83 | 3.558 | 35.122 | 26.136 | 8.986 | 5.557 | 47.079 | 26.1 | 26.14 | 0.004 | 1.986 | 3.96 | 22.45 | 26.136 | -3.691 | 3.595 | 12.1 |
| 16N | 30.2 | 19.5 | 10.73 | | | 35.543 | 19.473 | 16.07 | | | 25.4 | 19.47 | 5.925 | | | 21.44 | 19.473 | 1.969 | | |
| 16T | 25.9 | 19.8 | 6.177 | -4.55 | 23.44 | 31.175 | 19.767 | 11.408 | 4.662 | -25.316 | 25.3 | 19.77 | 5.486 | 0.439 | 1.36 | 21.06 | 19.767 | 1.295 | 0.674 | 1.6 |
| 17N | 31.7 | 24.3 | 7.383 | | | 37.041 | 24.278 | 12.763 | | | 28.8 | 24.28 | 4.501 | | | 24.35 | 24.278 | 0.068 | | |
| 17T | 25.8 | 19.5 | 6.28 | -1.1 | 2.148 | 30.944 | 19.54 | 11.404 | 1.359 | -2.5651 | 23.2 | 19.54 | 3.708 | -0.793 | 1.73 | 20.19 | 19.54 | 0.654 | 0.586 | 0.67 |

FIG. 6B (Cont.)

|  | RASSF1m | | | | | BNC1m | | | | |
|---|---|---|---|---|---|---|---|---|---|---|
|  | Ctm | Ctu | dCt | ddCt | % | Ctm | Ctu | dCt | ddCt | % |
| 1N | 21.781 | 21.298 | 0.483 | | | 29.328 | 23.151 | 6.177 | | |
| 1T | 21.792 | 25.335 | -3.543 | -4.026 | 20.13 | 29.763 | 22.999 | 6.764 | 0.587 | 0 |
| 2N | 27.954 | 23.092 | 4.862 | | | 30.67 | 23.053 | 7.617 | | |
| 2T | 22.56 | 24.73 | -2.17 | -7.032 | 35.16 | 29.582 | 23.365 | 6.217 | -1.4 | 7 |
| 3N | 22.384 | 22.226 | 0.158 | | | 30.373 | 22.096 | 8.277 | | |
| 3T | 24.049 | 24.121 | -0.072 | -0.23 | 1.15 | 28.735 | 23.069 | 5.666 | -2.611 | 13.06 |
| 4N | 22.926 | 22.54 | 0.386 | | | 29.505 | 22.368 | 7.137 | | |
| 4T | 29.152 | 24.791 | 4.361 | 3.975 | 0 | 28.641 | 23.365 | 5.276 | -1.861 | 9.31 |
| 5N | 23.107 | 23.845 | -0.738 | | | 30.376 | 23.197 | 7.179 | | |
| 5T | 22.975 | 23.086 | -0.111 | 0.627 | 0 | 30.209 | 23.351 | 6.858 | -0.321 | 1.61 |
| 6N | 29.657 | 23.921 | 5.736 | | | 30.211 | 23.667 | 6.544 | | |
| 6T | 21.81 | 23.907 | -2.097 | -7.833 | 39.17 | 32.207 | 23.426 | 8.781 | 2.237 | 0 |
| 7N | 20.877 | 19.847 | 1.03 | | | 27.536 | 22.773 | 4.763 | | |
| 7T | 19.924 | 20.584 | -0.66 | -1.69 | 8.45 | 26.644 | 22.972 | 3.672 | -1.091 | 5.46 |
| 8N | 21.718 | 21.776 | -0.058 | | | 29.848 | 23.017 | 6.831 | | |
| 8T | 20.38 | 22.926 | -2.546 | -2.488 | 12.44 | 29.187 | 23.422 | 5.765 | -1.066 | 5.33 |
| 9N | 22.906 | 21.014 | 1.892 | | | 31.331 | 25.796 | 5.535 | | |
| 9T | 29.763 | 27.727 | 2.036 | 0.144 | 0 | 34.251 | 26.249 | 8.002 | 2.467 | 0 |
| 10N | 24.587 | 23.751 | 0.836 | | | 34.594 | 25.976 | 8.618 | | |
| 10T | 20.93 | 19.707 | 1.223 | 0.387 | 0 | 30.533 | 25.2 | 5.333 | -3.285 | 16.43 |
| 11N | 19.59 | 18.909 | 0.681 | | | 28.311 | 23.828 | 4.483 | | |
| 11T | 18.791 | 19.648 | -0.857 | -1.538 | 7.69 | 29.686 | 24.589 | 5.097 | 0.614 | 0 |
| 12N | 20.76 | 19.331 | 1.429 | | | 30.956 | 24.981 | 5.975 | | |
| 12T | 17.7 | 19.127 | -1.427 | -2.856 | 14.28 | 28.391 | 23.255 | 5.136 | -0.839 | 4.2 |

FIG. 6C

| | | | | | | | | | | |
|---|---|---|---|---|---|---|---|---|---|---|
| 13N | 22.599 | 19.691 | 2.908 | | | 32.512 | 25.37 | 7.142 | | |
| 13T | 21.478 | 20.172 | 1.306 | -1.602 | 8.01 | 31.369 | 25.992 | 5.377 | -1.765 | 8.83 |
| 14N | 23.905 | 24.396 | -0.491 | | | 32.76 | 26.409 | 6.351 | | |
| 14T | 18.428 | 21.16 | -2.732 | -2.241 | 11.21 | 30.334 | 23.694 | 6.64 | 0.289 | 0 |
| 15N | 25.427 | 28.673 | -3.246 | | | 30.37 | 25.998 | 4.372 | | |
| 15T | 28.345 | 30.999 | -2.654 | 0.592 | 0 | 30.003 | 24.839 | 5.164 | 0.792 | 0 |
| 16N | 32.584 | 33.702 | -1.118 | | | 28.656 | 24.527 | 4.129 | | |
| 16T | 36.28 | 40 | -3.72 | -2.602 | 13.01 | 27.249 | 24.375 | 2.874 | -1.255 | 6.28 |
| 17N | 26.722 | 23.621 | 3.101 | | | 32.186 | 27.175 | 5.011 | | |
| 17T | 18.443 | 18.22 | 0.223 | -2.878 | 14.39 | 25.596 | 25.649 | -0.053 | -5.064 | 25.32 |

FIG. 6C (Cont.)

| MALAT1 | | | | | ZFAS1 | | | | |
|---|---|---|---|---|---|---|---|---|---|
| Ct | Ctc | dCt | ddCt | F | Ct | Ctc | dCt | ddCt | F |
| 27.292 | 27.011 | 0.281 | | | 33.026 | 27.011 | 6.015 | | |
| 28.402 | 28.051 | 0.351 | 0.07 | 0.952638 | 34.972 | 28.051 | 6.921 | 0.906 | 0.533663 |
| 27.315 | 29.72 | -2.405 | | | 35.948 | 29.72 | 6.228 | | |
| 29.671 | 31.895 | -2.224 | 0.181 | 0.882091 | 42 | 31.895 | 10.105 | 3.877 | 0.068062 |
| 27.4 | 28.703 | -1.303 | | | 33.711 | 28.703 | 5.008 | | |
| 29.588 | 33.685 | -4.097 | -2.794 | 6.935501 | 42 | 33.685 | 8.315 | 3.307 | 0.10104 |
| 25.77 | 26.701 | -0.931 | | | 33.752 | 26.701 | 7.051 | | |
| 27.672 | 29.698 | -2.026 | -1.095 | 2.136131 | 36.975 | 29.698 | 7.277 | 0.226 | 0.855002 |
| 27.02 | 27.698 | -0.678 | | | 34.971 | 27.698 | 7.273 | | |
| 24.735 | 29.154 | -4.419 | -3.741 | 13.37067 | 33.679 | 29.154 | 4.525 | -2.748 | 6.717852 |
| 30.561 | 31.549 | -0.988 | | | 37.131 | 31.549 | 5.582 | | |
| 28.867 | 30.031 | -1.164 | -0.176 | 1.129747 | 35.259 | 30.031 | 5.228 | -0.354 | 1.278099 |
| 26.308 | 27.308 | -1 | | | 32.349 | 27.308 | 5.041 | | |

FIG. 6D

| 23.525 | 27.372 | -3.847 | -2.847 | 7.195026 | 33.506 | 27.372 | 6.134 | 1.093 | 0.468786 |
|---|---|---|---|---|---|---|---|---|---|
| 29.436 | 30.173 | -0.737 | | | 40 | 30.173 | 9.827 | | |
| 25.824 | 29.232 | -3.408 | -2.671 | 6.368705 | 35.169 | 29.232 | 5.937 | -3.89 | 14.82541 |
| 27.801 | 26.983 | 0.818 | | | 33.829 | 26.983 | 6.846 | | |
| 33.813 | 34.147 | -0.334 | -1.152 | 2.222217 | 42 | 34.147 | 7.853 | 1.007 | 0.49758 |
| 27.401 | 28.263 | -0.862 | | | 34.675 | 28.263 | 6.412 | | |
| 27.248 | 28.126 | -0.878 | -0.016 | 1.011152 | 34.261 | 28.126 | 6.135 | -0.277 | 1.211673 |
| 26.218 | 26.638 | -0.42 | | | 32.05 | 26.638 | 5.412 | | |
| 25.672 | 27.103 | -1.431 | -1.011 | 2.015308 | 30.955 | 27.103 | 3.852 | -1.56 | 2.948538 |
| 27.234 | 26.432 | 0.802 | | | 32.26 | 26.432 | 5.828 | | |
| 26.516 | 26.411 | 0.105 | -0.697 | 1.62113 | 31.815 | 26.411 | 5.404 | -0.424 | 1.341642 |
| 27.236 | 27.484 | -0.248 | | | 34.362 | 27.484 | 6.878 | | |
| 24.422 | 28.093 | -3.671 | -3.423 | 10.7257 | 33.773 | 28.093 | 5.68 | -1.198 | 2.294214 |
| 31.105 | 33.2 | -2.095 | | | 36.824 | 33.2 | 3.624 | | |
| 24.556 | 26.893 | -2.337 | -0.242 | 1.182631 | 32.197 | 26.893 | 5.304 | 1.68 | 0.312083 |
| 30.757 | 31.879 | -1.122 | | | 45 | 31.879 | 13.121 | | |
| 30.503 | 31.602 | -1.099 | 0.023 | 0.984184 | 45 | 31.602 | 13.398 | 0.277 | 0.825305 |
| 25.168 | 26.654 | -1.486 | | | 31.426 | 26.654 | 4.772 | | |
| 22.905 | 26.651 | -3.746 | -2.26 | 4.789915 | 30.574 | 26.651 | 3.923 | -0.849 | 1.801252 |
| 29.142 | 31.278 | -2.136 | | | 36.538 | 31.278 | 5.26 | | |
| 26.164 | 26.016 | 0.148 | 2.284 | 0.205328 | 31.284 | 26.016 | 5.268 | 0.008 | 0.99447 |

FIG. 6D (Cont.)

METHOD OF MULTIVARIATE MOLECULE ANALYSIS

CROSS REFERENCE TO RELATED APPLICATION

This application claims priority to International Application Serial No. PCT/US2015/048423 filed Sep. 3, 2015 which claims the benefit of priority to U.S. provisional application Ser. No. 62/045,917, filed on Sep. 4, 2014, both of which applications are incorporated herein by reference in their entirety.

SEQUENCE LISTING

A Sequence Listing is provided herewith as a text file, "MIOD-001US2_ST25.txt" created on Feb. 16, 2017 and having a size of 11 KB. The contents of the text file are incorporated by reference herein in their entirety.

TECHNICAL FIELD

The invention relates generally to analysis of a plurality of biomarkers which are associated with a particular disease such as a particular cancer for diagnosis, prognosis, and for allowing avoidance of unnecessary surgery.

INTRODUCTION

Cancer statistics indicate that about 12.7 million patients are suffering from various cancers (6.6 million men and 6.1 million women) in the world and this number will increase to 21 million by 2030. The most common cancers are lung, breast, colorectal, prostate, liver, bladder; kidney, cervix, pancreatic, gastric, brain, oral, endometrium, and ovary. Genetic biomarkers can be used for diagnosis and prognosis of cancers including but not limited to lung, breast, colorectal, prostate, liver, bladder; kidney, cervix, head, and ovarian cancers. There are currently no clinically available multivariate genetic biomarkers for early cancer detection. Further, once cancers are detected there is little information available to guide the therapy of patients with various cancers. Accordingly, there is a critical need for development of a set of biomarkers for both early detection and thereafter to assist in modulating therapy.

About 50% of newly diagnosed cancer patients undergo surgery that they may not need. Many of these surgeries can be eliminated by the use of genetic markers which can be used in an assay to provide early diagnosis, prognosis and/or treatment of various cancers.

SUMMARY

A multi-gene-based assay for analysis of the following: (a) oncogene expression; (b) DNA methylation of tumor suppressor genes; (c) non-coding RNA expression (microRNA profiling); and (d) long non-coding RNA expression in cancer samples is disclosed. The assay method and device for conducting the assay are applicable to diagnosis, prognosis, and treatment of various cancers such as lung, breast, colorectal, prostate, liver, bladder; kidney, cervix, pancreatic, gastric, brain, oral, endometrium, and ovary.

In certain embodiments, a method of analysis is provided. The method may include analyzing a sample obtained from a subject suspected of having cancer, the analyzing comprising: (a) determining level of expression of an oncogene; (b) determining level of DNA methylation of a tumor suppressor gene; (c) determining level of expression of a non-coding micro RNA (miRNA); (d) determining level of expression of a long non-coding RNA (lncRNA); (e) combining the levels from (a), (b), (c), and (d) to make a diagnosis, wherein the combining comprises comparing the level in each of (a), (b), (c), and (d) with a reference and determining a differential from that reference.

In certain embodiments, step (a) may include determining the level of expression of at least two oncogenes, step (b) may include determining the level of DNA methylation of at least two tumor suppressor genes, step (c) may include determining level of the expression of at least two miRNA; and (d) may include determining the level of expression of at least two lncRNA.

In certain embodiments, the oncogene is selected from the group consisting of: AMACR; SOX4; PSA; TMPRSS2; TWIST1; EZH2; PAP; PSCA; Akt; ERG; Ak2; c-myc; VEGF; MMP9; EGFR; CCND1; CCNE1; CCNA1; CA-199-9; EIF3; SIRT1; YAP1; AFP; Cox2; MTA1, MMP2, MMP7; CXCR3; PDGF; KLF5; KLF8; MMP1; CXCR7; NSE; hMLH1; PSMA; mTOR; PI3K; EZH2; and Survivin. The tumor suppressor gene may be selected from the group consisting of: RASSF1; TIG1; RARb; MDR1; ID4; GSTPI; SPON2; TIMP3; PTGS2; TIGI; BNIP3; AOX1; Clorf114; GAS6; HAPLN3; KLF8; BNC1, FZD1; RPL39L; SYN2; LMX1B1; CXXC5; APC; P16; HIC1; ANPEP; ABCA1; TET1; SFRP2, IGFBP7; KLK6; KLK10; EVX1; HIF3A; HAAO; HOXD3; TBX15; RASSF10; H4K20; H3K27; PITX21 CYP24A1; HINI; NKK2.5; CDH13; DPYS; PTGS2; EFEMP1; RGS2; SLC5A8; ZNF132; TSHZ3; AKAp12; EN1; SOCS3; WIF1; CRMP4; NKX3.1; CXCL14; and PTEN. miRNA may be selected from the group consisting of: miR-96, miR-205; miR-203; miR-31; miR-23b; miR-101; miR-708; miR-34b; miR-182, miR-151, miR-21, miR-888, miR-183, miR-106b-25, miR-31, miR-221, miR-222, miR-125b, miR-20a, miR-106b, miR-32, miR-16, miR-1, miR-204, miR-27b, hsa-let-7a, miR-101, miR-7, miR-155, miR-185, miR-200b, and miR-29b. The lncRNA may be selected from the group consisting of: GAS5, DD3, H19, HOTAIR, MALAT-1, HULA, PCGEM1, PRNCR1, PCAT1, PCAT18, PlncRNA-1, CTBP1-AS, PCA3; XIST; HOTTIP; ANRIL; AIRN; ICR1, PWR1, LINOCR, EVF2, NRON, ZEB2(NAT), Antisense UCHL1, BACE1AS, LINCMD1, HULC, IPS1, CDR1-AS, KCS1-AS, MEG3, MIAT, NDM29, RMRP, SRA-1, TERC, UCA1, Zfas1, CUDR, BIC, aHIF, and AK023948.

In certain cases, the subject may be suspected of having prostate cancer and step (a) may include assaying expression of AMACR and optionally SOX4, step (b) may include assaying DNA methylation of RASSF1, and optionally TIG1 and/or RARB, (c) may include assaying expression of miR-101 and optionally one or more of miR-205, miR-31, and miR-23b, and (d) may include assaying expression of MALAT1 and optionally ZFAS1. In certain cases, the combining (e) is carried out using an algorithm to calculate a score based on the differential for each of (a) to (d).

In certain cases, the results of each of (a)-(d) is represented by X, the reference is represented by Y, and the differential between X and Y is represented by Z, the diagnosis when Z's absolute value is 50% or more of X for at least two of (a)-(d) is an 80% or greater chance of surgery being required. In certain cases, when the results of each of (a)-(d) is represented by X, the reference is represented by Y, and the differential between X and Y is represented by Z, the diagnosis when Z's absolute value is 50% or more of X for at least three of (a)-(d) is a 90% or greater chance of surgery being required.

In other cases, the results of each of (a)-(d) is represented by X, the reference is represented by Y, and the differential between X and Y is represented by Z, the diagnosis when Z's absolute value is 50% or more of X for all four of (a)-(d) is a 98% or greater chance of surgery being required.

The assaying expression may be carried out using quantitative PCR performed in absence of a reporter probe complementary to a nucleic acid sequence of the oncogene, miRNA, or lncRNA. In some cases, formation of amplification product in the quantitative PCR is detected by intercalation of a dye into the amplification product.

In some cases assaying in (b) may be carried out using methylation specific PCR (MSP) and bisulfite genomic sequencing PCR (BSP).

In some cases, the (a), (b), (c) and (d) may be performed in a device comprising reagents for performing (a), (b), (c), and (d). In some cases, reagents for performing (a), (c) and (d) are disposed at a first location in the device and reagents for performing (b) are disposed at a second location in the device, wherein the first and second locations are physically separated.

Also disclosed herein is a method of analysis which includes analyzing a biological sample obtained from a subject suspected of having cancer, the analyzing comprising (a) assaying expression of an oncogene and determining a percentage chance of the subject having cancer based on oncogene detection; (b) assaying DNA methylation of a tumor suppressor gene and determining a percentage chance of the subject having cancer based on DNA methylation detection; (c) assaying expression of a non-coding miRNA and determining a percentage chance of the subject having cancer based on non-coding miRNA detection; (d) assaying expression of a long non-coding RNA and determining a percentage chance of the subject having cancer based on long non-coding miRNA detection; and (e) multiplying the percentage chance of (a) by the percentage chance of (b) to obtain a first product; multiplying the first product by the percentage chance of (c) to obtain a second product; and multiplying the second product by the percentage chance of (d) to obtain a final product; and (f) diagnosing the patient based on the final product.

In some cases, the diagnosing step (e) is based on a statistically significant number of prior assaying steps (a), (b), (c) and (d) carried out on a statistically significant number of prior subjects to determine a percentage chance of the subject having prostate cancer.

In some cases, the method may include analyzing a sample obtained from a human male subject suspected of having cancer, the analyzing comprising: (a) assaying expression of an oncogene; (b) assaying DNA methylation of a tumor suppressor gene; (c) assaying expression of a non-coding miRNA; (d) assaying expression of long non-coding RNA; and (e) analyzing result of each of (a), (b), (c) and (d) based on a statistically significant number of prior assaying steps (a), (b), (c), and (d) carried out on a statistically significant number of prior subjects to determine a percentage chance of the subject having prostate cancer.

Also provided herein is a method of prognosis; comprising: (a) obtaining a sample from a subject known to have prostate cancer; (b) assaying expression of an oncogene in the sample; (c) assaying DNA methylation of a tumor suppressor gene in the sample; (d) assaying expression of a non-coding RNA in the sample; (e) assaying expression of a long non-coding RNA (lncRNA) in the sample; (f) combining results of assaying of (b), (c), (d) and (e) to determine treatment of the subject. The oncogene may be selected from the group consisting of AMACR; SOX4; PSA; TMPRSS2; TWIST1; EZH2; PAP; PSCA; Akt; ERG; Ak2; c-myc; VEGF; MMP9; EGFR; CCND1; CCNE1; CCNA1; CA-199-9; EIF3; SIRT1; YAP1; AFP; Cox2; MTA1, MMP2, MMP7; CXCR3; PDGF; KLF5; KLF8; MMP1; CXCR7; NSE; hMLH1; PSMA; mTOR; PI3K; EZH2; and Survivin; the tumor suppressor gene may be selected from the group consisting of RASSF1; TIG1; RARb; MDR1; ID4; GSTPI; SPON2; TIMP3; PTGS2; TIGI; BNIP3; AOX1; C1orf114; GAS6; HAPLN3; KLF8; BNC1, FZD1; RPL39L; SYN2; LMX1B1; CXXC5; APC; P16; HIC1; ANPEP; ABCA1; TET1; SFRP2, IGFBP7; KLK6; KLK10; EVX1; HIF3A; HAAO; HOXD3; TBX15; RASSF10; H4K20; H3K27; PITX21 CYP24A1; HINI; NKK2.5; CDH13; DPYS; PTGS2; EFEMP1; RGS2; SLC5A8; ZNF132; TSHZ3; AKAp12; EN1; SOCS3; WIF1; CRMP4; NKX3.1; CXCL14; and PTEN; the miRNA may be selected from the group consisting of miR-96, miR-205; miR-31; miR-23b; miR-203; miR-101; miR-708; miR-34b; miR-182, miR-151, miR-21, miR-888, miR-183, miR-106b-25, miR-31, miR-221, miR-222, miR-125b, miR-20a, miR-106b, miR-32, miR-16, miR-1, miR-204, miR-27b, hsa-let-7a, miR-101, miR-7, miR-155, miR-185, miR-200b, and miR-29b; and the lncRNA may be selected from the group consisting of GAS5, DD3, H19, HOTAIR, MALAT-1, HULA, PCGEM1, PRNCR1, PCAT1, PCAT18, PlncRNA-1, CTBP1-AS, PCA3; XIST; HOTTIP; ANRIL; AIRN; ICR1, PWR1, LINOCR, EVF2, NRON, ZEB2(NAT), antisense UCHL1, BACE1AS, LINCMD1, HULC, IPS1, CDR1-AS, KCS1-AS, MEG3, MIAT, NDM29, RMRP, SRA-1, TERC, UCA1, Zfas1, CUDR, BIC, aHIF, and AK023948.

In certain embodiments, a method of determining treatment of a subject having prostate cancer or suspected of having prostate cancer (e.g., a subject at risk of developing prostate cancer), the method comprising: (i) assaying a biological sample from prostate cancer patient for: (a) level of expression of at least one of oncogenes AMACR, SOX4, TMPRSS2, TWIST1, PSA and PAP; (b) level of DNA methylation of at least one of tumor suppressor genes RASSF1, TIG1, RARb, MDR1, and ID4; (c) level of expression of at least one of miRNAs miR-96, miR-205, miR-31, miR-23b, miR-101 and miR-185; and (d) level of expression of at least one of lncRNAs ZFAS1 and MALAT1; (ii) comparing the levels to the levels from a normal reference; and (iii) determining the treatment of the subject based on the comparing (ii).

In certain cases, the determining the treatment comprises determining that the subject requires surgery to remove prostate tissue when: expression of at least one of the oncogenes AMACR, SOX4, TMPRSS2, TWIST1, PSA and PAP is increased by about 5 fold and others (EZH2; PSCA; Akt; ERG; Ak2; c-myc; VEGF; MMP9; EGFR; CCND1; CCNE1; CCNA1; CA-199-9; EIF3; SIRT1; YAP1; AFP; Cox2; MTA1, MMP2, MMP7; CXCR3; PDGF; KLF5; KLF8; MMP1; CXCR7; NSE; hMLH1; PSMA; mTOR; PI3K; EZH2) is increased by about 2 fold; DNA methylation of at least one of tumor suppressor genes RASSF1, TIG1, RARb, MDR1, and ID4 is increased by about 50%; expression of at least one of miRNAs miR-205, miR-31, miR-23b, miR-101 and miR-185 is reduced by about 2 folds; and expression of at least one of long non-coding RNAs ZFAS1 and MALAT1 is unchanged or increased by about 2 folds.

In certain cases, the determining the treatment comprises determining that the subject requires surgery to remove prostate tissue when expression of the oncogenes AMACR, SOX4, TMPRSS2, TWIST1, PSA and PAP is unchanged; DNA methylation of at least one of tumor suppressor genes RASSF1, TIG1, RARb, MDR1, and ID4 is increased by about 50%; expression of at least one of miRNAs miR-205, miR-31, miR-23b, miR-101 and miR-185 is reduced by about 2 folds; and expression of at least one of long non-coding RNAs ZFAS1 and MALAT1 is increased by about 2 folds.

In certain cases, the determining the treatment comprises determining that the subject requires surgery to remove prostate tissue when expression of at least one of the oncogenes AMACR, SOX4, TMPRSS2, TWIST1, PSA and PAP is increased by about 5 fold and others (EZH2; PSCA; Akt; ERG; Ak2; c-myc; VEGF; MMP9; EGFR; CCND1; CCNE1; CCNA1; CA-199-9; EIF3; SIRT1; YAP1; AFP; Cox2; MTA1, MMP2, MMP7; CXCR3; PDGF; KLF5; KLF8; MMP1; CXCR7; NSE; hMLH1; PSMA; mTOR; PI3K; EZH2) is increased by about 2 fold; DNA methylation of tumor suppressor genes RASSF1, TIG1, RARb, MDR1, and ID4 is unchanged; expression of at least one of miRNAs miR-205, miR-31, miR-23b, miR-101 and miR-185 is reduced by about 2 folds; and expression of at least one of long non-coding RNAs ZFAS1 and MALAT1 is unchanged or increased by about 2 folds.

In certain cases, the determining the treatment comprises determining that the subject does not require surgery to remove prostate tissue and requires active surveillance when expression of the oncogenes AMACR, SOX4, TMPRSS2, TWIST1, PSA and PAP is unchanged; DNA methylation of tumor suppressor genes RASSF1, TIG1, RARb, MDR1, and ID4 is unchanged; expression of at least one of miRNAs miR-205, miR-31, miR-23b, miR-101 and miR-185 is reduced by about 2 folds; and expression of at least one of long non-coding RNAs ZFAS1 and MALAT1 is increased by about 2 folds.

In certain cases, the determining the treatment comprises determining that the subject does not require surgery to remove prostate tissue and requires active surveillance when expression of the oncogenes AMACR, SOX4, TMPRSS2, TWIST1, PSA and PAP is unchanged; DNA methylation of at least one tumor suppressor gene: RASSF1, TIG1, RARb, MDR1, and ID4 is increased by about 50%; expression of at least one of miRNAs miR-205, miR-31, miR-23b, miR-101 and miR-185 is reduced by about 2 folds; and expression of at least one of long non-coding RNAs ZFAS1 and MALAT1 is increased by about 2 folds.

In certain cases, the determining the treatment comprises determining that the subject does not require surgery to remove prostate tissue and requires active surveillance when expression of at least one of the oncogenes AMACR, SOX4, TMPRSS2, TWIST1, PSA and PAP is increased by less than about 5-fold; DNA methylation of at least one tumor suppressor gene: RASSF1, TIG1, RARb, MDR1, and ID4 is increased by less than 50%; expression of miRNAs miR-205, miR-31, miR-23b, miR-101 and miR-185 is unchanged; and expression of long non-coding RNAs ZFAS1 and MALAT1 is unchanged.

The normal reference may be the expression and methylation status in sample of the same type from subjects not having cancer. In other cases, normal reference is the expression and methylation status in non-cancerous sample from the patients. In other cases, the normal reference is the expression level of the genes/RNA disclosed herein and methylation status in non-cancerous sample of tissue of the same type as the cancerous sample from the subject having or suspected of having cancer. In some cases, the sample may be a blood sample that contains circulating prostate tumor cells and normal prostate cells and the comparison of level of expression and methylation of the gene/RNA disclosed herein may be between the tumor cells and normal cells. In some cases, the sample may be a prostate tissue sample from a prostate cancer patient or from a patient suspected of having prostate cancer or is at risk of developing prostate cancer and the comparison may be between normal appearing cells and cancerous appearing cells in a prostate tissue sample from the patient.

Also provided herein is a method of determining treatment of a subject having kidney cancer, the method comprising (i) assaying a sample from the subject for (a) level of expression of oncogenes CCND1 and EGFR; (b) level of DNA methylation of tumor suppressor genes TIG1 and BNC1; (c) level of expression of oncogenic miRNAs miR-21 and miR210 and tumor suppressor miRNAs, miR-23b and miR-34b; and (d) level of expression of lncRNA ZFAS1; (ii) comparing the expression and methylation status to a normal reference; and (iii) determining the treatment of the subject based on the comparing (ii).

In certain cases, the determining the treatment comprises determining that the subject requires surgery to remove kidney tissue when expression of one of the oncogenes CCND1 and EGFR is increased by about 2 fold and the other is unchanged; DNA methylation of at least one of tumor suppressor genes TIG1 and BNC1 is increased by about 50%; expression of at least one of oncogenic miRNAs miR-21 and miR210 is increased by about 1.5 folds; expression of at least one of the tumor suppressor miRNAs miR-23b and miR-34b is decreased by 1.5 fold; and expression of lncRNA ZFAS1 is unchanged or increased by about 2 folds.

In certain cases, the determining the treatment comprises determining that the subject requires surgery to remove kidney tissue when expression of the oncogenes CCND1 and EGFR is unchanged; DNA methylation of at least one of tumor suppressor genes TIG1 and BNC1 is increased by about 50%; expression of at least one of miRNAs miR-21 and miR210 is increased by about 2 folds; expression of at least one of the tumor suppressed miRNAs miR-23b and miR-34b are decreased by 1.5 fold; and expression of lncRNA ZFAS1 is increased by about 2 folds.

In certain cases, the determining the treatment comprises determining that the subject requires surgery to remove kidney tissue when expression of at least one of the oncogenes CCND1 and EGFR increased by about 2 fold; DNA methylation of tumor suppressor genes TIG1 and BNC1 is unchanged; expression of at least one of miRNAs miR-21 and miR210 is increased by about 1.5 folds; and expression of lncRNA ZFAS1 is increased by about 2 folds.

In certain cases, the determining the treatment comprises determining that the subject requires surgery to remove kidney tissue when expression of one of the oncogenes CCND1 and EGFR is increased by about 2 fold and the other is unchanged; DNA methylation of at least one of tumor suppressor genes TIG1 and BNC1 is increased by about 50%; expression of oncogenic miRNAs miR-21 and miR210 is unchanged; and expression of lncRNA ZFAS1 is unchanged.

In certain cases, the determining the treatment comprises determining that the subject does not require surgery to remove kidney tissue and requires active surveillance when expression of the oncogenes CCND1 and EGFR is unchanged; DNA methylation of tumor suppressor genes TIG1 and BNC1 is unchanged; expression of at least one of miRNAs miR-21 and miR210 by increased about 1.5 folds; expression of at least one of the tumor suppressed miRNAs miR-23b and miR-34b are decreased by 1.5 fold; and expression of lncRNA ZFAS1 is increased by about 2 folds.

The normal reference may be the levels (of expression and DNA methylation of the gene assayed) in kidney tissue from subjects not having cancer. The normal reference may be the levels (expression and methylation status of the assayed genes) in non-cancerous kidney tissue from kidney cancer patients. The normal reference may be the levels (expression and methylation status of the assayed genes) in non-cancerous kidney tissue from the subject having kidney cancer.

In other embodiments, a method of diagnosing a subject suspected of having prostate cancer is provided, the method comprising determining expression of miR-96 in prostate tissue sample of the subject to determine a miR-96 expression level; using the miR-96 expression level to diagnose the subject, wherein an increased miR-96 expression level in the prostate tissue sample compared to a miR-96 reference level is indicative of prostate cancer.

In some cases, the miR-96 reference level may be miR-96 expression level in prostate tissue from subjects not having prostate cancer. In some cases, the miR-96 reference level may be miR-96 expression level in non-cancerous prostate tissue from subjects having prostate cancer. In some cases, the miR-96 reference level may miR-96 expression level in non-cancerous prostate tissue from the subject suspected of having cancer.

In some cases, the determining comprises assaying expression of miR-96 in cells in prostate tissue sample of the subject, wherein the cells have a phenotype suggestive of cancerous cells.

In some cases, the non-cancerous prostate tissue is identified as non-cancerous based on phenotype of the cells. The phenotype may be appearance of one or more of nuclei, cell membrane, cell shape, and cell volume. In some cases, a cell stain may be used to stain the cells to distinguish cancer cells from normal cells. The staining may be hematoxylin and eosin staining or another stain.

In some cases, in addition to determining the level of expression of miR-96, the method may further comprises assaying expression level of an oncogene and a long non-coding RNA (lncRNA), and assaying DNA methylation of a tumor suppressor gene. The oncogene may be selected from the group consisting of AMACR; SOX4; PSA; TMPRSS2; TWIST1; EZH2; PAP; PSCA; Akt; ERG; Ak2; c-myc; VEGF; MMP9; EGFR; CCND1; CCNE1; CCNA1; CA-199-9; EIF3; SIRT1; YAP1; AFP; Cox2; MTA1; MMP2; MMP7; CXCR3; PDGF; KLF5; KLF8; MMP1; CXCR7; NSE; hMLH1; PSMA; mTOR; PI3K; EZH2; and Survivin; wherein the tumor suppressor gene is selected from the group consisting of RASSF1; TIG1; RARb; MDR1; ID4; GSTPI; SPON2; TIMP3; PTGS2; TIGI; BNIP3; AOX1; C1orf114; GAS6; HAPLN3; KLF8; BNC1; FZD1; RPL39L; SYN2; LMX1B1; CXXC5; APC; P16; HIC1; ANPEP; ABCA1; TET1; SFRP2; IGFBP7; KLK6; KLK10; EVX1; HIF3A; HAAO; HOXD3; TBX15; RASSF10; H4K20; H3K27; PITX21 CYP24A1; HINI; NKK2.5; CDH13; DPYS; PTGS2; EFEMP1; RGS2; SLC5A8; ZNF132; TSHZ3; AKAp12; EN1; SOCS3; WIF1; CRMP4; NKX3.1; CXCL14; and PTEN; and wherein the lncRNA is selected from the group consisting of GAS5, DD3, H19, HOTAIR, MALAT-1, HULA, PCGEM1, PRNCR1, PCAT1, PCAT18, PlncRNA-1, CTBP1-AS, PCA3; XIST; HOTTIP; ANRIL; AIRN; ICR1, PWR1, LINOCR, EVF2, NRON, ZEB2 (NAT), Antisense UCHL1, BACE1AS, LINCMD1, HULC, IPS1, CDR1-AS, KCS1-AS, MEG3, MIAT, NDM29, RMRP, SRA-1, TERC, UCA1, Zfas1, CUDR, BIC, aHIF, and AK023948.

In certain cases, the oncogene is selected from the group consisting of AMACR, SOX4, and TWIST1; the tumor suppressor gene is selected from the group consisting of RASSF1, RARB, and TIG1; and the lncRNA is selected from the group consisting of MALAT1 and ZFAS1.

In certain cases, the oncogene is AMACR, the tumor suppressor gene is RASSF1, and the lncRNA is MALAT1.

A method for avoidance of surgical removal of cancer tissue in a patient is provided. The method comprising normal cells and tumor cells in a biological sample from the patient for the level of (a) expression level of an oncogene; (b) DNA methylation of a tumor suppressor gene; (c) expression level of a non-coding micro RNA (miRNA); (d) expression level of a long non-coding RNA (lncRNA); (e) comparing the level in each of (a), (b), (c), and (d) between the cancer cells and the normal cells to determine a difference between the levels between cancer cells and normal cells; and (ii) avoiding surgery to remove cancer tissue based on the difference in the levels between cancer cells and normal cells. For example, when there is no significant difference in the levels in at least one of (a), (b), (c), and (d) between the cancer cells and normal cells, surgical removal of the cancer tissue is avoided.

In certain cases, the cancer may be prostate cancer, and the normal and cancer cells may be prostate cells (e.g., circulating prostate cells present in a blood sample of the subject or cells in a biopsy sample of prostate tissue). In certain cases, the level of expression of at least one of oncogenes AMACR, SOX4, TMPRSS2, TWIST1, PSA and PAP; DNA methylation of at least one of tumor suppressor genes RASSF1, TIG1, RARB, MDR1, and ID4; expression of at least one of miRNAs miR-96, miR-205, miR-31, miR-23b, miR-101 and miR-185; and expression of at least one of lncRNAs ZFAS1 and MALAT1 is determined; wherein the method comprises determining that the subject can avoid the surgical removal of prostate cancer tissue when expression of the oncogenes AMACR, SOX4, TMPRSS2, TWIST1, PSA and PAP is unchanged; DNA methylation of tumor suppressor genes RASSF1, TIG1, RARb, MDR1, and ID4 is unchanged; expression of at least one of miRNAs miR-205, miR-31, miR-23b, miR-101 and miR-185 is reduced by about 2 folds; and expression of at least one of long non-coding RNAs ZFAS1 and MALAT1 is increased by about 2 folds or when the level of: expression of the oncogenes AMACR, SOX4, TMPRSS2, TWIST1, PSA and PAP is unchanged; DNA methylation of at least one tumor suppressor gene: RASSF1, TIG1, RARb, MDR1, and ID4 is increased by about 50%; expression of at least one of miRNAs miR-205, miR-31, miR-23b, miR-101 and miR-185 is reduced by about 2 folds; and expression of at least one of long non-coding RNAs ZFAS1 and MALAT1 is increased by about 2 folds.

The subject can also avoid surgical removal of prostate tissue when the level of: expression of at least one of the oncogenes AMACR, SOX4, TMPRSS2, TWIST1, PSA and PAP is increased by less than about 5-fold; DNA methylation of at least one tumor suppressor gene: RASSF1, TIG1, RARb, MDR1, and ID4 is increased by less than 50%; expression of miRNAs miR-205, miR-31, miR-23b, miR-101 and miR-185 is unchanged; and expression of long non-coding RNAs ZFAS1 and MALAT1 is unchanged.

Also provided herein is a method of determining risk of mortality in a prostate cancer patient, the method comprising assaying cancer cells and normal cells in prostate tissue obtained from the prostate cancer patient to determine expression level of oncogene AMACR; the level of DNA methylation of tumor suppressor gene RASSF1; expression level of miR-101; and expression level of lncRNA MALAT1, determining risk of mortality of the prostate cancer patient, wherein when expression level of only one or none of: AMACR, miR-101, MALAT1 and DNA methylation of RASSF1 in the cancer cells is unchanged relative to the normal cells, the prostate cancer patient has no risk of mortality over the next 5 years; wherein when expression level of only two of: AMACR, miR-101, MALAT1 and DNA methylation of RASSF1 in the cancer cells is changed relative to the normal cells, the prostate cancer patient has low risk of mortality over the next 5 years; wherein when expression level of only three or all four of: AMACR, miR-101, MALAT1 and DNA methylation of RASSF1 in the cancer cells is changed relative to the normal cells, the prostate cancer patient has increased risk of mortality over the next 5 years.

A method of determining treatment of a subject having colon cancer is also provided, the method comprising: (i) assaying a tumor sample from the subject for: (a) expression of oncogenes TWIST1, CCND1, MET and SOX4; (b) DNA methylation of tumor suppressor genes OSMA, SFRP1, MGMT, TIMP3, BNC1 and RARB; (c) expression of oncogenic miRNAs miR-182, miR-183, miR-21 and miR210; and (d) expression of lncRNA H19; (ii) comparing the expression and methylation status to a normal reference; and (iii) determining the treatment of the subject based on the comparing (ii).

In certain cases, the determining the treatment comprises determining that the subject requires surgery to remove colon tissue when the level of expression of one of the oncogenes TWIST1, CCND1, MET and SOX4 is increased by about 2 fold and the others are unchanged; DNA methylation of at least one of tumor suppressor genes OSMA, SFRP1, MGMT, TIMP3, BNC1 and RARb is increased by about 20%; expression of at least one of oncogenic miRNAs miR-182, miR-183, miR-21 and miR210 is increased by about 2 folds; and expression of lncRNA H19 is unchanged or increased by about 4 folds.

In certain cases, the determining the treatment comprises determining that the subject requires surgery to remove colon tissue when the level of: expression of the oncogenes TWIST1, CCND1, MET and SOX4 is unchanged; DNA methylation of at least one of tumor suppressor genes OSMA, SFRP1, MGMT, TIMP3, BNC1 and RARb is increased by about 20%; expression of at least one of miRNAs miR-182, miR-183, miR-21 and miR210 is increased by about 2 folds; and expression of lncRNA H19 is increased by about 4 folds.

In certain cases, the determining the treatment comprises determining that the subject requires surgery to remove colon tissue when the level of: expression of at least one of the oncogenes TWIST1, CCND1, MET and SOX4 increased by about 2 fold; DNA methylation of tumor suppressor genes OSMA, SFRP1, MGMT, TIMP3, BNC1 and RARb is unchanged; expression of at least one of miRNAs miR-182, miR-183, miR-21 and miR210 is increased by about 2 folds; and expression of lncRNA H19 is increased by about 4 folds.

In certain cases, the determining the treatment comprises determining that the subject requires surgery to remove colon tissue when the level of: expression of one of the oncogenes TWIST1, CCND1, MET and SOX4 is increased by about 2 fold and the other is unchanged; DNA methylation of at least one of tumor suppressor genes OSMA, SFRP1, MGMT, TIMP3, BNC1 and RARb is increased by about 20%; expression of oncogenic miRNAs miRNAs miR-182, miR-183, miR-21 and miR210 is unchanged; and expression of lncRNA H19 is unchanged.

In certain cases, the determining the treatment comprises determining that the subject does not require surgery to remove colon tissue and requires active surveillance (e.g., assessing the levels of the genes mentioned herein) when: expression of the oncogenes TWIST1, CCND1, MET and SOX4 is unchanged; DNA methylation of tumor suppressor genes OSMA, SFRP1, MGMT, TIMP3, BNC1 and RARb is unchanged; expression of at least one of miRNAs miR-182, miR-183, miR-21 and miR210 by increased about 2 folds; and expression of lncRNA H19 is increased by about 4 folds.

In certain cases, the normal reference is the level of the expression and methylation status in colon tissue from subjects not having cancer. In certain cases, the normal reference is the level of the expression and methylation status in non-cancerous colon tissue from colon cancer patients. In certain cases, the normal reference is the level of the expression and methylation status in non-cancerous colon tissue from the subject having colon cancer.

Also disclosed is a method of determining treatment of a subject having lung cancer, the method comprising: (i) assaying a tumor sample from lung tissue of the subject for the level of: (a) expression of oncogenes TWIST1 and MET; (b) DNA methylation of tumor suppressor genes BNC1, MGMT, RASSF1, and SFRP1; (c) expression of oncogenic miRNAs miR-210, miR-182, and miR-21; and (d) expression of lncRNA MALAT1; (ii) comparing the expression and methylation status to a normal reference; and (iii) determining the treatment of the subject based on the comparing (ii).

In certain cases, the determining the treatment comprises determining that the subject requires surgery to remove lung tissue when the level of: expression of one of the oncogenes TWIST1 and MET is increased by about 2 fold and the other is unchanged; DNA methylation of at least one of tumor suppressor genes MGMT, RASSF1, and SFRP1 is increased by about 20%; expression of at least one of oncogenic miRNAs miR-210, miR-182, and miR-21 is increased by about 2 folds; and expression of lncRNA MALAT1 is unchanged or increased by about 4 folds.

In certain cases, the determining the treatment comprises determining that the subject requires surgery to remove lung tissue when the level of: expression of the oncogenes TWIST1 and MET is unchanged; DNA methylation of at least one of tumor suppressor genes MGMT, RASSF1, and SFRP1 is increased by about 20%; expression of at least one of miRNAs miR-210, miR-182, and miR-21 is increased by about 2 folds; and expression of lncRNA MALAT1 is increased by about 4 folds.

In certain cases, the determining the treatment comprises determining that the subject requires surgery to remove lung tissue when the level of: expression of at least one of the oncogenes TWIST1 and MET increased by about 2 fold; DNA methylation of tumor suppressor genes MGMT, RASSF1, and SFRP1 is unchanged; expression of at least one of miRNAs miR-210, miR-182, and miR-21 is increased is increased by about 2 folds; and expression of lncRNA MALAT1 is increased by about 4 folds.

In certain cases, the determining the treatment comprises determining that the subject requires surgery to remove lung tissue when the level of: expression of one of the oncogenes TWIST1 and MET is increased by about 2 fold and the other is unchanged; DNA methylation of at least one of tumor suppressor genes MGMT, RASSF1, and SFRP1 is increased by about 20%; expression of oncogenic miRNAs miRNAs miR-210, miR-182, and miR-21 is unchanged; and expression of lncRNA MALAT1 is unchanged.

In certain cases, the determining the treatment comprises determining that the subject does not require surgery to remove lung tissue and requires active surveillance (e.g., determination of the level of expression and methylation of the genes disclosed herein) when the level of: expression of the oncogenes TWIST1 and MET is unchanged; DNA methylation of tumor suppressor genes MGMT, RASSF1, and SFRP1 is unchanged; expression of at least one of miRNAs miR-210, miR-182, and miR-21 by increased about 2 folds; and expression of lncRNA MALAT1 is increased by about 4 folds.

In certain cases, the normal reference is the level of expression and methylation status in lung tissue from subjects not having cancer. In certain cases, the normal reference is the level of expression and methylation status in non-cancerous lung tissue from lung cancer patients. In certain cases, the normal reference is the level of expression and methylation status in non-cancerous lung tissue from the subject having lung cancer.

Also disclosed herein is a method of determining treatment of a subject having liver cancer, the method comprising: (i) assaying a tumor sample from liver tissue of the subject for level of: (a) expression of oncogenes SOX4, AMACR, MET, MMP2, and EGFR; (b) DNA methylation of tumor suppressor genes BNC1 and RASSF1; (c) expression of oncogenic miRNAs miR-182, miR-183, miR-222, and miR-21; and (d) expression of lncRNA ZFAS1, and MALAT1; (ii) comparing the expression and methylation status to a normal reference; and (iii) determining the treatment of the subject based on the comparing (ii).

In certain cases, the determining the treatment comprises determining that the subject requires surgery to remove liver tissue when: expression of one of the oncogenes SOX4, AMACR, MET, MMP2, and EGFR is increased by about 2 fold and the other is unchanged; DNA methylation of at least one of tumor suppressor genes BNC1 and RASSF1 is increased by about 10%; expression of at least one of oncogenic miRNAs miR-182, miR-183, miR-222, and miR-21 is increased by about 2 folds; and expression of lncRNA ZFAS1, and MALAT1 is unchanged or increased by about 2 folds.

In certain cases, the determining the treatment comprises determining that the subject requires surgery to remove liver tissue when expression of the oncogenes SOX4, AMACR, MET, MMP2, and EGFR is unchanged; DNA methylation of at least one of tumor suppressor genes BNC1 and RASSF1 is increased by about 10%; expression of at least one of miRNAs miR-182, miR-183, miR-222, and miR-21 is increased by about 2 folds; and expression of lncRNA ZFAS1, and MALAT1 is increased by about 2 folds.

In certain cases, the determining the treatment comprises determining that the subject requires surgery to remove liver tissue when: expression of at least one of the oncogenes SOX4, AMACR, MET, MMP2, and EGFR increased by about 2 fold; DNA methylation of tumor suppressor genes BNC1 and RASSF1 is unchanged; expression of at least one of miRNAs miR-182, miR-183, miR-222, and miR-21 is increased is increased by about 2 folds; and expression of lncRNA ZFAS1, and MALAT1 is increased by about 2 folds.

In certain cases, the determining the treatment comprises determining that the subject requires surgery to remove liver tissue when: expression of one of the oncogenes SOX4, AMACR, MET, MMP2, and EGFR is increased by about 2 fold and the other is unchanged; DNA methylation of at least one of tumor suppressor genes BNC1 and RASSF1 is increased by about 10%; expression of oncogenic miRNAs miR-182, miR-183, miR-222, and miR-21 is unchanged; and expression of lncRNA ZFAS1, and MALAT1 is unchanged.

In certain cases, the determining the treatment comprises determining that the subject does not require surgery to remove liver tissue and requires active surveillance when: expression of the oncogenes SOX4, AMACR, MET, MMP2, and EGFR is unchanged; DNA methylation of tumor suppressor genes BNC1 and RASSF1 is unchanged; expression of at least one of miRNAs miR-182, miR-183, miR-222, and miR-21 by increased about 2 folds; and expression of lncRNA ZFAS1, and MALAT1 is increased by about 4 folds.

In certain cases, the normal reference is the expression and methylation status in liver tissue from subjects not having cancer. In certain cases, the normal reference is the expression and methylation status in non-cancerous liver tissue from liver cancer patients. In certain cases, the normal reference is the expression and methylation status in non-cancerous liver tissue from the subject having liver cancer.

In certain cases, the normal cells and cancerous cells that are assayed for determining the level of expression and methylation of the genes disclosed herein may be the same type of cells. These cells may be cells present in a biopsy sample such as liquid biopsy sample or solid tissue biopsy sample (e.g., blood sample or a solid tissue sample) of the patient diagnosed as having the cancer, suspected of having the cancer, or susceptible to developing the cancer. The normal cells and tumor cells may be distinguished by cell staining. The normal cells and tumor cells may be separated by fluorescence activated cell soring or by microdissection. Thus for example, the normal cells and cancer cells may be circulating kidney cells or cells obtained by microdissection (e.g., laser microdissection) of a kidney tissue sample.

BRIEF DESCRIPTION OF THE DRAWINGS

FIGS. 1A-1D provide fold change in expression level of oncogenes (FIG. 1A), percent DNA methylation change (FIG. 1B), fold change in expression level of miRNA (FIG. 1C), fold change in expression level of lncRNA (FIG. 1D) in prostate cancer tissue and Gleason score, pT, and survival (FIG. 1D) of the patient.

FIGS. 2A-2E provide expression level of oncogenes (FIG. 2A), expression level of miRNA (FIGS. 2B and 2C), percent DNA methylation (FIG. 2D), and expression level of lnRNA (FIG. 2E) in normal (N) and tumor (T) kidney tissue from kidney cancer patients.

FIG. 3 shows that miR-96 expression is increased in cancer cells in prostate tissue as compared to normal cells in prostate tissue. N=normal cells; T=cancer cells.

FIGS. 4A-4D provide expression level of oncogenes (FIG. 4A), expression level of miRNA (FIG. 4B), percent DNA methylation (FIG. 4C), and expression level of lncRNA (FIG. 4D) in normal (N) and tumor (T) colon tissue from colon cancer patients FIGS. 5A-5D provide expression level of oncogenes (FIG. 5A), expression level of miRNA (FIG. 5B), percent DNA methylation (FIG. 5C), and expression level of lncRNA (FIG. 5D) in normal (N) and tumor (T) lung tissue from lung cancer patients.

FIGS. 6A-6D provide expression level of oncogenes (FIG. 6A), expression level of miRNA (FIG. 6B), percent DNA methylation (FIG. 6C), and expression level of lncRNA (FIG. 6D) in normal (N) and tumor (T) liver tissue from liver cancer patients.

DEFINITIONS

Figure 1E:
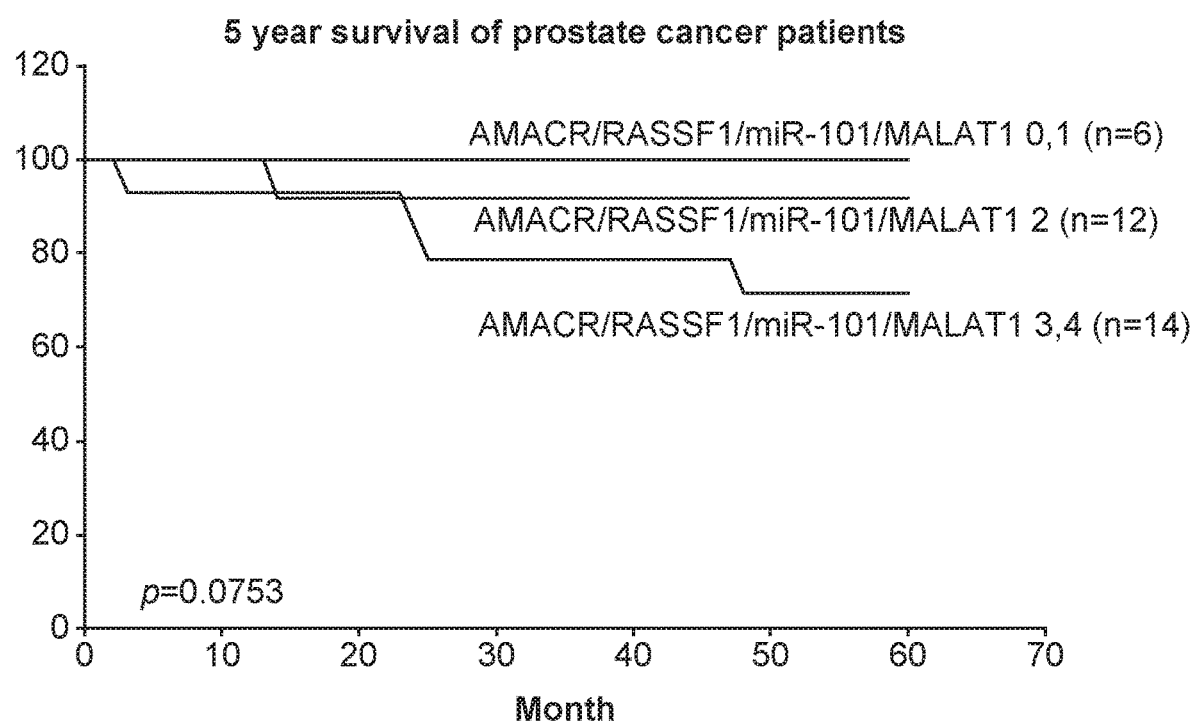
FIG. 1E shows 60 months survival curve of the prostate cancer patients after surgery.

The terms "tumor" and "lesion" as used herein, refer to all neoplastic cell growth and proliferation, and all pre-cancerous and cancerous cells and tissues. Those skilled in the art will realize that a tumor tissue sample may comprise multiple biological elements, such as one or more cancer cells, partial or fragmented cells, tumors in various stages, surrounding histologically normal-appearing tissue, and/or macro or micro-dissected tissue.

The terms "cancer" and "cancerous" refer to or describe the physiological condition in mammals that is typically characterized by unregulated cell growth.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the term "prostate cancer" is used in the broadest sense refers to all stages and all forms of cancer arising from the tissue of the prostate gland.

The Gleason Grading system is used to help evaluate the prognosis of men with prostate cancer. Together with other parameters, it is incorporated into a strategy of prostate cancer staging, which predicts prognosis and helps guide therapy. A Gleason "score" or "grade" is given to prostate cancer based upon its microscopic appearance. Tumors with a low Gleason score typically grow slowly enough that they may not pose a significant threat to the patients in their lifetimes. These patients are monitored ("watchful waiting" or "active surveillance") over time. Cancers with a higher Gleason score are more aggressive and have a worse prognosis, and these patients are generally treated with surgery (e.g., radical prostatectomy) and, in some cases, therapy (e.g., radiation, hormone, ultrasound, chemotherapy). Gleason scores (or sums) comprise grades of the two most common tumor patterns. These patterns are referred to as Gleason patterns 1-5, with pattern 1 being the most well-differentiated. Most have a mixture of patterns. To obtain a Gleason score or grade, the dominant pattern is added to the second most prevalent pattern to obtain a number between 2 and 10. The Gleason Grades include: G1: well differentiated (slight anaplasia) (Gleason 2-4); G2: moderately differentiated (moderate anaplasia) (Gleason 5-6); G3-4: poorly differentiated/undifferentiated (marked anaplasia) (Gleason 7-10).

As used herein, the term "tumor tissue" refers to a biological sample containing one or more cancer cells, or a fraction of one or more cancer cells. Those skilled in the art will recognize that such biological sample may additionally comprise other biological components, such as histologically normal appearing cells (e.g., adjacent the tumor), depending upon the method used to obtain the tumor tissue, such as surgical resection, biopsy, or bodily fluids.

As used herein "non-tumor prostate tissue" refers to histologically normal-appearing prostate tissue which may be adjacent a prostate tumor.

As used herein, the term "sample" as used in the context of a sample obtained from a patient or a subject refers to a biological sample which contains or is suspected of containing cancer cells. The sample may be a biological fluid sample, such as, blood, spinal fluid, mammary gland fluid, semen, and the like or a solid tissue sample, such as, a biopsy sample.

Prognostic factors are those variables related to the natural history of cancer, which influence the recurrence rates and outcome of patients once they have developed cancer. Clinical parameters that have been associated with a worse prognosis include, for example, increased tumor stage, PSA level at presentation, and Gleason grade or pattern. Prognostic factors are frequently used to categorize patients into subgroups with different baseline relapse risks.

The term "prognosis" is used herein to refer to the likelihood that a cancer patient will have a cancer-attributable death or progression, including recurrence, metastatic spread, and drug resistance, of a neoplastic disease, such as prostate cancer. For example, a "good prognosis" would include long term survival without recurrence and a "bad prognosis" would include cancer recurrence.

As used herein, the term "expression level" or "level of expression" as applied to a gene refers to the normalized level of a gene product, e.g., the normalized value determined for the RNA expression level of a gene or for the polypeptide expression level of a gene.

The term "gene product" or "expression product" are used herein to refer to the RNA (ribonucleic acid) transcription products (transcripts) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc.

The term "RNA transcript" as used herein refers to the RNA transcription products of a gene, including, for example, mRNA, an unspliced RNA, a splice variant mRNA, a microRNA, and a fragmented RNA.

The term "microRNA" and "miRNA" are used herein to refer to a small, non-coding, single-stranded RNA of about 18-25 nucleotides that may regulate gene expression.

The term "long intergenic non-coding RNA" or "long non-coding RNA" (long ncRNA, lncRNA) are non-protein coding transcripts longer than about 200 nucleotides.

Unless indicated otherwise, each gene name used herein corresponds to the Official Symbol assigned to the gene and provided by Entrez Gene as of the filing date of this application.

The terms "correlated" and "associated" are used interchangeably herein to refer to the association between two measurements (or measured entities). The disclosure provides genes, gene subsets, microRNAs, long non-coding RNA, or combinations thereof, the expression levels of which are associated with tumor diagnosis and/or prognosis and/or treatment.

The terms "good prognosis" or "positive prognosis" as used herein refer to a beneficial clinical outcome, such as long-term survival without recurrence. The terms "bad prognosis" or "negative prognosis" as used herein refer to a negative clinical outcome, such as cancer recurrence.

The term "risk classification" means a grouping of subjects by the level of risk (or likelihood) that the subject will experience a particular clinical outcome. A subject may be classified into a risk group or classified at a level of risk based on the methods of the present disclosure, e.g. high, medium, or low risk. A "risk group" is a group of subjects or individuals with a similar level of risk for a particular clinical outcome.

The term "long-term" survival is used herein to refer to survival for a particular time period, e.g., for at least 5 years, or for at least 10 years.

The term "recurrence" is used herein to refer to local or distant recurrence (i.e., metastasis) of cancer. For example, prostate cancer can recur locally in the tissue next to the prostate or in the seminal vesicles. The cancer may also affect the surrounding lymph nodes in the pelvis or lymph nodes outside this area. Prostate cancer can also spread to tissues next to the prostate, such as pelvic muscles, bones, or other organs. Recurrence can be determined by clinical recurrence detected by, for example, imaging study or biopsy, or biochemical recurrence.

The term "polynucleotide" generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In general, the term "polynucleotide" encompasses all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA-DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "Ct" as used herein refers to threshold cycle, the cycle number in quantitative polymerase chain reaction (qPCR) at which the fluorescence generated within a reaction well exceeds the defined threshold, i.e. the point during the reaction at which a sufficient number of amplicons have accumulated to meet the defined threshold.

The term "Cp" as used herein refers to "crossing point". The Cp value is calculated by determining the second derivatives of entire qPCR amplification curves and their maximum value. The Cp value represents the cycle at which the increase of fluorescence is highest and where the logarithmic phase of a PCR begins.

As used herein, the term "amplicon" refers to pieces of DNA that have been synthesized using amplification techniques, such as polymerase chain reactions (PCR) and ligase chain reactions.

The terms "splicing" and "RNA splicing" are used interchangeably and refer to RNA processing that removes introns and joins exons to produce mature mRNA with continuous coding sequence that moves into the cytoplasm of an eukaryotic cell.

A "computer-based system" refers to a system of hardware, software, and data storage medium used to analyze information. The minimum hardware of a patient computer-based system comprises a central processing unit (CPU), and hardware for data input, data output (e.g., display), and data storage. An ordinarily skilled artisan can readily appreciate that any currently available computer-based systems and/or components thereof are suitable for use in connection with the methods of the present disclosure. The data storage medium may comprise any manufacture comprising a recording of the present information as described above, or a memory access device that can access such a manufacture.

A "processor" or "computing means" references any hardware and/or software combination that will perform the functions required of it. For example, a suitable processor may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

As used herein, the terms "active surveillance" and "watchful waiting" are used interchangeably and mean closely monitoring a patient's condition without giving any treatment until symptoms appear or change. For example, in prostate cancer, watchful waiting is usually used in older men with other medical problems and early-stage disease.

As used herein, the term "surgery" applies to surgical methods undertaken for removal of cancerous tissue, including pelvic lymphadenectomy, radical prostatectomy, transurethral resection of the prostate (TURP), excision, dissection, and tumor biopsy/removal. The tumor tissue or sections used for gene expression analysis may have been obtained from any of these methods.

As used herein, the term "therapy" includes radiation, hormonal therapy, cryosurgery, chemotherapy, biologic therapy, and high-intensity focused ultrasound.

The term "kidney cancer" as used herein refers to cancer of the kidney. This includes, but not limited to, renal cell carcinoma (RCC), Transitional Cell Carcinoma, Wilms' Tumor and Renal Sarcoma.

The term "about," particularly in reference to a given quantity, is meant to encompass deviations of plus or minus five percent.

As used herein, the term "genetic profile" in the context of a patient or tissue from a patient refers to expression level of one or more oncogenes, DNA methylation status of one or more tumor suppressor genes, expression level of one or more miRNA, and expression level of one or more lncRNA in a tissue sample. For example, genetic profile may be determined for a cancer tissue from a patient and from a reference tissue, such as, normal tissue, e.g., the cancer and normal tissue may be prostate tissue.

As used herein, the term "oncogene" refers to a gene that has the potential to cause cancer. In certain tumor cells, oncogenes are expressed at high levels.

As used herein, the phrase "tumor suppressor gene" refers to a gene that protects a cell from turning into a tumor cell. In certain tumor cells, one or more tumor suppressor genes are reduced in expression or mutated causing a loss or reduction in its function.

DETAILED DESCRIPTION

Before the present assay devices and method are described, it is to be understood that this invention is not limited to particular embodiments of the methods and devices described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a sequence" includes a plurality of such sequences and reference to "the detectable signal" includes reference to one or more detectable signals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Method of Multivariate Molecule Analysis

Hundreds of genes are altered in various cancers. Provided herein are methods for identifying a set of genes that can be used to provide diagnosis, prognosis, and/or treatment options for a type of cancer. The set of genes used in the methods of the present disclosure are classified into tumor suppressor genes, oncogenes, miRNA and lncRNA.

As explained further below, the methods of the present disclosure include determining a genetic profile for a cancer tissue or cell. In certain embodiments, the genetic profile includes measurement of expression level of at least one oncogene, DNA methylation status of at least one tumor suppressor gene, expression level of at least one miRNA and at least one lncRNA.

The assay method and device are applicable to various cancers such as lung, breast, colorectal, prostate, liver, bladder; kidney, cervix, pancreatic, gastric, brain, oral, endometrium, and ovary to identify a set of genes that are differentially expressed in these cancers. For example, the assay may detect expression of a set of 2-40 oncogenes, DNA methylation profile of a set of 2-40 genes; expression of a set of 2-40 microRNAs; and expression of a set of 2-40 lncRNA a tissue sample. The genetic profile generated by the assay may be used for early diagnosis, prognosis, and treatment decisions of various cancers.

The present disclosure includes (a) assaying expression of an oncogene, (b) assaying DNA methylation of a tumor suppressor gene, (c) assaying expression of a miRNA; (d) assaying expression of a long non-coding RNA, and (e) combining the analysis of steps (a), (b), (c), and (d) in order to make a diagnosis of the patient and a prognosis of the patient with respect to a particular type of cancer.

In each of the steps (a), (b), (c), and (d) multiple different assay tests may be used and multiple different markers may be assayed. The results obtained may be analyzed and the diagnosis carried out based on prior analysis of a statistically significant number of assays on a statistically significant number of patients with a particular type of cancer. The diagnosis and evaluation of the prognosis of prostate cancer patients is provided here by example. However, the general concept of the invention is applicable to other types of cancer using different markers associated with those cancers as known to those skilled in the art upon reading this disclosure.

The assay of the invention provides information on whether a patient has early stage or late stage cancer based on the expression of genetic biomarkers (mRNA expression, DNA methylation, miRNA expression, lncRNA) in the samples. In certain cases, a probability score may be calculated based on the assaying step (a), (b), (c) and (d). If the score is low, the cancer is in early stage. If the score is high, the cancer is in an advanced stage.

The assay of the invention provides information on whether patient needs surgery or chemo/radiation therapy/watchful waiting based on the number of genes and amount of genetic biomarkers expressed in the tumor samples. In certain cases, a probability score may be calculated based on the assaying step (a), (b), (c) and (d). If the score is high, the cancer is aggressive and the patient may need surgery. If the score is low, the patient has early stage cancer and may need chemo/radiation/watchful waiting.

The assay of the invention provides information on determining if the treatment (surgery/chemo/radiation therapy) is effective based on probability score may be calculated based on the assaying steps (a), (b), (c) and (d) performed on a tissue sample from a subject receiving the treatment. If the assay shows a low score or a score lower than that assessed prior to the treatment, the treatment is working. If the score is high or has increased compared to the score assesses prior to the treatment, then the treatment is not effective and may need to be adjusted.

The assay of the invention provides information on the prognosis of cancer based on the score obtained from assaying steps (a), (b), (c) and (d). If the score is high, the cancer is aggressive and the prognosis is poor. This situation may require aggressive treatment. If the score is low, the cancer is slow growing and standard treatment can be applied.

In certain embodiments, the genetic profile of tumor tissue from a patient may be compared to a reference genetic profile. In certain embodiments, the reference genetic profile may be generated by performing the assays (a)-(d) on a non-cancerous tissue from the patient or from a set of non-cancerous tissue from a group of healthy subjects. In certain embodiments, the reference genetic profile when generated using tissue from healthy subjects may be generated from the matching tissue and from subjects that are age and gender matched to the patient. For example, the genetic profile of a prostate cancer sample may be compared to the genetic profile of a normal prostate tissue from the patient or normal prostate tissue from a reference, which may be a set of healthy individuals.

The increase or decrease in expression levels or DNA methylation may be in comparison to a reference as explained herein.

In certain embodiments, the generation and analysis of genetic profile may include:

(a) assaying expression of one or more oncogene selected the group consisting of: AMACR; SOX4; PSA; TMPRSS2; TWIST1; EZH2; PAP; PSCA; Akt; ERG; Ak2; c-myc; VEGF; MMP9; EGFR; CCND1; CCNE1; CCNA1; CA-199-9; EIF3; SIRT1; YAP1; AFP; Cox2; MTA1, MMP2, MMP7; CXCR3; PDGF; KLF5; KLF8; MMP1; CXCR7; NSE; hMLH1; PSMA; mTOR; PI3K; EZH2; and Survivin;

(b) assaying DNA methylation of at least one tumor suppressor gene selected from the group consisting of RASSF1; TIG1; RARb; MDR1; ID4; GSTPI; SPON2; TIMP3; PTGS2; TIGI; BNIP3; AOX1; Clorf114; GAS6; HAPLN3; KLF8; BNC1, FZD1; RPL39L; SYN2; LMX1B1; CXXC5; APC; P16; HIC1; ANPEP; ABCA1; TET1; SFRP2, IGFBP7; KLK6; KLK10; EVX1; HIF3A; HAAO; HOXD3; TBX15; RASSF10; H4K20; H3K27; PITX21 CYP24A1; HINI; NKK2.5; CDH13; DPYS; PTGS2; EFEMP1; RGS2; SLC5A8; ZNF132; TSHZ3; AKAp12; EN1; SOCS3; WIF1; CRMP4; NKX3.1; CXCL14; and PTEN;

(c) assaying expression of at least one non-coding micro RNA (miRNA) selected from the group consisting of miR-205; miR-31; miR-23b; miR-203; miR-101; miR-708; miR-34b; miR-182, miR-151, miR-21, miR-888, miR-183, miR-106b-25, miR-31, miR-221, miR-222, miR-125b, miR-20a, miR-106b, miR-32, miR-16, miR-1, miR-204, miR-27b, hsa-let-7a, miR-101, miR-7, miR-155, miR-185, miR-200b, and miR-29b; and (d) assaying expression of one or more long non-coding RNA (lncRNA) selected from the group consisting of GAS5, DD3, H19, HOTAIR, MALAT-1, HULA, PCGEM1, PRNCR1, PCAT1, PCAT18, PlncRNA-1, CTBP1-AS, PCA3; XIST; HOTTIP; ANRIL; AIRN; ICR1, PWR1, LINOCR, EVF2, NRON, ZEB2(NAT), Antisense UCHL1, BACE1AS, LINCMD1, HULC, IPS1, CDR1-AS, KCS1-AS, MEG3, MIAT, NDM29, RMRP, SRA-1, TERC, UCA1, Zfas1, CUDR, BIC, aHIF, and AK023948.

In certain embodiments, the subject may be suspected of having prostate cancer and the method may include assaying (a) expression level of oncogenes AMACR, SOX4, TMPRSS2, TWIST1, EZH2, PSA, PAP; (b) DNA methylation of RASSF1, TIG1, RARB, MDR1, ID4; (c) expression level of miR-205, miR-31, miR-23b, miR-101, miR-203; and optionally (d) expression level of lncRNAs ZFAS1 and MALAT1. In certain embodiments, differential in comparison to a standard in at least one of (a)-(d), for example two, three or all of (a)-(d) provides a diagnosis of prostate cancer.

In certain embodiments, significantly increased expression of at least one or more of the AMACR, SOX4; methylation of at least one of RAFSF1, TIG1 and RARB and significantly decreased expression of one or more of miR-205, miR-31, miR-23b indicates that the patient has prostate cancer.

In certain cases, the subject may be suspected of having kidney cancer, and the method (a) comprises assaying the level of expression of oncogenes CCND1 and EGFR; (b) comprises assaying the level of DNA methylation of tumor suppressor genes TIG1 and BNC1; (c) comprises assaying the level of expression of oncogenic miRNAs miR-21 and miR210 and tumor suppressor miRNAs, miR-23b and miR-34b; and (d) comprises assaying the level of expression of lncRNA ZFAS1. Wherein the subject is diagnosed as having kidney cancer when the level of at least two of (a), (b), (c), and (d) is different as compared to a reference. The reference is normal kidney cells obtained from the subject. For example, when level of at least one gene in: (a) is increased, (b) is methylated, (c) is increased and (d) is decreased, the subject is diagnosed as having kidney cancer.

In certain cases, the subject is suspected of having colon cancer and (a) comprises assaying the level of expression of oncogenes TWIST1, CCND1, MET and SOX4; (b) comprises assaying the level of DNA methylation of tumor suppressor genes OSMA, SFRP1, MGMT, TIMP3, BNC1 and RARB; (c) comprises assaying the level of expression of oncogenic miRNAs miR-182, miR-183, miR-21 and miR210; and (d) comprises assaying the level of expression of lncRNA H19. Wherein the subject is diagnosed as having colon cancer when the level of at least two of (a), (b), (c), and (d) is different as compared to a reference. The reference is normal colon cells obtained from the subject. For example, when level of at least one gene in: (a) is increased, (b) is methylated, (c) is increased and (d) is decreased, the subject is diagnosed as having colon cancer.

In certain cases, the subject is suspected of having lung cancer and (a) comprises assaying the level of expression of oncogenes TWIST1 and MET; (b) comprises assaying the level of DNA methylation of tumor suppressor genes BNC1, MGMT, RASSF1, and SFRP1; (c) comprises assaying the level of expression of oncogenic miRNAs miR-210, miR-182, and miR-21; and (d) comprises assaying the level of expression of lncRNA MALAT1, wherein the subject is diagnosed as having lung cancer if a the level of at least two of (a), (b), (c), and (d) is different as compared to a reference. The reference is normal lung cells obtained from the subject. For example, when level of at least one gene in: (a) is increased, (b) is methylated, (c) is increased and (d) is decreased, the subject is diagnosed as having lung cancer.

In certain cases, a method of diagnosing a subject suspected of having prostate cancer may include: assaying expression of miR-96 in prostate tissue sample of the subject to determine a miR-96 expression level; using the miR-96 expression level to diagnose the subject, wherein an increased miR-96 expression level in the prostate tissue sample compared to a miR-96 reference level is indicative of prostate cancer. The miR-96 reference level may be miR-96 expression level in non-cancerous prostate tissue from the subject suspected of having cancer.

Treatment Decision

Genetic profile that includes oncogene expression level, tumor suppressor gene DNA methylation status, and expression levels of miRNA and lncRNA can be used to determine treatment options for a patient.

The treatment decision takes into account not only the increased expression of an oncogene but also whether tumor suppressor gene DNA methylation status, and expression levels of miRNA and lncRNA are changed in order to determine the severity of a cancer and treatment options for the same.

In certain embodiments, although an oncogene may be upregulated in a sample from a cancer patient, surgery to remove the cancerous tissue may be recommended only when the expression levels of miRNA and lncRNA and DNA methylation of tumor suppressor genes is also taken into account. For example, in addition to an oncogene, a tumor suppressor gene may be methylated by more than 50%, at least one miRNA and at least one lncRNA may be differentially expressed in order to determine that the treatment option may be surgery to remove the tumor.

In certain embodiments, the genetic profile that may be used to determine treatment option may be specific to a particular cancer. For example, in prostate cancer patients the genetic profile may include assay of:

(a) expression of at least one oncogene selected from the group consisting of: AMACR, SOX4, TMPRSS2, TWIST1, PSA and PAP;

(b) one tumor suppressor gene DNA methylation profile, where the tumor suppressor genes are RASSF1, TIG1, RARb, MDR1, and ID4;

(c) expression of at least one miRNAs selected from the group consisting of miR-205, miR-31, miR-23b, miR-101 and miR-185; and (d) expression of at least one of lncRNAs ZFAS1 and MALAT1.

In certain embodiments, all of the genes listed in (a)-(d) may be assayed.

In certain embodiments, the cancer may be kidney cancer, for example renal cell carcinoma and the genetic profile may include assay of:

(a) expression of at least one oncogene CCND1 and EGFR;

(b) one tumor suppressor gene DNA methylation profile, where the tumor suppressor genes are TIG1 and BNC1;

(c) expression of at least one miRNAs selected from the group consisting of miR-21 and miR210; and (d) expression of the lncRNA ZFAS1.

In certain embodiments, all of the genes listed in (a)-(d) may be assayed.

In certain embodiments, a method of determining treatment of a subject having prostate cancer is provided. The method may include (i) assaying a sample from a prostate cancer patient for: (a) expression of oncogenes AMACR, SOX4, TMPRSS2, TWIST1, PSA and PAP; (b) DNA methylation of tumor suppressor genes RASSF1, TIG1, RARb, MDR1, and ID4; (c) expression of miRNAs miR-205, miR-31, miR-23b, miR-101 and miR-185; and (d) expression of lncRNAs ZFAS1 and MALAT1; (ii) comparing the expression and methylation status to a normal reference. Based on the results of the assaying it may be determined that the patient requires surgery, is recommended surgery, or watchful waiting.

For example, it may be determined that the patient requires surgery to remove prostate tissue when expression of at least one of the oncogenes AMACR, SOX4, TMPRSS2, TWIST1, PSA and PAP is increased by about 5 fold and others is increased by about 2 fold; DNA methylation of at least one of tumor suppressor genes RASSF1, TIG1, RARb, MDR1, and ID4 is increased by about 50%; expression of at least one of miRNAs miR-205, miR-31, miR-23b, miR-101 and miR-185 is reduced by about 2 folds; and expression of at least one of long non-coding RNAs ZFAS1 and MALAT1 is unchanged or increased by about 2 folds.

In certain cases, it may be determined that the patient is recommended to obtain surgery to remove prostate tissue when expression of the oncogenes AMACR, SOX4, TMPRSS2, TWIST1, PSA and PAP is unchanged; DNA methylation of at least one of tumor suppressor genes RASSF1, TIG1, RARb, MDR1, and ID4 is increased by about 50%; expression of at least one of miRNAs miR-205, miR-31, miR-23b, miR-101 and miR-185 is reduced by about 2 folds; and expression of at least one of long non-coding RNAs ZFAS1 and MALAT1 is increased by about 2 folds; or expression of at least one of the oncogenes AMACR, SOX4, TMPRSS2, TWIST1, PSA and PAP is increased by about 5 fold and others is increased by about 2 fold; DNA methylation of tumor suppressor genes RASSF1, TIG1, RARb, MDR1, and ID4 is unchanged; expression of at least one of miRNAs miR-205, miR-31, miR-23b, miR-101 and miR-185 is reduced by about 2 folds; and expression of at least one of long non-coding RNAs ZFAS1 and MALAT1 is unchanged or increased by about 2 folds.

In certain cases, it may be determined that the patient does not require surgery to remove prostate tissue and should be monitored for prostate cancer when expression of the oncogenes AMACR, SOX4, TMPRSS2, TWIST1, PSA and PAP is unchanged; DNA methylation of tumor suppressor genes RASSF1, TIG1, RARb, MDR1, and ID4 is unchanged; expression of at least one of miRNAs miR-205, miR-31, miR-23b, miR-101 and miR-185 is reduced by about 2 folds; and expression of at least one of long non-coding RNAs ZFAS1 and MALAT1 is increased by about 2 folds.

In some embodiments, the cancer may be kidney cancer and the assays described herein may be used to determine treatment options for a patient having kidney cancer, such as, renal cell carcinoma. In certain cases, the cancer may be kidney cancer and the assay may include:

(a) assaying expression of one or more oncogene selected the group consisting of: CCND1; EGFR; ADAM17; Akt; FOXO3A; PI3K; MTDH; ZEB1; FAK; AKT; EphA2; STAT3; mTOR; c-Met; MMP9; VEGF; Vimentin; EZH2; c-Myc; HIF1a; TGM2; b-catenin; MEK1; CTNNB1; ZEB2; Survivin; MCAM; BMI1; FN1; TAGLN2; Src; ROCK-1; KCNMA1; LOX; SEMA6A; SIX2; PAX2; Cox-2; ANGPT2; NEDD9; C-Fos; c-Jun; NOTCH1; SFRP-2; HER2; and MET (b) assaying DNA methylation of at least one tumor suppressor gene selected from the group consisting of TIG1, BNC1; VHL; FOXO1; LPRC2; PTPN13; SFRP1; ERBB4; TCF21; SLC12A1; KLK1, KLK6; KLK7; FBN2; BNC1; ATP1B1; sFRP2; DKK3; WIF1; SLC16A3; KLK4; TNS3; CADM2; UNC5D; LRP1B; EN2; MAPK; PAX3; BAG2; FBLN1; WNT7A; SLC34A2; OVOUL1; TMPRSS2; SST; BMP4; SFRP1; HIC1; LRRC3B; GATA5; Rap1GAP; APAF-1; SPARC; DAPK-1; PCDH17; UNC5C; KILLIN; KLHL35; ZSCAN18; PCDH8; FBN2; CCDC8; ATP5G2; CORO6; SCUBE3; KRT19; RASSF1A; GATA3; TIMP-3; RPRM; CST6; SFRP1; GREM1; COL14A1; COL15A1; GREM1; p16; ECAD; TIMP3; MGMT; BTG3; TU3A; TFAP2A; MT1G; 14-3-3 sigma; UCHL1; FHIT; CXCL16; KRT19; CXCL16; APAF-1; DAPK-1; SFRP-1; CDH1; PTGS2; XAF1; DLC1; APAF-1; HOX13; CA9; gamma-catenin; connexin 32; SLIT2; MT1G; GSTPI; MT1G; and E-cadherin.

(c) assaying expression of at least one non-coding micro RNA (miRNA) selected from the group consisting of miR-21, miR-210, miR-23b, miR-34b, miR-141; miR-203; miR-204-5p; miR-205; miR-708; miR-584; miR-200b; miR-145; miR-143; miR-187; miR-185; miR-217; miR-200c; miR-215; miR-192; miR-194; miR-379; miR-656; miR-218; miR-30d; miR-27a; miR-193a.5p; miR-199a-3p; miR-184; miR-514; miR-135a; miR-99a; miR-10b; miR-19a; miR-29a; miR-127; miR-130; miR-138; miR-139-5p; miR-101; miR-126; miR-195; miR-451; miR-1285; miR-206; miR-1; miR-135a; miR-429; miR-1291; miR133b; miR-1826; miR-34a; let-7a; miR-199a; miR-355; miR-218; miR-30c; miR- 26a; miR-29a; miR-30a; miR-146a; miR-9; miR-141; miR-185; miR-200b; miR-363; miR429; and miR-514 and (d) assaying expression of one or more long non-coding RNA (lncRNA) selected from the group consisting of ZFAS1; GAS5, DD3, H19, HOTAIR, MALAT-1, HULA, PCGEM1, PRNCR1, PCAT1, PCAT18, PlncRNA-1, CTBP1-AS, PCA3; XIST; HOTTIP; ANRIL; AIRN; ICR1, PWR1, LINOCR, EVF2, NRON, ZEB2(NAT), Antisense UCHL1, BACE1AS, LINCMD1, HULC, IPS1, CDR1-AS, KCS1-AS, MEG3, MIAT, NDM29, RMRP, SRA-1, TERC, UCA1, CUDR, BIC, aHIF, and AK023948.

In certain embodiments, a method for determining treatment of a subject having kidney cancer is provided. The method may include (i) assaying a tumor sample from kidney tissue of the subject for: (a) expression of oncogenes CCND1 and EGFR; (b) DNA methylation of tumor suppressor genes TIG1 and BNC1; (c) expression of oncogenic miRNAs (miR-21 and miR210) and tumor suppressor miRNAs (miR-23b and miR-34b); and (d) expression of lncRNA ZFAS1; (ii) comparing the expression and methylation status to a normal reference. Based on the results of the assaying it may be determined that the patient requires surgery, is recommended surgery, or watchful waiting.

In certain embodiments, the treatment for the patient may be surgery to remove kidney tissue. A treatment option that includes removal of kidney tissue may be decided when expression of at least one of the oncogenes CCND1 and EGFR is increased by about 2 fold and the other is unchanged; DNA methylation of at least one of tumor suppressor genes TIG1 and BNC1 is increased by about 50%; expression of at least one of oncogenic miRNAs miR-21 and miR210 is increased by about 2 folds or one of the tumor suppressor miRNAs (miR-23b and miR-34b) is decreased by 2-fold; and expression of lncRNA ZFAS1 is unchanged or increased by about 2 folds.

In certain embodiments, the treatment option may include recommendation to remove kidney tissue when expression of the oncogenes CCND1 and EGFR is unchanged; DNA methylation of at least one of tumor suppressor genes TIG1 and BNC1 is increased by about 50%; expression of at least one of oncogenic miRNAs miR-21 and miR210 is increased by about 2 folds or one of the tumor suppressor miRNAs (miR-23b and miR-34b) is decreased by 2-fold; and expression of lncRNA ZFAS1 is increased by about 2 folds.

Expression of at least one of the oncogenes CCND1 and EGFR increased by about 2 fold; DNA methylation of tumor suppressor genes TIG1 and BNC1 is unchanged; expression of at least one of oncogenic miRNAs miR-21 and miR210 is increased by about 2 folds or one of the tumor suppressor miRNAs (miR-23b and miR-34b) is decreased by 2-fold; and expression of lncRNA ZFAS1 is increased by about 2 folds.

In certain embodiments, based on the assaying steps it may be determined that the patient does not require immediate treatment by instead should be monitored when expression of the oncogenes CCND1 and EGFR is unchanged; DNA methylation of tumor suppressor genes TIG1 and BNC1 is unchanged; expression of at least one of oncogenic miRNAs miR-21 and miR210 is increased by about 2 folds or one of the tumor suppressor miRNAs (miR-23b and miR-34b) is decreased by 2-fold; and expression of lncRNA ZFAS1 is increased by about 2 folds.

The methods for determining treatment options provide treatments that include surgery as well as no treatment but watchful waiting. The use of the assaying steps to determine mode of treatment may provide treatments such as surgery only to patients who need it and avoid overtreatment such as surgery in patients who do not need the treatment.

Any biological sample from a subject diagnosed as having or suspected of having cancer may be assayed in the methods disclosed herein. A biological sample as used herein refers to a body fluid sample or a tissue sample. In certain embodiments, a body fluid sample, such as, whole blood sample, or a fraction thereof may be assayed in the subject methods. In certain embodiments, the body fluid sample, such as, whole blood sample, or a fraction thereof may be subject to an amplification protocol to increase the amount/copy number of a target gene(s) or expression product(s) thereof prior to the assaying step of the subject methods.

In certain embodiments, circulating tumor cells (CTCs) may be assayed in the subject methods. CTCs are cells that circulate in the bloodstream after shedding from primary and metastatic tumors. CTCs can be detected in patients with a variety of cancers including head and neck, breast, lung, colorectal, gastric, prostate, bladder, renal, pancreatic, and liver cancer. CTCs in blood samples can serve as a real-time liquid biopsy for frequent, non-invasive clinical analyses that can provide information on prognosis, therapy selection, drug response and resistance.

Two classes of approaches have been developed to isolate CTCs. The first class are affinity-based enrichment targeting cancer cell-specific surface markers and the second class comprise affinity-independent enrichment based on physical properties of CTCs such as size, density and migration profiles that distinguish them from normal host cells (Barradas and Terstappen, "Toward the biological understanding of CTC: capture technologies, definitions and potential to create metastasis," Cancers (2013) 5: 1619-42). The most widely used platform is the CellSearch® circulating tumor cell test (Veridex, Raritan, N.J.) which employs antibody-coated magnetic beads to capture CTCs expressing epithelial cell surface markers such as EpCAM and cytokeratins.

Methods of Assaying Expression Levels of mRNA, miRNA, lncRNA

The methods and compositions of the present disclosure will employ, unless otherwise indicated, conventional techniques of molecular biology which are within the skill of the art.

Methods of oncogene expression profiling may include methods for measuring expression level of the mRNA or protein encoded by the oncogene of interest. Expression level of mRNA, miRNA, and lncRNA may be determined by conventional methods, such as, those based on hybridization analysis of polynucleotides, sequencing of polynucleotides, amplification based methods, and the like. Exemplary methods known in the art for the quantification of RNA expression in a sample include northern blotting, in situ hybridization, RNAse protection assays and PCR-based methods, such as reverse transcription PCT (RT-PCR). Antibodies may be employed that can recognize sequence-specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Reverse Transcriptase PCR (RT-PCR

Typically, total RNA that includes mRNA, microRNA, lncRNA is isolated from a test sample, e.g., from a primary tumor. Optionally, normal tissues from the same patient can be used as an internal control. Such normal tissue can be histologically-appearing normal tissue adjacent a tumor. Total RNA can be extracted from a tissue sample, e.g., from a sample that is fresh, frozen (e.g. fresh frozen), paraffin-embedded, or fixed (e.g. formalin-fixed).

General methods for mRNA, microRNA and lncRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995). In particular, RNA isolation can be performed using a purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

The sample containing the RNA is then subjected to reverse transcription to produce cDNA from the RNA template, followed by exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

PCR-based methods use a thermostable DNA-dependent DNA polymerase, such as a Taq DNA polymerase. For example, TaqMan. PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction product. A third oligonucleotide, or probe, can be designed to facilitate detection of a nucleotide sequence of the amplicon located between the hybridization sites the two PCR primers. The probe can be detectably labeled, e.g., with a reporter dye, and can further be provided with both a fluorescent dye, and a quencher fluorescent dye, as in a Taqman probe configuration. Where a Taqman is used, during the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan RT-PCR can be performed using commercially available equipment, such as, for example, high-throughput platforms such as the ABI PRISM 7700 Sequence Detection System. (Perkin-Elmer-Applied Biosystems, Foster City, Calif., USA), or Lightcycler (Roche Molecular Biochemicals, Mannheim, Germany) In some embodiments, the procedure may be run on a LightCycler 480 (Roche Diagnostics) real-time PCR system, which is a microwell plate-based cycler platform.

Another type of detection chemistries used for quantitative PCR involves the use an intercalating dye that incorporates into double-stranded DNA. Of these fluorescent dyes, SYBR® Green I dye is commonly used. This detection method is suitable when a single amplicon is being studied, as the dye will intercalate into any double-stranded DNA generated.

5'-Nuclease assay data are commonly initially expressed as a threshold cycle ("Ct"). Fluorescence values are recorded during every cycle and represent the amount of product amplified to that point in the amplification reaction. The threshold cycle (Ct) is generally described as the point when the fluorescent signal is first recorded as statistically significant. Alternatively, data may be expressed as a crossing point ("Cp"). The Cp value is calculated by determining the second derivatives of entire qPCR amplification curves and their maximum value. The Cp value represents the cycle at which the increase of fluorescence is highest and where the logarithmic phase of a PCR begins.

To minimize errors and the effect of sample-to-sample variation, RT-PCR is usually performed using an internal standard. The ideal internal standard gene (also referred to as a reference gene) is expressed at a quite constant level among cancerous and non-cancerous tissue of the same origin (i.e., a level that is not significantly different among normal and cancerous tissues), and is not significantly affected by the experimental treatment (i.e., does not exhibit a significant difference in expression level in the relevant tissue as a result of exposure to chemotherapy), and expressed at a quite constant level among the same tissue taken from different patients. For example, reference genes useful in the methods disclosed herein should not exhibit significantly different expression levels in cancerous prostate as compared to normal prostate tissue. RNAs frequently used to normalize patterns of gene expression are mRNAs for the housekeeping genes glyceraldehyde-3-phosphate-dehydrogenase (GAPDH) and β-actin. Exemplary reference genes used for normalization comprise one or more of the following genes: AAMP, ARF1, ATP5E, CLTC, GPS1, and PGK1. Gene expression measurements can be normalized relative to the mean of one or more (e.g., 2, 3, 4, 5, or more) reference genes. Reference-normalized expression measurements can range from 2 to 15, where a one unit increase generally reflects a 2-fold increase in RNA quantity.

Real time PCR is compatible both with quantitative competitive PCR, where internal competitor for each target sequence is used for normalization, and with quantitative comparative PCR using a normalization gene contained within the sample, or a housekeeping gene for RT-PCR.

The steps of a representative protocol for use in the methods of the present disclosure use fixed, paraffin-embedded tissues as the RNA source. For example, mRNA isolation, purification, primer extension and amplification can be performed according to methods available in the art. Briefly, a representative process may start with cutting about 10 µm thick sections of paraffin-embedded tumor tissue samples. The RNA is then extracted, and protein and DNA depleted from the RNA-containing sample. After analysis of the RNA concentration, RNA is reverse transcribed using gene specific primers followed by RT-PCR to provide for cDNA amplification products.

Design of Intron-Based PCR Primers and Probes

PCR primers and probes can be designed based upon exon or intron sequences present in the mRNA transcript of the gene of interest. Primer/probe design can be performed using publicly available software, such as the DNA BLAT software.

Where necessary or desired, repetitive sequences of the target sequence can be masked to mitigate non-specific signals. Exemplary tools to accomplish this include the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); and the like.

Other factors that can influence PCR primer design include primer length, melting temperature (Tm), and G/C content, specificity, complementary primer sequences, and 3'-end sequence. PCR primers may be about 17-30 bases in length, and may contain about 20-80%, such as, for example, about 50%-60% G+C bases, and exhibit Tm's between 50° C. and 80° C., e.g. about 50° C. to 70° C.

Other PCR-Based Methods

Further PCR-based techniques that can find use in the methods disclosed herein include, for example, BeadArray technology (Illumina, San Diego, Calif.; BeadsArray for Detection of Gene Expression (BADGE), using the commercially available Luminex100 LabMAP system and multiple color-coded microspheres (Luminex Corp., Austin, Tex.) in a rapid assay for gene expression and high coverage expression profiling (HiCEP) analysis.

Microarrays

Expression levels of a sequence of interest can also be assessed using the microarray technique. In this method, polynucleotide sequences of interest (including cDNAs and oligonucleotides) are arrayed on a substrate. The arrayed sequences are then contacted under conditions suitable for specific hybridization with detectably labeled cDNA generated from RNA of a test sample. As in the RT-PCR method, the source of RNA typically is total RNA isolated from a tumor sample, and optionally from normal tissue of the same patient as an internal control or cell lines. RNA can be extracted, for example, from fresh, frozen, archived, paraffin-embedded, fixed (e.g. formalin-fixed), paraffin-embedded and fixed tissue samples.

For example, PCR amplified inserts of cDNA clones of a gene to be assayed are applied to a substrate in a dense array. Usually at least 10,000 nucleotide sequences are applied to the substrate. For example, the microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After washing under stringent conditions to remove non-specifically bound probes, the chip is scanned by confocal laser microscopy or by another detection method, such as a CCD camera. Quantitation of hybridization of each arrayed element allows for assessment of corresponding RNA abundance.

With dual color fluorescence, separately labeled cDNA probes generated from two sources of RNA are hybridized pair wise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels. Microarray analysis can be performed by commercially available equipment, following manufacturer's protocols, such as by using the Affymetrix GenChip Technology, or Incyte's microarray technology.

Normalization of Expression Levels

The expression data used in the methods disclosed herein can be normalized. Normalization refers to a process to correct for (normalize away), for example, differences in the amount of RNA assayed and variability in the quality of the RNA used, to remove unwanted sources of systematic variation in Ct or Cp measurements, and the like. With respect to RT-PCR experiments involving archived fixed paraffin embedded tissue samples, sources of systematic variation are known to include the degree of RNA degradation relative to the age of the patient sample and the type of fixative used to store the sample. Other sources of systematic variation are attributable to laboratory processing conditions.

Assays can provide for normalization by incorporating the expression of certain normalizing genes, which do not significantly differ in expression levels under the relevant conditions. Exemplary normalization genes disclosed herein include housekeeping genes. Normalization can be based on the mean or median signal (Ct or Cp) of all of the assayed genes or a large subset thereof (global normalization approach). In general, the normalizing genes, also referred to as reference genes should be genes that are known not to exhibit significantly different expression in prostate cancer as compared to non-cancerous prostate tissue, and are not significantly affected by various sample and process conditions, thus provide for normalizing away extraneous effects.

In exemplary embodiments, one or more of the following genes may be used as references by which the mRNA or microRNA or lncRNA expression data is normalized: AAMP, ARF1, ATP5E, CLTC, GPS1, and PGK1. In another exemplary embodiment, one or more of the following microRNAs are used as references by which the expression data of microRNAs are normalized: hsa-miR-106a; hsa-miR-146b-5p; hsa-miR-191; hsa-miR-19b; and hsa-miR-92a. Those skilled in the art will recognize that normalization may be achieved in numerous ways, and the techniques described above are intended only to be exemplary, not exhaustive.

DNA Methylation Analysis

The analysis of promoter methylation of individual genes may be carried out using two bisulfite PCR based methods: methylation specific PCR (MSP) and the bisulfite genomic sequencing PCR (BSP). DNA may be modified by sodium bisulfite followed by PCR amplification. MSP may be used as a qualitative method for detecting CpG methylation, BSP may be used for detailed methylation mapping and quantification.

Primer design for successful mapping of promoter methylation is described herein. Promoter sequences of the 5' flanking sequences of relevant genes are retrieved from GenBank. A program, MethPrimer, developed by for BSP and MSP may be used to design primers for BSP and MSP. DNA may be extracted from cultured cells or human tissues using DNAzol (Invitrogen) per manufacture's instruction. The DNA may be denatured with freshly prepared NaOH and neutralized by adding ammonium acetate and processed for methylation specific PCR (MSP). MSP is a sensitive method for methylation mapping, but can only detect the methylation status of a few CpG sites in one reaction. MSP needs two sets of primers, one primer set recognizes and amplifies methylated DNA, while the other primer set recognizes and amplifies unmethylated DNA. Unlike MSP, BSP uses a pair of primers to amplify modified DNA and the resulting PCR products are sequenced. This method provides a quantitative analysis of the extent of methylation of all CpG sites in the amplified region. The resulting PCR products may be purified using a purification kit such as, QIAquick PCR Purification Kit (Qiagen, Valencia, Calif.) and directly sequenced on a sequencer, e.g., an ABI automated sequencer with Dye terminators (Perkin-Elmer, Foster City, Calif.) using both sense and antisense primers used for PCR amplification.

Selection of genes (RNAs) DNA methylation; and microRNAs

Statistical Analysis and Algorithm Development

Comparison of mRNA profiles, DNA methylation profile, lncRNA profile and microRNA profile (genetic profile) among patients with and without cancer may be used for diagnosis, prognosis and treatment decisions.

Primary analysis may be carried out using a multivariable logistic regression of case/control status with a primary predictor of genetic profiles. The data may be adjusted for age, date of surgery/procedure and considers models with and without adjustment for other baseline diagnostic clinical features of various cancers (lung, breast, colorectal, prostate, liver, bladder; kidney, cervix, and ovarian). Prognostic groups are compared to the controls separately and consider combined analyses. A set of genetic profiles is compared among patients with and without cancer. Fisher's exact test and the Mann-Whitney U test is considered as alternatives to the chi-square and t-tests, respectively, as needed based on sample size/distribution.

Each individual's clinical course may be followed via their medical charts, queries to regional cancer registries and the National Death Index to identify outcomes of recurrence/progression/cancer death. Metastases or cause of death may be documented by scans, death certificates, or notes from the medical charts. Kaplan-Meier survival curves may be examined to determine progression based on genetic profile. Cox proportional hazard regression models are used to examine multivariate associations between genetic profile and time to progression, independent of age, time, and with and without adjustment for other baseline prognostic clinical features of cancer.

Patient Outcome and Survival Using Kaplan Meier Analyses

Genetic profile may be correlated to cancer survival as determined using Kaplan-Meier survival curves. The statistical analysis of the genetic profile may be used along with the patient outcomes indicated from retrospective analysis of patient histories to predict treatment options that may allow physicians and patients to make significantly improved determination of treatment options.

Reports

The methods of this invention, when practiced for commercial diagnostic purposes, generally produce a report or summary of information obtained from the herein-described methods. For example, a report may include information concerning expression levels of one or more genes, microRNAs and/or lncRNA, and DAN methylation of tumor suppressor genes, classification of the tumor or the patient's risk of recurrence, the patient's likely prognosis or risk classification, clinical and pathologic factors, treatment options, and/or other information. The methods and reports of this invention can further include storing the report in a database. The method can create a record in a database for the subject and populate the record with data. The report may be a paper report, an auditory report, or an electronic record. The report may be displayed and/or stored on a computing device (e.g., handheld device, desktop computer, smart device, website, etc.). It is contemplated that the report is provided to a physician and/or the patient. The receiving of the report can further include establishing a network connection to a server computer that includes the data and report and requesting the data and report from the server computer.

Computer Program

The values from the assays described above, such as expression data, can be calculated and stored manually. Alternatively, the above-described steps can be completely or partially performed by a computer program product. The present invention thus provides a computer program product including a computer readable storage medium having a computer program stored on it. The program can, when read by a computer, execute relevant calculations based on values obtained from analysis of one or more biological sample from an individual (e.g., gene expression levels, normalization, standardization, thresholding, and conversion of values from assays to a score and/or text or graphical depiction of tumor stage and related information). The computer program product has stored therein a computer program for performing the calculation.

The present disclosure provides systems for executing the program described above, which system generally includes: a) a central computing environment; b) an input device, operatively connected to the computing environment, to receive patient data, wherein the patient data can include, for example, expression level or other value obtained from an assay using a biological sample from the patient, or microarray data, as described in detail above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates an expression score, thresholding, or other functions described herein. The methods provided by the present invention may also be automated in whole or in part.

Device for Multivariate Molecule Analysis

Devices that may be used carry out the methods disclosed herein are provided. In certain embodiments, the device may be include multiple compartments for (a) assaying expression of an oncogene; (b) assaying DNA methylation of a tumor suppressor gene; (c) assaying expression of a non-coding micro RNA (miRNA); and (d) assaying expression of a long non-coding RNA (lncRNA). For example, the reagents for performing the assaying steps (a)-(d) may be spatially separated into different compartments.

In certain embodiments, the device may also include an optical analyzer that can analyze the assaying steps (a)-(d) and determine the amount of analyte present in a test sample. The device may also compare the amount of analyte to that in a control sample. The control sample may be analyzed in parallel with a test sample or the results from assaying steps (a)-(d) in a control sample may be stored in the device and used to determine whether the analyte is differentially expressed or methylated in comparison to the control sample. In alternate embodiments, the device may store the analyte levels known to occur in control samples.

As noted elsewhere herein the control sample may be a normal tissue sample obtained from the patient whose cancer tissue sample is being analyzed or it may be normal tissue sample or samples from subject who are known to not have cancer. The control tissue may originate from the same organ and in some embodiments same region of the organ as the cancer tissue.

In certain embodiments, each of the compartments may be thermally regulated. For example, each of the compartments may be independently thermally regulated so that each compartment can have a different temperature, if needed. In certain embodiments, a single temperature control device may be present and the temperature of the plurality of compartments may be regulated en masse. In other embodiments, two or more of the compartments may have a temperature control device that sets the temperature in the compartments.

In certain cases, the compartments may include containers such as cartridges, tubes, mini-tubes, capillaries and the like which may be preloaded with reagents for performing one or more of the assays (a)-(d). The containers may be of any suitable material such as silicon, glass, plastic, and the like. In certain embodiments, the container may be disposable one-time use container.

In certain embodiments, the device may be semiautomated or automated. For example, the device may include a loading area in which the sample, e.g., a nucleic acid sample from a test tissue is disposed, the device may include fluidics that may transport the sample into the different compartments for carrying out assays (a)-(d). In other embodiments, the test sample may be loaded individually into the different compartments.

In certain embodiments, the containers may be removed automatically or manually after completion of the assaying. In other embodiments, the containers may be reused after the contents are washed out and replaced with a set of reagents for the next assay.

In certain embodiments, the device may be a microfluidic device as described in U.S. Pat. Nos. 8,053,214; 8,592,157; 6,391,541, which are hereby incorporated by reference in their entirety.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

Prostate Cancer Tissue. Paraffin-embedded prostate tissue from 40 prostate cancer patients collected at the San Francisco Veterans Affairs Medical Center (SFVAMC) was analyzed. A minimum 5 year post-surgical follow-up was available for each of the patients. Cancer samples were characterized in terms of stages and grades. Normal and cancerous regions were identified in hematoxylin and eosin stained paraffin-embedded prostate tissue and were isolated by laser capture microdissection.

Kidney Cancer Tissue. Paraffin-embedded kidney tissue from 40 renal cell carcinoma patients collected at the San Francisco Veterans Affairs Medical Center (SFVAMC) was analyzed. A minimum 5 year post-surgical follow-up was available for each of the patients. Cancer samples were characterized in terms of stages and grades. Normal and cancerous regions in identified in hematoxylin and eosin stained paraffin-embedded kidney tissue and were isolated by laser capture microdissection.

Lung Cancer Tissue. Paraffin-embedded lung tissue from 25 lung cancer patients collected at the San Francisco Veterans Affairs Medical Center (SFVAMC) was analyzed. A minimum 5 year post-surgical follow-up was available for each of the patients. Cancer samples were characterized in terms of stages and grades. Normal and cancerous regions were identified in hematoxylin and eosin stained paraffin-embedded lung tissue and were isolated by laser capture microdissection.

Colon Cancer Tissue. Paraffin-embedded colon tissue from 25 colon cancer patients collected at the San Francisco Veterans Affairs Medical Center (SFVAMC) was analyzed. A minimum 5 year post-surgical follow-up was available for each of the patients. Cancer samples were characterized in terms of stages and grades. Normal and cancerous regions in identified in hematoxylin and eosin stained paraffin-embedded colon tissue and were isolated by laser capture microdissection.

Liver Cancer Tissue. Paraffin-embedded liver tissue from 25 lung cancer patients collected at the San Francisco Veterans Affairs Medical Center (SFVAMC) was analyzed. A minimum 5 year post-surgical follow-up was available for each of the patients. Cancer samples were characterized in terms of stages and grades. Normal and cancerous regions in identified in hematoxylin and eosin stained paraffin-embedded liver tissue and were isolated by laser capture microdissection.

Laser Capture Microdissection. All the samples were processed through automated laser capture microdissection system using an AutoPix machine. For this purpose, paraffin block section (10-12 micron) were placed on slides and stained with Hematoxylin, to make the nuclei visible. Information regarding the type of the Capture, slide name, and notes were entered. The system automatically acquires and displays a roadmap for each slide. An area on the roadmap was displayed on a live video display. Following manufacturer's instructions, selected area of the tissue was dissected using laser beam.

Quantitative measurement of oncogenes. RNA was isolated from micro-dissected paraffin sections of prostate cancer and adjacent normal tissue with miRNeasy Mini Kit (Qiagen) following the protocols of manufacturers. 10 ng of RNA was reversed transcribed in 10 µl solution containing 1XRT Buffer, 4 mM dNTPs, 0.2 µl RNase inhibitors, 0.5 µl Multiscribe Reverse Transcriptase (Applied Biosystems) and 0.4 µl Hexanucleotide Mix (Roche). The solution was incubated at 25° C. for 10 min, 37° C. for 60 min, 85° C. for 4 min, and 15° C. for 10 min. 2 µl of the reverse transcription product was amplified by real-time PCR in 20 µl solution containing 10 µl QuantiTech SYBR Green PCR Master Mix (Qiagen), and 0.5 µM forward (F) and reverse (R) primers (Table 1). Real-time PCR was performed in 7500 Fast Real-time PCR Systems (Allied Biosystems). The data of Ct (thresh-hold cycle) in target gene $Ct_{target}$ and control gene GAPDH $Ct_{control}$ in both cancer and normal were collected. The fold of target gene in cancer prostate tissue versus normal prostate tissue from each patient was calculated by $2^{-ddCt}$, while $$ddCt = (Ct_{target} - Ct_{control})_{cancer} - (Ct_{target} - Ct_{control})_{normal}.$$

Methylation analysis. DNA was isolated from micro-dissected paraffin sections of prostate cancer and adjacent normal tissues with QIAquick PCR purification kit (Qiagen) following the protocols of manufacturers. DNA was modified with $NaHSO_3$ using EZ DNA Methylation-Gold Kit (ZYMO Research) according to the procedures recommended by manufacturers. 1 ng of modified DNA was amplified by PCR in 10 µl solution containing 1XPCR buffer, 0.2 mM dNTPs, 0.4 µM forward and reverse primers (MU1 and MU2 respectively in Table 2), and HotStar DNA polymerase (Qiagen). The solution was incubated at 95° C. for 5 min, followed by 15 cycles of 94° C. for 30 sec, 60° C. for 30 sec and 72° C. for 30 sec. The PCR products were amplified by the second PCR in 20 µl solution containing 10 µl QuantiTech SYBR Green PCR Master Mix (Qiagen), 1 µM forward and reverse primers for methylation reaction (M1 and M2, Table 2), or 1 µl forward and reverse primers for unmethylation reaction (U1 and U2, Table 2). Real-time PCR was performed in 7500 Fast Real-time PCR Systems (Applied Biosystems). Data of Ct(thresh-hold Cycle) in methylation reaction $Ct_m$ and unmethylation reaction $Ct_u$ in both cancer and normal were collected. The higher percent of methylation in cancer prostate tissue versus normal prostate tissue from each patient was calculated by $-5Xd$-$dCt$, while $$ddCT = (Ct_m - Ct_u)_{cancer} - (Ct_m - Ct_u)_{normal}.$$

Measurement of microRNA expression. MicroRNA was isolated from micro-dissected prostate cancer and adjacent normal tissues. 10 ng of microRNA was reverse transcribed using reverse transcription primers and TaqMan MicroRNA Reverse Transcription Kit (Applied Biosystems), and then amplified by real-time PCR using real-time PCR primers, probes and TaqMan Fast Universal PCR Master Mix (Applied Biosystems) according to the protocols recommended by manufacturers. Real-time PCR was performed in 7500 Fast Real-time PCR Systems (Allied Biosystems). The data of Ct (thresh hold cycle) in target microRNA $Ct_{target}$ and control RNU48 $Ct_{control}$ in both cancer and normal were collected. The fold of microRNA expression in cancer prostate tissue versus normal prostate tissue from each patient was calculated by $2^{-ddCt}$, while $$ddCt = (Ct_{target} - Ct_{control})_{cancer} - (Ct_{target} - Ct_{control})_{normal}.$$

Measurement of long non-coding RNA expression. RNA was isolated from micro-dissected prostate cancer and adjacent normal tissues. 10 ng of RNA was reverse transcribed in 10 µl solution containing 1XRT Buffer, 4 mM dNTPs, 0.2 µl RNase inhibitors, 0.5 µl Multiscribe Reverse Transcriptase (Applied Biosystems) and 0.4 µl Hexanucleotide Mix (Roche). The solution was incubated at 25° C. for 10 min, 37° C. for 60 min, 85° C. for 4 min, and 15° C. for 10 min. 2 µl of the reverse transcription product was amplified by real-time PCR using real-time PCR primers, probes and TaqMan Fast Universal PCR Master Mix (Applied Biosystems) following the procedure recommended by manufacturers. Real-time PCR was performed in 7500 Fast Real-time PCR Systems (Allied Biosystems). The data of Ct (thresh-hold cycle) in target gene $Ct_{target}$ and control gene GAPDH $Ct_{control}$ in both cancer and normal were collected. The fold change of target gene in cancer prostate tissue versus normal prostate tissue from each patient was calculated by $2^{-ddCt}$, while $$ddCt = (Ct_{target} - Ct_{control})_{cancer} - (Ct_{target} - Ct_{control})_{normal}.$$

Prostate cancer tissue was obtained from 40 patients. The tissue sample was formalin fixed paraffin embedded. Expression of oncogenes AMACR; SOX4; PSA; TMPRSS2; TWIST1; EZH2; PAP was assayed by q RT-PCR. DNA methylation of RASSF1; TIG1; RARb; MDR1; ID4 was assayed by q-PCR assay. Expression of miR-205; miR-31; miR-23b; miR-203 was assayed by q-PCR. Expression of long noncoding RNAs MALAT-1 and ZFAS1 was assayed by q-PCR. The expression level was compared to the expression level in normal prostate tissue micro-dissected from prostate tissue obtained from the same prostate cancer patient.

The following primers were used to assay the biomarkers for prostate cancer:

TABLE 1

Oncogene Expression

| Gene | | Primers | Product Size |
|---|---|---|---|
| AMACR | F: | AGCTGGCCACGATATCAACT (SEQ ID NO: 1) | 71 bp |
| | R: | GATTCTCACCACTTCTGCCA (SEQ ID NO: 2) | |
| SOX4 | F: | GACATGCACAACGCCGAGAT (SEQ ID NO: 3) | 70 bp |
| | R: | TCTTGTCGCTGTCTTTGAGC (SEQ ID NO: 4) | |
| TMPRSS2 | F: | CCATCCGGGACAGTGTGCA (SEQ ID NO: 5) | 55 bp |
| | R: | TCAAGGTGATGCACAGTGCT (SEQ ID NO: 6) | |
| TWIST1 | F: | CCCACCCCCTCAGCAGGG (SEQ ID NO: 7) | 54 bp |
| | R: | CTCCTTCTCTGGAAACAATGAC (SEQ ID NO: 8) | |

TABLE 1-continued

Oncogene Expression

| Gene | Primers | Product Size |
|---|---|---|
| EZH2 | F: GTCTCCCCTACAGCAGAATT (SEQ ID NO: 9) <br> R: CTTCATCTCCCATATAAGGAATG (SEQ ID NO: 10) | 74 bp |
| PSA | F2: TCTTCCTCACCCTGTCCGT (SEQ ID NO: 11) <br> R2: CACAATCCGAGACAGGATGA (SEQ ID NO: 12) | 62 bp |
| PAP | F: CCAAGGAGTTGAAGTTTGTGAC (SEQ ID NO: 13) <br> R: GGTGTCAATGGGACTTCGGT (SEQ ID NO: 14) | 62 bp |
| GAPDH | F: TCTTCACCACCATGGAGAAG (SEQ ID NO: 15) <br> R: GCAGAGATGATGACCCTTTTG (SEQ ID NO: 16) | 67 bp |

TABLE 2

DNA Methylation

| Gene | Primers | Product Size |
|---|---|---|
| RASSF1 | MU1: GGGTATTTTYGYGTGGTGTTTTG (SEQ ID NO: 17) <br> MU2: CCRCCTTACCCTTCCTTCC (SEQ ID NO: 18) | 96 bp |
| | M1: TGGTGTTTTGCGGTCGTCGTC (SEQ ID NO: 19) <br> M2: TACCCTTCCTTCCCTCCTTCG (SEQ ID NO: 20) | 77 bp |
| | U1: TGTGTGGTGTTTTGTGGTTGTTGTT (SEQ ID NO: 21) <br> U2: TACCCTTCCTTCCCTCCTTCA (SEQ ID NO: 22) | 81 bp |
| TIG1 | MU1: GGTTTGGGTTAGAAGTATTYGGTTTTG (SEQ ID NO: 23) <br> MU2: CCCATAAAACCACTCCTTTTCC (SEQ ID NO: 24) | 122 bp |
| | M1: TGCGTTGCGGAGGCGATGTC (SEQ ID NO: 25) <br> M2: CTCCTTTTCCACGTTTCCCG (SEQ ID NO: 26) | 94 bp |
| | U1: GTTTTGTGTTGTGGAGGTGATGTT (SEQ ID NO: 27) <br> U2: CACTCCTTTTCCACATTTCCCA (SEQ ID NO: 28) | 100 bp |
| RARB | MU1: YGAGTTGTTTGAGGATTGGGATGT (SEQ ID NO: 29) <br> MU2: CCRAATACRTTCCRAATCCTACC (SEQ ID NO: 30) | 92 bp |
| | M1: GATTGGGATGTCGAGAACGC (SEQ ID NO: 31) <br> M2: TTCCGAATCCTACCCCGACG (SEQ ID NO: 32) | 70 bp |
| | U1: GAGGATTGGGATGTTGAGAATGT (SEQ ID NO: 33) <br> U2: CATTCCAAATCCTACCCCAACA (SEQ ID NO: 34) | 75 bp |
| MDR1 | MU1: GTTTYGTAGTTTTTYGAGGAATTAGTATTTAG (SEQ ID NO: 35) <br> MU2: ACRAAACRACTATACTCAACCC (SEQ ID NO: 36) | 122 bp |
| | M1: GAGGAATTAGTATTTAGTTAATTCGGGTC (SEQ ID NO: 37) <br> M2: ATACTCAACCCACGCCCCG (SEQ ID NO: 38) | 96 bp |
| | U1: TGAGGAATTAGTATTTAGTTAATTTGGGTT (SEQ ID NO: 39) <br> U2: CTATACTCAACCCACACCCCA (SEQ ID NO: 40) | 99 bp |
| ID4 | MU1: AATTGTTGGGTTYGGGAGTG (SEQ ID NO: 41) <br> MU2: CRAAAAAACAAACAAACTCCRAACCC (SEQ ID NO: 42) | 106 bp |
| | M1: TTGGGTTCGGGAGTGTCGC (SEQ ID NO: 43) <br> M2: CGTCCGCGACCGACTCCG (SEQ ID NO: 44) | 74 bp |
| | U1: TGTTGGGTTTGGGAGTGTTGT (SEQ ID NO: 45) <br> U2: CCCATCCACAACCAACTCCA (SEQ ID NO: 46) | 78 bp | miRNA Expression: Primers for the detection of miR-205, miR-31, miR-23b, miR-101 and miR-203 are commercially available from TaqMan.

Long non-coding RNA expression: Primers for the detection of MALAT-1 and ZFAS1 are commercially available from TaqMan.

The following primers were used to assay the biomarkers for kidney cancer:

TABLE 3

Oncogene expression

| | | | Product Size |
|---|---|---|---|
| CCDN1 | F: | CGGAAGATCGTCGCCACCT (SEQ ID NO: 47) | 89 bp |
| | R: | TCCAGGTAGTTCATGGCCAG (SEQ ID NO: 48) | |
| EGFR | F: | CATGTCGATGGACTTCCAGA (SEQ ID NO: 49) | 60 bp |
| | R: | GGACAGCTTGGATCACACTT (SEQ ID NO: 50) | |

TABLE 4

DNA methylation

| | | | Product Size |
|---|---|---|---|
| TIG1 | MU1: | GGTTTGGGTTAGAAGTATTYGGTTTTG (SEQ ID NO: 23) | 122 bp |
| | MU2: | CCCATAAAACCACTCCTTTTCC (SEQ ID NO: 24) | |
| | M1: | TGCGTTGCGGAGGCGATGTC (SEQ ID NO: 25) | 94 bp |
| | M2: | CTCCTTTTCCACGTTTCCCG (SEQ ID NO: 26) | |
| | U1: | GTTTTGTGTTGTGGAGGTGATGTT (SEQ ID NO: 27) | 100 bp |
| | U2: | CACTCCTTTTCCACATTTCCCA (SEQ ID NO: 28) | |
| BNC1 | MU1: | AGTTYGGYGGGGGTAGATAT (SEQ ID NO: 51) | 98 bp |
| | MU2: | ACRCCCTAAATCAACRCAACTAAAAC (SEQ ID NO: 52) | |
| | M1: | GTCGTCGGCGAGGTTTTCGC (SEQ ID NO: 53) | 46 bp |
| | M2: | AAACGAAACCGTAACCCCCG (SEQ ID NO: 54) | |
| | U1: | TGTTGGTTGTTGGTGAGGTTTTTGT (SEQ ID NO: 55) | 57 bp |
| | U2: | CAACTAAAACAAAACCATAACCCCCA (SEQ ID NO: 56) | |

MicroRNA expression: Primers for the detection of miR-210, miR-21, miR-23b and miR-34b are commercially available from TaqMan.

Long non-coding RNA expression: Primers for the detection of ZFAS1 is commercially available from TaqMan.

Example 1

Eighteen biomarkers were assayed in prostate cancer tissue (see Materials and Methods).

18 biomarkers were tested in prostate cancer: high expression of oncogenes such as AMACR (27/32, 84%); SOX4 (20/32, 62%), TMPRSS2 (11/32, 34%), TWIST1 (21/32, 65%), PSA (12/32, 37%), PAP (8/32, 25%); high DNA methylation of RASSF1 (29/32, 90%), TIG1 (25/32, 78%), RARB (29/32, 90%), MDR1 (16/32, 50%), ID4 (11/32, 34%); low expression of non-coding microRNAs such as miR-205 (30/32, 93%), miR-31 (29/32, 90%), miR-23b (26/32, 81%), miR-101 (25/32, 78%), miR-185 (22/32, 68%), high expression of long non-coding RNA such as ZFAS1 (17/32, 53%), MALAT-1 (18/32, 56%). Therefore, the combination of these genes has the potential for diagnosis of prostate cancer.

Gleason "score" or "grade" was given to prostate cancer based upon its microscopic appearance. Tumors with a low Gleason score typically grow slowly enough that they may not pose a significant threat to the patients in their lifetimes. These patients are monitored ("watchful waiting" or "active surveillance") over time. Cancers with a higher Gleason score are more aggressive and have a worse prognosis, and these patients are generally treated with surgery (e.g., radical prostectomy) and, in some cases, therapy (e.g., radiation, hormone, ultrasound, chemotherapy). Gleason scores (or sums) comprise grades of the two most common tumor patterns. These patterns are referred to as Gleason patterns 1-5, with pattern 1 being the most well-differentiated. Most have a mixture of patterns. To obtain a Gleason score or grade, the dominant pattern is added to the second most prevalent pattern to obtain a number between 2 and 10. The Gleason Grades include: G1: well differentiated (slight anaplasia) (Gleason 2-4); G2: moderately differentiated (moderate anaplasia) (Gleason 5-6); G3-4: poorly differentiated/undifferentiated (marked anaplasia) (Gleason 7-10).

The stage was based on the prostate biopsy results (including the Gleason score), the PSA level, and any other exams or tests that were done to find out how far the cancer has spread. A staging system is a standard way for the cancer care team to describe how far a cancer has spread. The most widely used staging system for prostate cancer is the American Joint Committee on Cancer (AJCC) TNM system. The TNM system for prostate cancer is based on 5 key pieces of information: The extent of the primary tumor (T category); Whether the cancer has spread to nearby lymph nodes (N category); The absence or presence of distant metastasis (M category), The PSA level at the time of diagnosis, The Gleason score, based on the prostate biopsy (or surgery). There are actually 2 types of staging for prostate cancer: The clinical stage is the doctor's best estimate of the extent of the disease, based on the results of the physical exam (including DRE), lab tests, prostate biopsy, and any imaging tests the patient has had. If the patient had surgery, your doctors can also determine the pathologic stage, which is based on the surgery and examination of the removed tissue. This means that if the patient has surgery, the stage of the cancer might actually change afterward (if cancer was found in a place it wasn't suspected, for example). Currently, pathologic staging is considered to be more accurate than clinical staging, as it allows the doctor to get a firsthand impression of the extent of the disease. Thus, currently surgery (radical prostatectomy) is considered to be advantageous over radiation therapy or active surveillance.

There are 4 categories for describing the local extent of a prostate tumor, ranging from T1 to T4. Most of these have subcategories as well. T1: The tumor is not palpable or not visible with imaging such as transrectal ultrasound. T1a: Cancer is found incidentally (by accident) during a transurethral resection of the prostate (TURP) that was done for benign prostatic hyperplasia (BPH). Cancer is in no more than 5% of the tissue removed. T1b: Cancer is found during a TURP but is in more than 5% of the tissue removed. T1c: Cancer is found by needle biopsy that was done because of an increased PSA. T2: The tumor is palpable with a digital rectal exam (DRE) or visible with imaging such as transrectal ultrasound, but it still appears to be confined to the prostate gland. T2a: The cancer is in one half or less of only one side (left or right) of your prostate. T2b: The cancer is in more than half of only one side (left or right) of your prostate. T2c: The cancer is in both sides of your prostate. T3: The cancer has begun to grow and spread outside your prostate and may have spread into the seminal vesicles. T3a: The cancer extends outside the prostate but not to the seminal vesicles. T3b: The cancer has spread to the seminal vesicles. T4: The cancer has grown into tissues next to your prostate (other than the seminal vesicles), such as the urethral sphincter (muscle that helps control urination), the rectum, the bladder, and/or the wall of the pelvis.

N categories N categories describe whether the cancer has spread to nearby (regional) lymph nodes. NX: Nearby lymph nodes were not assessed. N0: The cancer has not spread to any nearby lymph nodes. N1: The cancer has spread to one or more nearby lymph nodes in the pelvis.

M categories M categories describe whether the cancer has spread to distant parts of the body. The most common sites of prostate cancer spread are to the bones and to distant lymph nodes, although it can also spread to other organs, such as the lungs and liver. M0: The cancer has not spread past nearby lymph nodes. M1: The cancer has spread beyond the nearby lymph nodes. M1a: The cancer has spread to distant (outside of the pelvis) lymph nodes. M1b: The cancer has spread to the bones. M1c: The cancer has spread to other organs such as lungs, liver, or brain (with or without spread to the bones).

T1, N0, M0, Gleason score 6 or less, PSA less than 10: The doctor can't feel the tumor or see it with an imaging test such as transrectal ultrasound (it was either found during a transurethral resection or was diagnosed by needle biopsy done for a high PSA) [T1]. The cancer is still within the prostate and has not spread to nearby lymph nodes [N0] or elsewhere in the body [M0]. The Gleason score is 6 or less and the PSA level is less than 10.

T2a, N0, M0, Gleason score 6 or less, PSA less than 10: The tumor can be felt by digital rectal exam or seen with imaging such as transrectal ultrasound and is in one half or less of only one side (left or right) of your prostate [T2a]. The cancer is still within the prostate and has not spread to nearby lymph nodes [N0] or elsewhere in the body [M0]. The Gleason score is 6 or less and the PSA level is less than 10.

Stage IIA: One of the following applies:

T1, N0, M0, Gleason score of 7, PSA less than 20: The doctor can't feel the tumor or see it with imaging such as transrectal ultrasound (it was either found during a transurethral resection or was diagnosed by needle biopsy done for a high PSA level) [T1]. The cancer has not spread to nearby lymph nodes [N0] or elsewhere in the body [M0]. The tumor has a Gleason score of 7. The PSA level is less than 20.

T1, N0, M0, Gleason score of 6 or less, PSA at least 10 but less than 20: The doctor can't feel the tumor or see it with imaging such as transrectal ultrasound (it was either found during a transurethral resection or was diagnosed by needle biopsy done for a high PSA) [T1]. The cancer has not spread to nearby lymph nodes [N0] or elsewhere in the body [M0]. The tumor has a Gleason score of 6 or less. The PSA level is at least 10 but less than 20.

T2a or T2b, N0, M0, Gleason score of 7 or less, PSA less than 20: The tumor can be felt by digital rectal exam or seen with imaging such as transrectal ultrasound and is in only one side of the prostate [T2a or T2b]. The cancer has not spread to nearby lymph nodes [N0] or elsewhere in the body [M0]. It has a Gleason score of 7 or less. The PSA level is less than 20.

Stage IIB: One of the following applies:

T2c, N0, M0, any Gleason score, any PSA: The tumor can be felt by digital rectal exam or seen with imaging such as transrectal ultrasound and is in both sides of the prostate [T2c]. The cancer has not spread to nearby lymph nodes [N0] or elsewhere in the body [M0]. The tumor can have any Gleason score and the PSA can be any value.

T1 or T2, N0, M0, any Gleason score, PSA of 20 or more: The cancer has not yet begun to spread outside the prostate. It may (or may not) be felt by digital rectal exam or seen with imaging such as transrectal ultrasound [T1 or T2]. The cancer has not spread to nearby lymph nodes [N0] or elsewhere in the body [M0]. The tumor can have any Gleason score. The PSA level is at least 20.

T1 or T2, N0, M0, Gleason score of 8 or higher, any PSA: The cancer has not yet begun to spread outside the prostate. It may (or may not) be felt by digital rectal exam or seen with imaging such as transrectal ultrasound [T1 or T2]. The cancer has not spread to nearby lymph nodes [N0] or elsewhere in the body [M0]. The Gleason score is 8 or higher. The PSA can be any value.

Stage III: T3, N0, M0, any Gleason score, any PSA: The cancer has begun to spread outside the prostate and may have spread to the seminal vesicles [T3], but it has not spread to nearby lymph nodes [N0] or elsewhere in the body [M0]. The tumor can have any Gleason score and the PSA can be any value.

Stage IV: One of the following applies:

T4, N0, M0, any Gleason score, any PSA: The cancer has spread to tissues next to the prostate (other than the seminal vesicles), such as the urethral sphincter (muscle that helps control urination), rectum, bladder, and/or the wall of the pelvis [T4]. The cancer has not spread to nearby lymph nodes [N0] or elsewhere in the body [M0]. The tumor can have any Gleason score and the PSA can be any value.

Any T, N1, M0, any Gleason score, any PSA: The tumor may or may not be growing into tissues near the prostate [any T]. The cancer has spread to nearby lymph nodes (N1) but has not spread elsewhere in the body [M0]. The tumor can have any Gleason score and the PSA can be any value.

Any T, any N, M1, any Gleason score, any PSA: The cancer may or may not be growing into tissues near the prostate [any T] and may or may not have spread to nearby lymph nodes [any N]. It has spread to other, more distant sites in the body [M1]. The tumor can have any Gleason score and the PSA can be any value.

Example 2

The typical prostate cancer diagnoses such as, PSA and Gleason grade and staging scores do not adequately predict clinical outcome. The PSA gene expression only has a 37% accuracy rate for identifying cancerous tissue verses normal. Therefore to prove predictability and the probability that cancer severity and stages prognoses are improved with genetic markers, unique approaches need to be utilized.

The direct comparison of expression levels with themselves and among known normal and cancerous cells and tissues allows for algorithm development that not only improves the probability of detecting cancer, but also of its aggressiveness.

Analyses were done on over 30 genes on hundreds of samples, down selected from over 200 prostate cancer genetic markers, for DNA and RNA expression in normal and cancerous biopsy samples from the same human patient. PCR and rtPCR methods were used as described above.

Oncogene profile. Over-expression of oncogenes is involved in the malignant transformation, initiation, progression and metastasis through activation of cell cycle/inhibition of apoptosis/increase in invasion and migration of cells. We analyzed a set of six oncogenes in 32 pairs of normal and cancer samples of prostate and found that 3/6 oncogenes showed higher expression in over 60% of prostate cancer samples compared to normal.

DNA Methylation Status of Tumor Suppressor Genes. DNA hyper-methylation leads to inactivation of tumor suppressor genes. Inactivation of tumor suppressor genes will lead to increase in cell cycle, decrease in apoptosis, and increase in invasion and migration. We analyzed a set of five DNA methylation of tumor suppressor genes in 32 pairs of normal and prostate cancer samples and found that 3/5 genes showed higher DNA methylation in over 75% of prostate cancer samples compared to normal.

miRNA Profile. MicroRNAs can directly modulate oncogenes and tumor suppressor genes through binding to 3'UTR regions of various genes. We analyzed a set of five microRNAs in 32 pairs of normal and prostate cancer samples and found that 3/5 miRNAs showed lower expression in over 80% of prostate cancer samples compared to normal.

lncRNA Profile. Long-non-coding RNAs can directly or indirectly modulate oncogenes and tumor suppressor genes through histone modification or chromatin remodeling. We analyzed two long-non-coding genes ZFAS1 and MALAT-1 in 32 pairs of normal and prostate cancer samples and found that these genes are highly expressed in over 50% of prostate cancer samples compared to normal.

A set of 18 genes were identified, 12 of which have a correlation of at least 65% with cancer. Of 6 Oncogenes, 3 genes (AMACR, SOX4, and TWIST1) have a correlation of over 60%; of 5 methylation genes, 3 genes (RASSF1, RARB, and TIG1) have correlation of over 75%, of 5 non-coding miRNA (low expression), 3 miRNA (miR-205, miR-31, and miR-23b) are over 80% correlated, and of 2 long non-coding RNA, both long non-coding RNA (ZFAS1 and MALAT1) are over 50%. See FIG. 1.

Example 3

The gene expression profile of each of the patients listed in FIG. 1 was analyzed to provide a treatment best suited to the patient based on the gene expression profile in prostate cancer tissue of the patient. See FIG. 1.

Criteria for Watchful waiting. Patient with moderate activation of oncogenes (less than 2-3 folds), high activation of one oncogene (more than 5 fold); DNA methylation of all genes or at least one gene less than 40%, down regulation of at least one miRNA (less than 0.01 fold) and activation of at least one long non-coding RNA (less than 2 folds).

Given that approximately 250,000 men are diagnosed with prostate cancer per year in the US, and about 50% are eligible for "active surveillance" (AS) but only 10% choose it, we estimate that well over 100,000 men in this country receive unnecessary treatment for prostate cancer each year, a huge burden in terms of public health—avoidable urinary, erectile, and bowel dysfunction—and economic cost, with initial definitive treatment costing up to $40,000 per patient. Therefore, genetic testing will help identifying the patients with aggressive tumors vs slow growing tumors and thus help urologists make right decision for prostate cancer treatment. The majority of patients diagnosed with prostate cancer actually harbor low-risk tumors that do not require immediate treatment and can be safely managed by careful monitoring, with subsequent curative treatment if evidence of cancer progression is found, an approach termed "active surveillance" (AS) (Li et al, Cancer Epidemiol 36:122-7, 2012). Overtreatment of prostate cancer is a major problem which is compounded by the patient's desire for treatment. Genetic testing would identify patients with slow growing or aggressive prostate cancer. Adoption of widespread prostate specific antigen (PSA) screening in the last two decades has increased a man's lifetime risk of prostate cancer diagnosis from 7% to 17%, with 58% of newly diagnosed cases involving low-risk tumors (Siegel et al, C A Cancer J. Cin. 63:11-30, 2013). Men with low-risk prostate cancer have an extremely low risk of cancer mortality, and there is little evidence that treatment improves survival in this group (Albertsen et al, JAMA 293:2095-101, 2005). Accordingly, the National Comprehensive Cancer Network (NCCN) Clinical Practice Guidelines for Prostate Cancer recommends AS for men with very low risk cancer and many men with low-risk cancer, and AS is increasingly being adopted by major cancer centers (Mohler et al, J. Natl Compr Canc Netw 11:1310-2, 2013; Silberstein et al, Cancer 117:4855-60, 2011). Despite the benefit of avoiding side effects associated with radical treatment, including incontinence, impotence, and bowel problems, AS is underutilized (Sanda et al, N Eng J Med 358:1250-61, 2008). An observational study of 1,886 men diagnosed with clinically localized prostate cancer between 1999 and 2004 found that, even among men with the very lowest risk prostate cancer, only 9% chose AS (Barocas et al, J. Urol 180: 1330-4, 2008). The genetic profiling methods disclosed herein will help in accurate diagnosis of the prostate tumor and proper treatment for the same.

Criteria for Surgery. Patient with high activation of at least two oncogenes (more than 5 fold) and moderate activation of other oncogenes (2-3 folds); activation of DNA methylation of at least two genes by more than 50%; down regulation of at least two miRNA (less than 0.01 fold) and activation of at least one long non-coding RNA (more than 2 folds).

Criteria for Watchful waiting/Surgery. Patient with moderate activation of oncogenes (less than 2-3 folds), high activation of one oncogene (more than 5 fold); DNA methylation of all genes or at least one gene by less than 50%; down regulation of at least two miRNAs (less than 0.01 fold) and activation of at least one long non-coding RNA (more than 2 folds).

Criteria for Clear: Patient with no activation of oncogenes; no DNA methylation; no changes in miRNAs; no change in long-non-coding RNAs is diagnosed as not having prostate cancer.

Patient #375: Out of six oncogenes, one gene was higher. AMACR is increased by 7.1 folds. Out of five DNA methylation genes, one gene was methylated by 42%. Out of five microRNAs, three had low expression from 0.26 to 0.63 fold decrease. Out of two long non-coding RNAs, MALAT1 was increased by 3.7 folds. Treatment for patient #375: Watchful waiting.

Patient #376: Out of six oncogenes, two genes were higher. AMACR is increased by 11.7 folds; TWIST1 by 8 folds. Out of five DNA methylation genes, three genes were methylated by 28-69%. Out of five microRNAs, all had low expression from 0.04 to 0.78 fold decrease. Out of two long non-coding RNAs, no change. Treatment for patient #376: Surgery.

Patient #377: Out of six oncogenes, three genes were higher. AMACR is increased by 53.7 folds; PSA by 10.4 and PAP by 6.8 folds. Out of five DNA methylation genes, three genes were methylated by 11-92%. Out of five microRNAs, all had low expression from 0.014 to 0.47 fold decrease. Out of two long non-coding RNAs, MALAT1 was increased by 5.9 folds. Treatment for patient #377: Surgery.

Patient #378: Out of six oncogenes, one gene was highly expressed. AMACR was increased by 37.8 folds and others were low. Out of five DNA methylation genes, three genes were methylated by 28-38%. Out of five microRNAs, all had low expression from 0.009 to 0.22 fold decrease. Out of two long non-coding RNAs, no change. Treatment for patient #378: Surgery.

Patient #379: Out of six oncogenes, four genes were high. AMACR was increased by 112 folds, TMPRSS2 was increased by 8.1 folds, TWIST1 by 5.5 folds PSA by 4.5 folds. Out of five DNA methylation genes, four were methylated by 14 to 52%. Out of five microRNAs, all were low from 0.02 to 0.44 fold decrease. Out of two long non-coding RNAs, ZFAS1 was increased by 3.8 folds. Treatment for patient #379: Surgery.

Patient #380: Out of six oncogenes, two were high. AMACR was increased by 118 folds, TWIST1 was increased by 16 fold and other genes were low. Out of five DNA methylation genes, four were methylated by 10 to 50%. Out of five microRNAs, all were low from 0.01 to 0.23 fold decrease. Out of two long non-coding RNAs, ZFAS1 was increased by 4.3 folds and MALAT1 was increased by 2.5 folds. Treatment for patient #380: Surgery.

Patient #381: Out of six oncogenes, one was high. AMACR was increased by 43.2, other genes were low. Out of five DNA methylation genes, three were methylated by 25 to 63%. Out of five microRNAs, all were low from 0.042 to 0.65 fold decrease. Out of two long non-coding RNAs, no significant change. Treatment for patient #381: Watchful waiting/surgery.

Patient #382: Out of six oncogenes, one was high. AMACR was increased by 8.7, other genes were low. Out of five DNA methylation genes, three were methylated by 24 to 57%. Out of five microRNAs, there was no change. Out of two long non-coding RNAs, ZFAS1 was higher 4.4 fold increase. Treatment—Watchful waiting.

Patient #383: Out of six oncogenes, five were high. AMACR was higher by 33 folds and others four genes were increased by 5-12 folds. Out of five DNA methylation genes, three were methylated by 10 to 41%. Out of five microR-NAs, four were decreased by 0.081 to 0.0.39 folds. Out of two long non-coding RNAs, ZFAS1 was higher1.28 fold increase. Treatment—Surgery.

Patient #384: Out of six oncogenes, four were high. AMACR was higher by 23 folds and others three genes were increased by 1.3 to 4.7 folds. Out of five DNA methylation genes, all showed low methylation. Out of five microRNAs, four showed lower expression from 0.2 to 0.72 folds. Out of two long non-coding RNAs,—no change. Treatment—Surgery.

Patient #387: Out of six oncogenes, three were high. AMACR was increased by 19.2 folds, other two genes were increased by 3.1 to 5.2 folds. Out of five DNA methylation genes, three genes were methylated by 20 to 61%. Out of five microRNAs, all were decreased by 0.11 to 0.57 folds. Out of two long non-coding RNAs, both were higher by 1.2 to 1.9 folds. Treatment—Surgery.

Patient #388: Out of six oncogenes, one was high. AMACR was increased by 7.3 folds, other no change. Out of five DNA methylation genes, three gene were methylated by 24-49%. Out of five microRNAs, all were decreased by 0.006 to 0.18 folds. Out of two long non-coding RNAs, one MALAT1 was higher by 2.3 folds. Treatment—Watchful waiting.

Patient #389: Out of six oncogenes, one was high. TWIST1 was higher by 5.3 folds, other no change. Out of five DNA methylation genes, three genes were methylated by 10-28%. Out of five microRNAs, all were decreased by 0.031 to 0.64 folds. Out of two long non-coding RNAs, one ZFAS1 was higher by 9.8 folds. Treatment—Watchful waiting.

Patient #390: Out of six oncogenes, four were high. AMACR was higher by 22.7 folds, other three genes were higher by 3 to 8.7 folds. Out of five DNA methylation genes, three genes were methylated by 39-50%. Out of five micro-RNAs, all were decreased by 0.023 to 0.212 folds. Out of two long non-coding RNAs, both were higher by 2.6 to 5.7 folds. Treatment—Surgery.

Patient #391: Out of six oncogenes, one gene was high. Sox4 was higher by 3.3 folds and others were no change. Out of five DNA methylation genes, three gene were methylated by 39 to 44%. Out of five microRNAs, all were decreased by 0.003 to 0.59 folds. Out of two long non-coding RNAs, there was no change. Treatment—Watchful Waiting.

Patient #392: Out of six oncogenes, one gene was high. AMACR was higher by 9.47 folds and other genes were low. Out of five DNA methylation genes, three genes were methylated by 21 to 88%. Out of five microRNAs, all were decreased by 0.009 to 0.77 folds. Out of two long non-coding RNAs, both were higher from 1.5 to 5.9 folds. Treatment—Watchful Waiting/Surgery.

Patient #393: Out of six oncogenes, two genes were higher; AMACR was higher by 7.35 folds; TWIST1 by 5.3 folds. Out of five DNA methylation genes, four genes were methylated by 15 to 23%. Out of five microRNAs, all were decreased by 0.03 to 0.51 folds. Out of two long non-coding RNAs, one was higher by 4.7 folds. Treatment—Surgery.

Patient #394: Out of six oncogenes, one gene was higher; AMACR was higher by 8.9 folds. Out of five DNA methylation genes, four genes were methylated by 17 to 38%. Out of five microRNAs, all were decreased by 0.07 to 0.55 folds. Out of two long non-coding RNAs, one was higher by 2.0 folds. Treatment—Watchful waiting.

Patient #395: Out of six oncogenes, two genes were higher; AMACR was higher by 53 folds and TWIST1 by 60 folds. Out of five DNA methylation genes, all five genes were methylated by 11-89%. Out of five microRNAs, three were decreased by 0.04 to 0.38 folds. Out of two long non-coding RNAs, one was higher by 4.0 folds. Treatment—Surgery.

Patient #396: Out of six oncogenes, two genes were higher; AMACR was higher by 65 folds and TWIST1 by 2 folds. Out of five DNA methylation genes, two genes were methylated by 56-68%. Out of five microRNAs, all were decreased by 0.01 to 0.6 folds. Out of two long non-coding RNAs, one was higher by 6.1 folds. Treatment—Surgery.

Patient #397: Out of six oncogenes, one gene was higher; Sox4 was higher by 20 folds and other genes were low. Out of five DNA methylation genes, two genes were methylated by 39-40%. Out of five microRNAs, three genes were decreased by 0.009 to 0.4 folds. Out of two long non-coding RNAs, there was no change. Treatment—Watchful waiting.

Patient #398: Out of six oncogenes, two genes were higher; AMACR was increased by 14 folds; TWIST1 by 9.1 folds others no change. Out of five DNA methylation genes, all genes were methylated by 20%. Out of five microRNAs, four genes were decreased by 0.02 to 0.69 folds. Out of two long non-coding RNAs, there was no change. Treatment—Watchful waiting/surgery.

Patient #399: Out of six oncogenes, one gene was higher; Sox4 was increased by 3.6 folds and others no change. Out of five DNA methylation genes, all genes were methylated by less than 31%. Out of five microRNAs, four genes were decreased by 0.015 to 0.71 folds. Out of two long non-coding RNAs, there was no change. Treatment—Watchful waiting.

Patient #400: Out of six oncogenes, all showed low expression. Out of five DNA methylation genes, all genes were methylated by less than 40%. Out of five microRNAs, there was no change. Out of two long non-coding RNAs, there was no change. Treatment—Clear.

Patient #401: Out of six oncogenes, two genes had higher expression. AMACR was increased by 50 folds; TWIST1 increased by 38 folds. Out of five DNA methylation genes, four genes were methylated by 20-44%. Out of five microRNAs, all showed low expression decreased by 0.002 to 0.004 folds. Out of two long non-coding RNAs, one was higher ZFAS1 by 16 folds. Treatment—Surgery.

Patient #402: Out of six oncogenes, two genes were moderately higher by 2.6 to 3.9 folds. Out of five DNA methylation genes, four genes were methylated by 17-55%. Out of five microRNAs, all showed low expression decreased by 0.009 to 0.54 folds. Out of two long non-coding RNAs, both were moderately higher by 2.6 to 3.6 folds. Treatment—watchful waiting.

Patient #403: Out of six oncogenes, two genes were higher; TWIST1 was increased by 37 folds and PSA by 5 folds. Out of five DNA methylation genes, three genes were methylated by 21-55%. Out of five microRNAs, all showed low expression; decreased by 0.001 to 0.41 folds. Out of two long non-coding RNAs, one was moderately higher by 2.4 folds. Treatment—surgery.

Patient #404: Out of six oncogenes, one gene was highly expressed; TWIST1 was increased by 47 folds and others are low. Out of five DNA methylation genes, two genes were methylated by 27-28%. Out of five microRNAs, one gene was low. Out of two long non-coding RNAs, ZFAS1 was higher by 4.6 folds and MALAT1 by 25 folds. Treatment—watchful waiting.

Patient #405: Out of six oncogenes, one gene was highly expressed; TWIST1 was increased by 258 folds and others were low. Out of five DNA methylation genes, two genes were methylated by 25-28%. Out of five microRNAs, four miRNAs were low. Out of two long non-coding RNAs, ZFAS1 was higher by 13.2 folds and MALAT1 by 2.7 folds. Treatment—surgery.

Patient #406: Out of six oncogenes, one gene was highly expressed; TWIST1 was increased by 4.7 folds and others were low. Out of five DNA methylation genes, two genes were methylated by 12-23%. Out of five microRNAs, three miRNAs were low from 0.004 to 0.67 fold. Out of two long non-coding RNAs, ZFAS1 was higher by 43 folds and MALAT1 by 5.5 folds. Treatment—watchful waiting.

Patient #410: Out of six oncogenes, one gene was highly expressed; AMACR was increased by 18.4 folds, WTIST1 was increased by 2.8 folds and others were low. Out of five DNA methylation genes, four genes were methylated by 13-82%. Out of five microRNAs, all miRNAs were low from 0.002 to 0.52 fold. Out of two long non-coding RNAs, ZFAS1 was higher by 2.9 folds and MALAT1 by 1.6 folds. Treatment—surgery.

Patient #414: Out of six oncogenes, one gene was highly expressed; TWIST1 was increased by 40.5 folds. Out of five DNA methylation genes, three genes were methylated by 17-40%. Out of five microRNAs, three miRNAs were low from 0.004 to 0.65 fold. Out of two long non-coding RNAs, no change. Treatment—Watchful waiting/surgery.

Based on an algorithmic approach to cancer diagnosis and prognosis, the following correlation between expression profiles and DNA methylation status and prognosis, diagnosis, and treatment is proposed:

| | | | | |
|---|---|---|---|---|
| Recommend Surgery | Onco >5X<br>MeDNA >50%<br>MiRNA <2X<br>LONC >2X | Onco >5X<br>MeDNA >50%<br>MiRNA NC<br>LONC NC | Onco >5X<br>MeDNA NC<br>MiRNA <2X<br>LONC >2X | Onco NC<br>MeDNA >50%<br>MiRNA <2X<br>LONC >2X |
| Watchful waiting | Onco <5X<br>MeDNA <50%<br>MiRNA NC<br>LONC NC | Onco NC<br>MeDNA >50%<br>MiRNA <2X<br>LONC >2X | Onco NC<br>MeDNA NC<br>MiRNA <2X<br>LONC >2X | |
| Clear | Onco NC<br>MeDNA NC<br>MiRNA NC<br>LONC NC | | | |

"Onco"=Oncogene; "MeDNA"=DNA methylation; "MiRNA"=micro RNA; "LONC"=long non-coding RNA; "NC"=no change.

FIG. 1E shows 60 months survival curve of the prostate cancer patients after surgery based on the expression profile of oncogene (AMACR), DNA methylation (RASSF1), microRNA (miR-101) and long non-coding RNA (MALAT1) using Kaplan-Meier method. Patients with change in one gene or no change in AMACR/RASSF1/miR-101/MALAT1 expression showed 60 months survival after surgery. Patients with change in any two genes (AMACR/RASSF1/miR-101/MALAT1) expression showed decrease in survival rate by 5%-10%. Patients with change in expression of three or all four genes (AMACR/RASSF1/miR-101/MALAT1) showed decrease in survival rate by 20%-25%. This data shows that combination of all different profile of genes can be a better predictor for prostate cancer survival.

Example 4

The gene expression profile in kidney cancer tissue of each of the patient listed in FIG. 2 was analyzed to provide a treatment best suited to the patient based on the gene expression profile. See FIG. 2. The fold change in gene expression/methylation was based on comparison of normal and cancerous kidney tissue from the same patient.

Patient #506: Out of two oncogenes, both have no change. Out of two oncogenic miRNAs, miR-210 is increased by 76.2 fold, miR21 is higher by 6.8 fold. Out of two tumor suppressor miRNAs, miR-23b is decreased by 1.3 fold. Out of two DNA methylation genes, one gene TIG1 is methylated by 18% and another gene has no change. Long non-coding RNAs, ZFAS1 is increased by 2.4 fold.

Treatment—Watchful waiting. Kidney cancer is most often treated with surgery, targeted therapy, and/or immunotherapy. Radiation therapy and chemotherapy are occasionally used. Patients with kidney cancer that has spread (metastatic cancer, see below) often receive multiple lines of therapy, which are treatments given one after another. In some cases, especially when the cancer is small and slow-growing, the doctor may recommend that the patient be monitored closely and wait to start active treatment until there is evidence that the disease is worsening. This approach is called active surveillance, watchful waiting, or watch-and-wait.

Patient #507: Out of two oncogenes, both are higher, CCND1 is increased by 3 fold and EGFR is higher by 1.8 fold. Out of two oncogenic miRNAs, miR-210 is increased by 26.4 fold, miR21 is higher by 5.5 folds. Out of two tumor suppressor miRNAs, miR-34b is decreased by 1.3 fold. Out of two DNA methylation genes, both are negative. Long non-coding RNAs, ZFAS1 is increased by 2.7 fold. Treatment—Surgery.

Patient #509: Out of two oncogenes, CCND1 is increased by 1.5 fold and another has no change. Out of two oncogenic miRNAs, miR-210 is increased by 12.8 fold, miR21 is higher by 3.67 folds. Out of two tumor suppressor miRNAs, miR-34b is decreased by 1.0 fold. Out of two DNA methylation genes, BNC1 is methylated by 19%. Long non-coding RNAs, ZFAS1 has no change. Treatment—Watchful waiting.

Patient #510: Out of two oncogenes, EGFR is increased by 4 folds. Out of two oncogenic miRNAs, miR-210 is increased by 61 fold, miR21 is higher by 3.5 folds. Out of two tumor suppressor miRNAs, miR-23b is decreased by 1.4 fold and miR-34b by 1 fold. Out of two DNA methylation genes, both genes have no change. Long non-coding RNAs, ZFAS1 has no change. Treatment—Watchful waiting/Surgery.

Patient #511: Out of two oncogenes, EGFR is increased by 3.9 fold. Out of two oncogenic miRNAs, miR-210 is increased by 5.6 fold, miR21 is higher by 2.3 fold. Out of two tumor suppressor miRNAs, miR-34b is decreased by 2.2 fold.

Out of two DNA methylation genes, both genes have methylation by 22% (TIG1) and 43% (BNC1). Long non-coding RNAs, ZFAS1 is increased by 8.3 fold. Treatment—Watchful waiting.

Patient #512: Out of two oncogenes, CCND1 is increased by 2.1 fold. Out of two oncogenic miRNAs, miR21 is increased by 3 fold. Out of two tumor suppressor miRNAs, both have no significant change. Out of two DNA methylation genes, both genes have no changes. Long non-coding RNAs, ZFAS1 is increased by 9.1 fold. Treatment—Watchful waiting.

Patient #513: Out of two oncogenes, both have no changes. Out of two oncogenic miRNAs, miR-210 is increased by 9.1 fold, miR21 is higher by 9.1 fold. Out of two tumor suppressor miRNAs, both have no significant change. Out of two DNA methylation genes, TIG1 gene methylated by 44%. Long non-coding RNAs, ZFAS1 is increased by 35 fold. Treatment—Watchful waiting.

Patient #515: Out of two oncogenes, CCND1 is increased by 9.7 fold, EGFR is increased by 1.3 fold. Out of two oncogenic miRNAs, miR-210 is increased by 31 fold, miR21 is higher by 2.1 fold. Out of two tumor suppressor miRNAs, miR-23b is decreased by 1.1 fold. Out of two DNA methylation genes, both genes have no methylation. Long non-coding RNAs, ZFAS1 is increased by 9.1 fold. Treatment—Surgery.

Patient #516: Out of two oncogenes, CCND1 is increased by 1.4 fold. Out of two oncogenic miRNAs, miR-210 is increased by 25.1 fold, miR21 is higher by 2.9 fold. Out of two tumor suppressor miRNAs, both have no significant change. Out of two DNA methylation genes, both genes have methylation by 17% (TIG1) and 18% (BNC1). Long non-coding RNAs, ZFAS1 is increased by 1.4 fold. Treatment—Watchful waiting.

Patient #517: Out of two oncogenes, CCND1 is increased by 1.4 fold. Out of two oncogenic miRNAs, miR-210 is increased by 15.3 fold, miR21 is higher by 18.4 fold. Out of two tumor suppressor miRNAs, miR-23b is decreased by 3.4 fold and miR-23b is decreased by 2.4 fold. Out of two DNA methylation genes, both genes have no change in methylation. Long non-coding RNAs, ZFAS1 has no change. Treatment—Watchful waiting.

Patient #518: Out of two oncogenes, CCND1 is increased by 2 fold, EGFR is increased by 1.6 fold. Out of two oncogenic miRNAs, miR-210 is increased by 31.8 fold, miR21 is higher by 1.4 fold. Out of two tumor suppressor miRNAs, both have no significant change. Out of two DNA methylation genes, BNC1 is methylated by 12%. Long non-coding RNAs, ZFAS1 has no change. Treatment—Watchful waiting.

Patient #519: Out of two oncogenes, CCND1 is increased by 2.4 fold. Out of two oncogenic miRNAs, miR-210 is increased by 12.8 fold, miR21 is higher by 2.56 fold. Out of two tumor suppressor miRNAs, miR-23b is decreased by 1.1 fold.

Out of two DNA methylation genes, both have no change in methylation. Long non-coding RNAs, ZFAS1 is increased by 4.1 fold. Treatment—Watchful waiting.

Patient #599: Out of two oncogenes, CCND1 is increased by 2.8 fold and EGFR is increased by 6.8 fold. Out of two oncogenic miRNAs, miR-210 is increased by 28.1 fold, miR21 is higher by 2.65 fold. Out of two tumor suppressor miRNAs, miR-23b is decreased by 1.1 fold and miR-34b by 1.5 fold. Out of two DNA methylation genes, both have no change in methylation. Long non-coding RNAs, ZFAS1 is increased by 5 fold. Treatment—Surgery.

Patient #611: Out of two oncogenes, CCND1 is increased by 1.9 fold. Out of two oncogenic miRNAs, miR-210 is increased by 23.7 fold, miR21 is higher by 2.01 fold. Out of two tumor suppressor miRNAs, miR-23b is decreased by 1.1 fold and miR-34b by 1.2 fold. Out of two DNA methylation genes, both have no change in methylation. Long non-coding RNAs, ZFAS1 is increased by 1.2 fold. Treatment—Watchful waiting.

Patient #628: Out of two oncogenes, CCND1 is increased by 2.9 fold and EGFR is increased by 7.1 fold. Out of two oncogenic miRNAs, miR-210 is increased by 20.5 fold, miR21 is higher by 2.38 fold. Out of two tumor suppressor miRNAs, both have no significant change. Out of two DNA methylation genes, BNC1 is methylated by 31%. Long non-coding RNAs, ZFAS1 is increased by 3.4 fold. Treatment—Surgery.

Patient #634: Out of two oncogenes, CCND1 is increased by 31 fold, EGFR is increased by 10 fold. Out of two oncogenic miRNAs, miR-210 is increased by 19 fold, miR21 is higher by 3.3 fold. Out of two tumor suppressor miRNAs, miR-34b is decreased by 1.8 fold. Out of two DNA methylation genes, both have no change in methylation. Long non-coding RNAs, ZFAS1 is increased by 11 fold. Treatment—Surgery.

Patient #635: Out of two oncogenes, both have no change. Out of two oncogenic miRNAs, miR-210 is increased by 39.7 fold, miR21 is higher by 5.5 fold. Out of two tumor suppressor miRNAs, miR-23b is decreased by 1.6 fold and miR-34b by 1.9 fold. Out of two DNA methylation genes, both have no change in methylation. Long non-coding RNAs, ZFAS1 is increased by 4.5 fold. Treatment—Watchful Waiting.

Patient #636: Out of two oncogenes, both have no change. Out of two oncogenic miRNAs, miR-210 is increased by 15.7 fold, miR21 is higher by 3.1 fold. Out of two tumor suppressor miRNAs, both have no significant change. Out of two DNA methylation genes, MNC1 is methylated by 15%. Long non-coding RNAs, ZFAS1 has no change. Treatment—Watchful waiting.

Patient #595: Out of two oncogenes, both have no change. Out of two oncogenic miRNAs, miR-210 is increased by 61.4 fold, miR21 is higher by 11 fold. Out of two tumor suppressor miRNAs, miR-23b is decreased by 1.5 fold and miR-34b by 2.5 fold. Out of two DNA methylation genes, both have no change in methylation. Long non-coding RNAs, ZFAS1 is increased by 13 fold. Treatment—Watchful waiting.

Patient #596: Out of two oncogenes, CCND1 is increased by 2.4 fold. Out of two oncogenic miRNAs, miR-210 is increased by 75 fold, miR21 is higher by 20 fold. Out of two tumor suppressor miRNAs, miR-23 is decreased by 1.2 fold.

Out of two DNA methylation genes, TIG1 is methylated by 20% and BNC1 is by 25%. Long non-coding RNAs, ZFAS1 is increased by 26 fold. Treatment—Watchful Waiting.

Patient #603: Out of two oncogenes, CCND1 is increased by 1.2 fold, EGFR is increased by 3.3 fold. Out of two oncogenic miRNAs, miR-210 is increased by 8.5 fold, miR21 is higher by 3.1 fold. Out of two tumor suppressor miRNAs, both have no significant change. Out of two DNA methylation genes, BNC1 is methylated by 16%. Long non-coding RNAs, ZFAS1 is increased by 18 fold. Treatment—Watchful waiting/Surgery.

Patient #604: Out of two oncogenes, EGFR is increased by 1.2 fold. Out of two oncogenic miRNAs, miR-210 is increased by 11.2 fold, miR21 is higher by 10.3 fold. Out of two tumor suppressor miRNAs, miR-34b is decreased by 1.2 fold.

Out of two DNA methylation genes, TIG1 is methylated by 14% and BNC1 by 36%. Long non-coding RNAs, ZFAS1 is increased by 1.7 fold. Treatment—Watchful Waiting.

Patient #609: Out of two oncogenes, EGFR is increased by 5.5 fold. Out of two oncogenic miRNAs, miR-210 is increased by 115 fold, miR21 is higher by 7.3 fold. Out of two tumor suppressor miRNAs, miR-23b is decreased by 1.6 fold and miR-34b by 5.3 fold. Out of two DNA methylation genes, TIG1 is methylated by 15% and BNC1 by 34%. Long non-coding RNAs, ZFAS1 is increased by 2.1 fold. Treatment—Surgery.

Patient #617: Out of two oncogenes, both have no change. Out of two oncogenic miRNAs, miR-210 is increased by 13.9 fold, miR21 is higher by 1.3 fold. Out of two tumor suppressor miRNAs, miR-23b is decreased by 1.2 fold and miR-34b by 2.9 fold. Out of two DNA methylation genes, TIG1 is methylated by 34%. Long non-coding RNAs, ZFAS1 has no change. Treatment—Watchful waiting.

Patient #520: Out of two oncogenes, CCND1 is increased by 1.9 fold. Out of two oncogenic miRNAs, miR-210 is increased by 33 fold, miR21 is higher by 1.8 fold. Out of two tumor suppressor miRNAs, miR-23b is decreased by 1.3 fold.

Out of two DNA methylation genes, BNC1 is methylated by 14%. Long non-coding RNAs, ZFAS1 is increased by 30 fold. Treatment—Watchful waiting.

Patient #521: Out of two oncogenes, both have no change. Out of two oncogenic miRNAs, miR21 is higher by 15 fold. Out of two tumor suppressor miRNAs, both have no significant change. Out of two DNA methylation genes, both have no change in methylation. Long non-coding RNAs, ZFAS1 has no change. Treatment—Clear.

Patient #524: Out of two oncogenes, CCND1 is increased by 2.1 fold, EGFR is increased by 1.9 fold. Out of two oncogenic miRNAs, miR-210 is increased by 21.5 fold, miR21 is higher by 4.24 fold. Out of two tumor suppressor miRNAs, both have no significant change. Out of two DNA methylation genes, BNC1 is methylated by 16%. Long non-coding RNAs, ZFAS1 is increased by 3.6 fold. Treatment—Watchful waiting.

Patient #529: Out of two oncogenes, CCND1 is increased by 1.5 fold. Out of two oncogenic miRNAs, miR-210 is increased by 25.8 fold, miR21 is higher by 4.66 fold. Out of two tumor suppressor miRNAs, miR-34b is decreased by 1.1 fold.

Out of two DNA methylation genes, both have no change in methylation. Long non-coding RNAs, ZFAS1 is increased by 2.9 fold. Treatment—Watchful waiting.

Patient #563: Out of two oncogenes, both have no changes. Out of two oncogenic miRNAs, miR-210 is increased by 27.4 fold, miR21 is higher by 6.8 fold. Out of two tumor suppressor miRNAs, miR-23b is decreased by 1.1 fold.

Out of two DNA methylation genes, TIG1 is methylated by 17%. Long non-coding RNAs, ZFAS1 has no change. Treatment—Watchful waiting.

Patient #624: Out of two oncogenes, CCND1 is increased by 4.9 fold, EGFR is increased by 1.3 fold. Out of two oncogenic miRNAs, miR-210 is increased by 8.8 fold. Out of two tumor suppressor miRNAs, both have no significant change. Out of two DNA methylation genes, BNC1 is methylated by 15%. Long non-coding RNA, ZFAS1 is increased by 2.8 fold. Treatment—Watchful waiting.

Summary Kidney Prognosis:

| | | | | |
|---|---|---|---|---|
| Recommend Surgery | Onco >2X<br>MeDNA >50%<br>MiRNA >2X<br>LONC >2X | Onco >2X<br>MeDNA >50%<br>MiRNA NC<br>LONC NC | Onco >2X<br>MeDNA NC<br>MiRNA <2X<br>LONC >2X | Onco NC<br>MeDNA >50%<br>MiRNA <2X<br>LONC >2X |
| Watchful waiting | Onco <2X<br>MeDNA <50%<br>MiRNA NC<br>LONC NC | Onco NC<br>MeDNA >50%<br>MiRNA >2X<br>LONC <2X | Onco NC<br>MeDNA NC<br>MiRNA >2X<br>LONC >2X | |
| Clear | Onco NC<br>MeDNA NC<br>MiRNA NC<br>LONC NC | | | |

"Onco"=Oncogene; "MeDNA"=DNA methylation; "MiRNA"=micro RNA; "LONC"=long non-coding RNA; "NC"=no change.

Figure 2F:
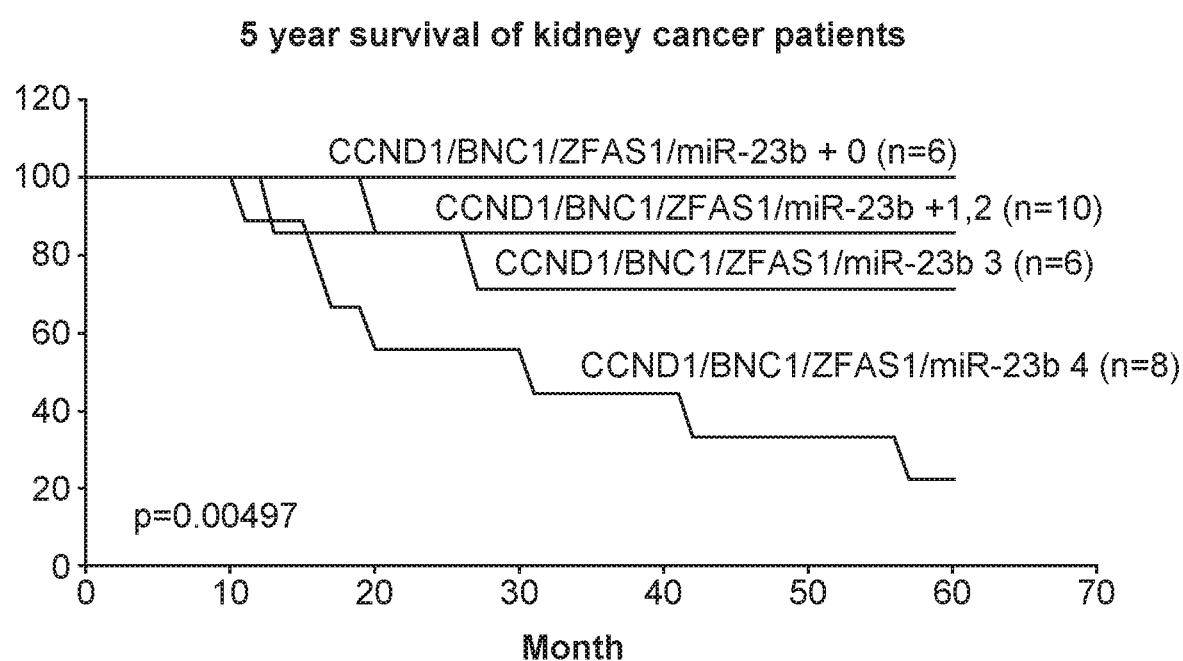
FIG. 2F shows 60 months survival curve of the kidney cancer patients after surgery.

FIG. 2F shows 60 months survival curve of the kidney cancer patients after surgery based on the expression profile of oncogene (CCND1), DNA methylation (BNC1), microRNA (miR-23b) and long non-coding RNA (ZFAS1) using Kaplan-Meier method. Patients with change no change in CCND1; BNC1; miR-23b and ZFAS1 expression showed 60 months survival after surgery. Patients with change in any one gene or two genes (CCND1; BNC1; miR-23b or ZFAS1) showed decrease in survival rate by 20%. Patients with change in expression of three genes (CCND1; BNC1; miR-23b or ZFAS1) showed decrease in survival rate by 20%-30%. Patients with change in expression of all four genes (CCND1; BNC1; miR-23b and ZFAS1) showed decrease in survival rate by 20%-80%. This data shows that combination of all different profile of genes can be a better predictor for kidney cancer survival.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of treating prostate cancer in a human patient wherein the treatment does not include surgical removal of the prostate cancer, the method comprising:
   analyzing a prostate cancer cell sample obtained from a subject, the analyzing comprising assaying a level of:
   (a) the expression of each of the oncogenes AMACR, SOX4, TMPRSS2, TWIST1, PSA and PAP;
   (b) DNA methylation each of the tumor suppressor genes RASSF1, TIG1, RARB, MDR1, and ID4;
   (c) the expression of each of the micro RNAs (miRNA) miR-96, miR-205, miR-31, miR-23b, miR-101 and miR-185; and
   (d) the expression of the long non-coding RNAs (lncRNA) ZFAS1 and MALAT1;
   comparing the level of each of (a), (b), (c) and (d) to the levels of the same analytes detected in a reference sample of normal prostate cells from the same patient;
   detecting in the prostate cancer cell sample obtained from a subject:
      unchanged expression of the oncogenes of (a);
      unchanged methylation of the tumor suppressor genes of (b);
      reduced expression by at least 2 fold of at least one of the miRNAs of (c); and
      increased expression by at least 2 fold of the lncRNAs of (d); and
   performing treatment of the prostate cancer of the subject comprising radiation, hormonal therapy, cryosurgery, chemotherapy, biologic therapy or high-intensity focused ultrasound, wherein the treatment does not include surgical removal of the prostate cancer.

2. The method of claim 1, wherein the prostate cancer cell sample is frozen, paraffin embedded, or formalin-fixed.

3. The method of claim 1, the assaying the level of expression comprises performing quantitative polymerase chain reaction (PCR) in absence of a reporter probe complementary to a nucleic acid sequence of the oncogenes of (a), the miRNAs of (c), or the lncRNAs of (d).

4. The method of claim 3, wherein formation of amplification product in the quantitative PCR is detected by intercalation of a dye into the amplification product.

5. The method of claim 1, wherein assaying the level of DNA methylation of the tumor suppressor genes of (b) comprises performing methylation specific PCR (MSP) and bisulfite genomic sequencing PCR (BSP).

6. The method of claim 3, wherein assaying the level of DNA methylation of the tumor suppressor genes of (b) comprises performing methylation specific PCR (MSP) and bisulfite genomic sequencing PCR (BSP).

7. The method of claim 4, wherein assaying the level of DNA methylation of the tumor suppressor genes of (b) comprises performing methylation specific PCR (MSP) and bisulfite genomic sequencing PCR (BSP).

8. A method of treating prostate cancer in a human patient wherein the treatment does not include surgical removal of the prostate cancer, the method comprising:
analyzing a prostate cancer cell sample obtained from a subject, the analyzing comprising assaying a level of:
(a) the expression of each of the oncogenes AMACR, SOX4, TMPRSS2, TWIST1, PSA and PAP;
(b) DNA methylation each of the tumor suppressor genes RASSF1, TIG1, RARB, MDR1, and ID4;
(c) the expression of each of the micro RNAs (miRNA) miR-96, miR-205, miR-31, miR-23b, miR-101 and miR-185; and
(d) the expression of the long non-coding RNAs (lncRNA) ZFAS1 and MALAT1;
comparing the level of each of (a), (b), (c) and (d) to the levels of the same analytes detected in a reference sample of normal prostate cells from the same patient;
detecting in the prostate cancer cell sample obtained from a subject:
unchanged expression of the oncogenes of (a);
increased methylation by at least 50% of at least one of the tumor suppressor genes of (b);
reduced expression by at least 2 fold of at least one of the miRNAs of (c); and
increased expression by at least 2 fold of the lncRNAs of (d); and
performing treatment of the prostate cancer of the subject comprising radiation, hormonal therapy, cryosurgery, chemotherapy, biologic therapy or high-intensity focused ultrasound, wherein the treatment does not include surgical removal of the prostate cancer.

9. The method of claim 8, wherein the prostate cancer cell sample is frozen, paraffin embedded, or formalin-fixed.

10. The method of claim 8, the assaying the level of expression comprises performing quantitative polymerase chain reaction (PCR) in absence of a reporter probe complementary to a nucleic acid sequence of the oncogenes of (a), the miRNAs of (c), or the lncRNAs of (d).

11. The method of claim 10, wherein formation of amplification product in the quantitative PCR is detected by intercalation of a dye into the amplification product.

12. The method of claim 8, wherein assaying the level of DNA methylation of the tumor suppressor genes of (b) comprises performing methylation specific PCR (MSP) and bisulfite genomic sequencing PCR (BSP).

13. The method of claim 10, wherein assaying the level of DNA methylation of the tumor suppressor genes of (b) comprises performing methylation specific PCR (MSP) and bisulfite genomic sequencing PCR (BSP).

14. The method of claim 11, wherein assaying the level of DNA methylation of the tumor suppressor genes of (b) comprises performing methylation specific PCR (MSP) and bisulfite genomic sequencing PCR (BSP).

15. A method of treating prostate cancer in a human patient wherein the treatment does not include surgical removal of the prostate cancer, the method comprising:
analyzing a prostate cancer cell sample obtained from a subject, the analyzing comprising assaying a level of:
(a) the expression of each of the oncogenes AMACR, SOX4, TMPRSS2, TWIST1, PSA and PAP;
(b) DNA methylation each of the tumor suppressor genes RASSF1, TIG1, RARB, MDR1, and ID4;
(c) the expression of each of the micro RNAs (miRNA) miR-96, miR-205, miR-31, miR-23b, miR-101 and miR-185; and
(d) the expression of the long non-coding RNAs (lncRNA) ZFAS1 and MALAT1;
comparing the level of each of (a), (b), (c) and (d) to the levels of the same analytes detected in a reference sample of normal prostate cells from the same patient;
detecting in the prostate cancer cell sample obtained from a subject:
increased expression by less than 5 fold of at least one of the oncogenes of (a);
increased methylation by less than 50% of the tumor suppressor genes of (b);
unchanged expression of the miRNAs of (c); and
unchanged expression of the lncRNAs of (d); and
performing treatment of the prostate cancer of the subject comprising radiation, hormonal therapy, cryosurgery, chemotherapy, biologic therapy or high-intensity focused ultrasound, wherein the treatment does not include surgical removal of the prostate cancer.

16. The method of claim 15, wherein the prostate cancer cell sample is frozen, paraffin embedded, or formalin-fixed.

17. The method of claim 15, the assaying the level of expression comprises performing quantitative polymerase chain reaction (PCR) in absence of a reporter probe complementary to a nucleic acid sequence of the oncogenes of (a), the miRNAs of (c), or the lncRNAs of (d).

18. The method of claim 17, wherein formation of amplification product in the quantitative PCR is detected by intercalation of a dye into the amplification product.

19. The method of claim 15, wherein assaying the level of DNA methylation of the tumor suppressor genes of (b) comprises performing methylation specific PCR (MSP) and bisulfite genomic sequencing PCR (BSP).

20. The method of claim 17, wherein assaying the level of DNA methylation of the tumor suppressor genes of (b) comprises performing methylation specific PCR (MSP) and bisulfite genomic sequencing PCR (BSP).

* * * * *

SEQUENCE LISTING

<160> NUMBER OF SEQ ID NOS: 56

<210> SEQ ID NO 1
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 1
agctggccac gatatcaact                                                   20

<210> SEQ ID NO 2
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 2
gattctcacc acttctgcca                                                   20

<210> SEQ ID NO 3
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 3
gacatgcaca acgccgagat                                                   20

<210> SEQ ID NO 4
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 4
tcttgtcgct gtctttgagc                                                   20

<210> SEQ ID NO 5
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 5
ccatccggga cagtgtgca                                                    19

<210> SEQ ID NO 6

```
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 6
tcaaggtgat gcacagtgct                                                    20

<210> SEQ ID NO 7
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 7
cccaccccct cagcaggg                                                      18

<210> SEQ ID NO 8
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 8
ctccttctct ggaaacaatg ac                                                 22

<210> SEQ ID NO 9
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 9 gtctcccta cagcagaatt                                                     20

<210> SEQ ID NO 10
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 10
cttcatctcc catataagga atg                                                23

<210> SEQ ID NO 11
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 11
tcttcctcac cctgtccgt                                                     19

<210> SEQ ID NO 12
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 12
```

-continued cacaatccga gacaggatga                     20

<210> SEQ ID NO 13
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 13
ccaaggagtt gaagtttgtg ac                  22

<210> SEQ ID NO 14
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 14
ggtgtcaatg ggacttcggt                     20

<210> SEQ ID NO 15
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 15
tcttcaccac catggagaag                     20

<210> SEQ ID NO 16
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 16
gcagagatga tgacccttttt g                  21

<210> SEQ ID NO 17
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 17 gggtattty gygtggtgtt ttg                  23

<210> SEQ ID NO 18
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 18
ccrccttacc cttccttcc                      19

<210> SEQ ID NO 19
<211> LENGTH: 21
<212> TYPE: DNA

```
<213> ORGANISM: Artificial sequence
<220> FEATURE:
<223> OTHER INFORMATION: Synthetic nucleic acid

<400> SEQUENCE: 19
tggtgttttg cggtcgtcgt c                                            21

<210> SEQ ID NO 20
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 20
tacccttcct tccctccttc g                                            21

<210> SEQ ID NO 21
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 21
tgtgtggtgt tttgtggttg ttgtt                                        25

<210> SEQ ID NO 22
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 22
tacccttcct tccctccttc a                                            21

<210> SEQ ID NO 23
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 23
ggtttgggtt agaagtatty ggttttg                                      27

<210> SEQ ID NO 24
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 24
cccataaaac cactcctttt cc                                           22

<210> SEQ ID NO 25
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 25
tgcgttgcgg aggcgatgtc                                              20
```

<210> SEQ ID NO 26
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 26
ctccttttcc acgtttcccg                                              20

<210> SEQ ID NO 27
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 27
gttttgtgtt gtggaggtga tgtt                                         24

<210> SEQ ID NO 28
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 28 cactccttttt ccacatttcc ca                                          22

<210> SEQ ID NO 29
<211> LENGTH: 24
<212> TYPE: DNA
<213> ORGANISM: Artificial sequence
<220> FEATURE:
<223> OTHER INFORMATION: Synthetic nucleic acid

<400> SEQUENCE: 29
ygagttgttt gaggattggg atgt                                         24

<210> SEQ ID NO 30
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 30
ccraatacrt tccraatcct acc                                          23

<210> SEQ ID NO 31
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 31
gattgggatg tcgagaacgc                                              20

<210> SEQ ID NO 32
<211> LENGTH: 20
<212> TYPE: DNA
<213> ORGANISM: Artificial sequence
<220> FEATURE:

<223> OTHER INFORMATION: Synthetic nucleic acid

<400> SEQUENCE: 32
ttccgaatcc taccccgacg                                                  20

<210> SEQ ID NO 33
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 33
gaggattggg atgttgagaa tgt                                              23

<210> SEQ ID NO 34
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 34
cattccaaat cctaccccaa ca                                               22

<210> SEQ ID NO 35
<211> LENGTH: 32
<212> TYPE: DNA
<213> ORGANISM: Artificial sequence
<220> FEATURE:
<223> OTHER INFORMATION: Synthetic nucleic acid

<400> SEQUENCE: 35
gtttygtagt ttttygagga attagtattt ag                                    32

<210> SEQ ID NO 36
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 36
acraaacrac tatactcaac cc                                               22

<210> SEQ ID NO 37
<211> LENGTH: 29
<212> TYPE: DNA
<213> ORGANISM: Artificial sequence
<220> FEATURE:
<223> OTHER INFORMATION: Synthetic nucleic acid

<400> SEQUENCE: 37
gaggaattag tatttagtta attcgggtc                                        29

<210> SEQ ID NO 38
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 38
atactcaacc cacgccccg                                                   19

```
<210> SEQ ID NO 39
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 39
tgaggaatta gtatttagtt aatttgggtt                              30

<210> SEQ ID NO 40
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 40
ctatactcaa cccacacccc a                                       21

<210> SEQ ID NO 41
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 41
aattgttggg ttygggagtg                                         20

<210> SEQ ID NO 42
<211> LENGTH: 27
<212> TYPE: DNA
<213> ORGANISM: Artificial sequence
<220> FEATURE:
<223> OTHER INFORMATION: Synthetic nucleic acid

<400> SEQUENCE: 42
craaaaaaac aaacaaactc craaccc                                 27

<210> SEQ ID NO 43
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 43
ttgggttcgg gagtgtcgc                                          19

<210> SEQ ID NO 44
<211> LENGTH: 18
<212> TYPE: DNA
<213> ORGANISM: Artificial sequence
<220> FEATURE:
<223> OTHER INFORMATION: Synthetic nucleic acid

<400> SEQUENCE: 44
cgtccgcgac cgactccg                                           18

<210> SEQ ID NO 45
<211> LENGTH: 21
<212> TYPE: DNA
<213> ORGANISM: Artificial sequence
<220> FEATURE:
<223> OTHER INFORMATION: Synthetic nucleic acid
```

```
<400> SEQUENCE: 45
tgttgggttt gggagtgttg t                                              21

<210> SEQ ID NO 46
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 46
cccatccaca accaactcca                                                20

<210> SEQ ID NO 47
<211> LENGTH: 19
<212> TYPE: DNA
<213> ORGANISM: Artificial sequence
<220> FEATURE:
<223> OTHER INFORMATION: Synthetic nucleic acid

<400> SEQUENCE: 47
cggaagatcg tcgccacct                                                 19

<210> SEQ ID NO 48
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 48
tccaggtagt tcatggccag                                                20

<210> SEQ ID NO 49
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 49
catgtcgatg gacttccaga                                                20

<210> SEQ ID NO 50
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 50
ggacagcttg gatcacactt                                                20

<210> SEQ ID NO 51
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 51
agttyggygg gggtagatat                                                20

<210> SEQ ID NO 52
<211> LENGTH: 26
```

```
<212> TYPE: DNA
<213> ORGANISM: Artificial sequence
<220> FEATURE:
<223> OTHER INFORMATION: Synthetic nucleic acid

<400> SEQUENCE: 52
acrccctaaa tcaacrcaac taaaac                                            26

<210> SEQ ID NO 53
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 53
gtcgtcggcg aggttttcgc                                                   20

<210> SEQ ID NO 54
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 54
aaacgaaacc gtaaccccg                                                    20

<210> SEQ ID NO 55
<211> LENGTH: 25
<212> TYPE: DNA
<213> ORGANISM: Artificial sequence
<220> FEATURE:
<223> OTHER INFORMATION: Synthetic nucleic acid

<400> SEQUENCE: 55
tgttggttgt tggtgaggtt tttgt                                             25

<210> SEQ ID NO 56
<211> LENGTH: 26
<212> TYPE: DNA
<213> ORGANISM: Artificial sequence
<220> FEATURE:
<223> OTHER INFORMATION: Synthetic nucleic acid

<400> SEQUENCE: 56
caactaaaac aaaaccataa ccccca                                            26
```